US012214032B2

(12) United States Patent
Wu et al.

(10) Patent No.: US 12,214,032 B2
(45) Date of Patent: Feb. 4, 2025

(54) PORCINE REPRODUCTIVE AND RESPIRATORY SYNDROME VACCINE VIRUS

(71) Applicants: Elanco US, Inc., Greenfield, IN (US); Elanco UK AH Limited, Hampshire (GB)

(72) Inventors: Stephen Qitu Wu, Fishers, IN (US); Cinta Prieto Suarez, Madrid (ES); Geoffrey Gregory Labarque, Neuilly sur Seine (FR)

(73) Assignees: Elanco UK AH Limited, Hampshire (GB); Elanco US Inc, Greenfield, IN (US)

( * ) Notice: Subject to any disclaimer, the term of this patent is extended or adjusted under 35 U.S.C. 154(b) by 517 days.

(21) Appl. No.: 17/618,625

(22) PCT Filed: Sep. 27, 2019

(86) PCT No.: PCT/EP2019/076174
§ 371 (c)(1),
(2) Date: Dec. 13, 2021

(87) PCT Pub. No.: WO2021/037387
PCT Pub. Date: Mar. 4, 2021

(65) Prior Publication Data
US 2022/0241393 A1 Aug. 4, 2022

(30) Foreign Application Priority Data
Aug. 29, 2019 (EP) .................................... 19382734

(51) Int. Cl.
*A61K 39/12* (2006.01)
*A61P 31/14* (2006.01)
(Continued)

(52) U.S. Cl.
CPC .............. *A61K 39/12* (2013.01); *A61P 31/14* (2018.01); *C12N 7/00* (2013.01); *A61K 2039/525* (2013.01); *A61K 2039/552* (2013.01)

(58) Field of Classification Search
None
See application file for complete search history.

(56) References Cited

U.S. PATENT DOCUMENTS 10,155,035 B2  12/2018  Fang et al.
10,300,126 B2  5/2019  Fang et al.
(Continued)

FOREIGN PATENT DOCUMENTS

CN    105829528 A    8/2016
JP    2019-505217 A  2/2019
(Continued)

OTHER PUBLICATIONS

International Search Report of International Application No. PCT/EP2019/076174, mailed Jul. 23, 2020.
(Continued)

*Primary Examiner* — Shanon A. Foley
(74) *Attorney, Agent, or Firm* — McBee Moore & Vanik IP, LLC

(57) ABSTRACT

The present invention relates to modified, live Porcine Reproductive and Respiratory Syndrome viruses. Viruses were genetically analyzed and selected based on phylogenetic grouping for modification by repeated passage in tissue culture. The modified, live viruses were assessed for the ability to provide protective immunity to heterologous viruses. The modified, live viruses are useful in vaccines, particularly in vaccines which can treat infection of swine by multiple heterologous viruses.

20 Claims, 1 Drawing Sheet
Specification includes a Sequence Listing.

(51) Int. Cl.
*C12N 7/00* (2006.01)
*A61K 39/00* (2006.01)

(56) References Cited

U.S. PATENT DOCUMENTS

| | | |
|---|---|---|
| 2003/0072771 A1 | 4/2003 | Mengeling et al. |
| 2003/0157689 A1 | 8/2003 | Calvert et al. |
| 2014/0314808 A1 | 10/2014 | Fetzer et al. |
| 2022/0241393 A1* | 8/2022 | Wu .................... C12N 7/00 |

FOREIGN PATENT DOCUMENTS

| | | |
|---|---|---|
| WO | 02/072802 A2 | 9/2002 |
| WO | 2011/128415 A1 | 10/2011 |
| WO | 2013/017568 A1 | 2/2013 |
| WO | 2016/012406 A2 | 1/2016 |
| WO | 2018/112169 A2 | 6/2018 |

OTHER PUBLICATIONS

Gyula Balka et al., "Genetic diversity of PRRSV 1 in Central Eastern Europe in 1994-2014: origin and evolution of the virus in the region", Scientific Reports, May 17, 2018, vol. 8, No. 1.

"PRRS virus EUX strain genome", XP002798986, Apr. 11, 2013, retrieved from EBI accession No. GSN:BAK46659 Database accession No. BAK46650 Sequence EUX GSN:BAK46659 (85% identity to seq. ID 1).

"PRRS virus DNA sequence", XP002799719, Dec. 12, 2002, retrieved from EBI accession No. GSN: ABS76688 Database accession No. ABS76688.

* cited by examiner

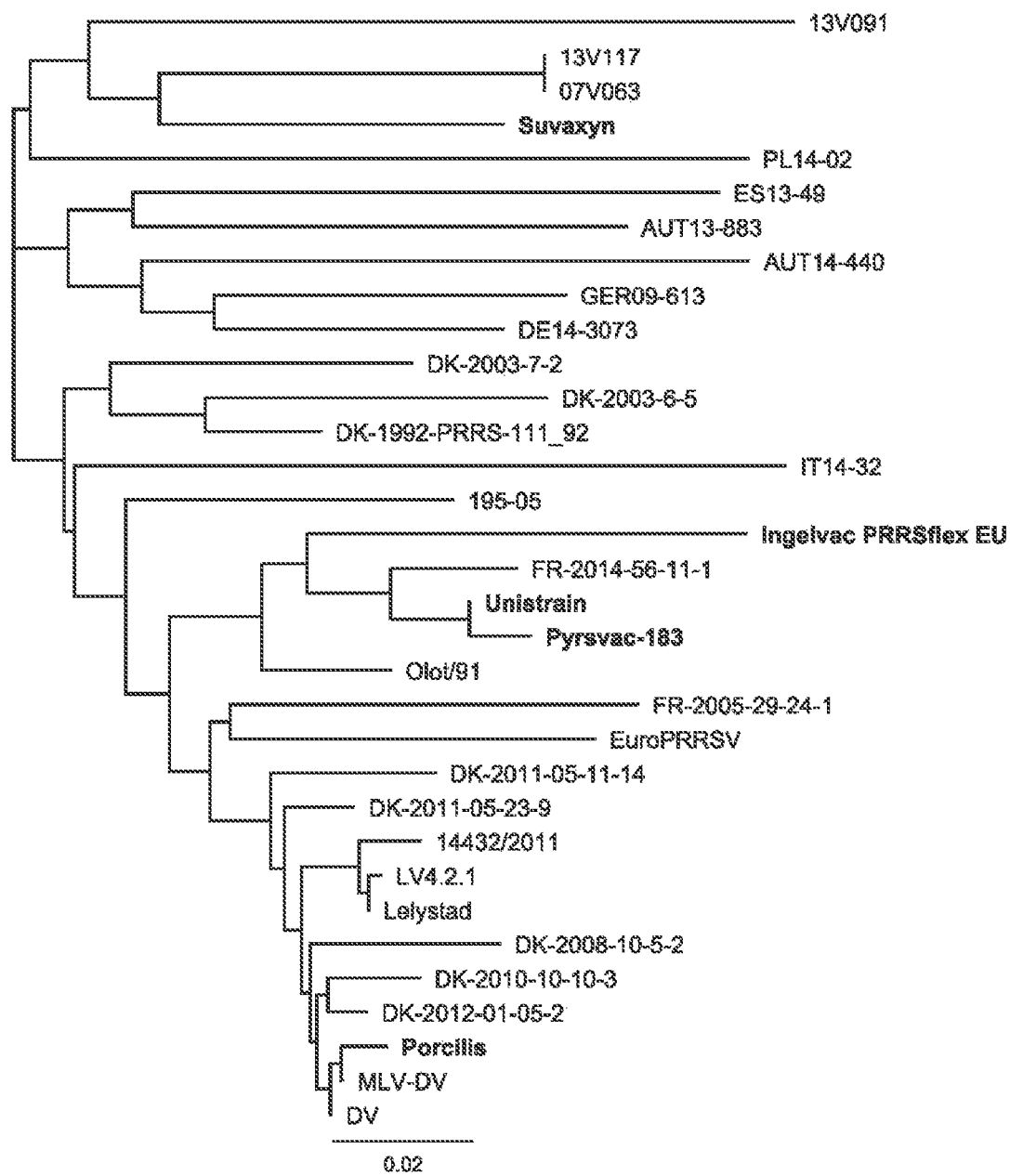

SEQUENCE LISTING

```
<160> NUMBER OF SEQ ID NOS: 4

<210> SEQ ID NO 1
<211> LENGTH: 15081
<212> TYPE: DNA
<213> ORGANISM: Artificial Sequence
<220> FEATURE:
<223> OTHER INFORMATION: cDNA from Porcine Reproductive and Respiratory
      Syndrome virus

<400> SEQUENCE: 1
atgatgtgta gggtattttc cctacgtgcg caacactttt tgtgtttgtg tgcctcggag      60
gcgtgggtat agccccgccc cacctcttgg ccctgttcta gcccaacagg tatccttctc     120
tctcggggcg agtgcgccgc ctgctgcttc cttgcagcgg gaaggacctc ccgagtactt     180
ccggagagcg cctgctttac gggatctcca ccctttaacc atgtctggga cgttctcccg     240
gtgcatgtgc accccggcgg ctcgggtgtt ttggaacgcc ggccaagtct tttgcacacg     300
```

-continued

| | |
|---|---|
| gtgtctcagt gcacggtctc ttctctctcc agagcttcag gacctcagtt ttggtgcact | 360 |
| cggcttgttt tacaagccta aagataagct tcattggaaa gttcctgttg gtatacctca | 420 |
| ggtagagtgc actccatccg ggtgctgttg gctttcagct attttccctc tggcacgtat | 480 |
| gacctccggc aaccacaact ttctccagag acttgtgaag gttgctgacg ttttgtaccg | 540 |
| tgatggttgc ttggcgcccc gacatcttcg tgaacttcaa gtttacgagc gcggctgcag | 600 |
| ttggtacccg attacgggac ccgtgcccgg gatgggtctg tttgcgaatt ccatgcacgt | 660 |
| atccgaccag ccttttccctg gtgccaccca tgtgctgact aactcgcctc tgcctcaaca | 720 |
| ggcttgtcgg cagcctttt gcccatttga ggaggtcat tctggtttgt tcaagtggaa | 780 |
| taaattcgtg attttatag acccccccct taacggtaga cgccgcatga tgtgggcacc | 840 |
| tgaatccgac gattcagcca acttggaggt gttgccgcct gaattagaac gtcaagttga | 900 |
| gattctcact cggagtttcc ctgctcacca ccctgtcaac ctcagcgact gggagctttc | 960 |
| cgactcccct gaacacggtt ttccttcag cacttatcat tcttctggtt acgttgccaa | 1020 |
| aaaccctgac gtgtttgata gcaagtgctg gctttcctgt tttctgagct tgtcgcctga | 1080 |
| ggtgtggcat cgtgaggagc tcttggctag cgcatttggt tatcaaacca agtggggcgt | 1140 |
| gcatggcaaa tacctccaac gcaggcttca aattaatggc atccgtgctg tggttgatcc | 1200 |
| agacggcccc attcacgttg aagcgctgtc ttgcccccag tcttggatca ggcatttgac | 1260 |
| tctggacgat gaagtaaccc cagggttcgt tcgcctgacg tctcttcgca tcgtaccgaa | 1320 |
| cacagaacct accaccttc gcgtctttcg ttttggggcg cataagtggt atggtgccgc | 1380 |
| cggtaaacga gctcgcgcaa agcgtgctgc caagagcgag aaggactcgg ttactgcatc | 1440 |
| caaggctgtc caaccaactc ttgcctgtaa aaacaccacc tattcccac caacggacgg | 1500 |
| gtcttgtggt tggcatgttc tcgccgccat aatgaaccgg atgttaaatg gtgacttcac | 1560 |
| gtcccctta accccgtaca acagaccaga agatgattgg gcatcggatt atgatcttgc | 1620 |
| tcaggcgatt caatgtctac aattacctgc taccatagtc cggaatcgcg cctgtcctaa | 1680 |
| tgctaaatac ctcataaaac tcaacggagt tcactgggag gtagaggcaa ggtctgggtt | 1740 |
| tgcccctcgc tcccttcccc gcgagtgtgt ggtcggtgtt tgctccgaag gctgtgtcgc | 1800 |
| aacaccctac ccagagaatg ggctgcctaa gcgggcactt gaggccttag cgtctgctta | 1860 |
| cagattgcct tccgattgcg tcagttctgg cattgctgac tttcttgctg accccctcg | 1920 |
| ggagttttgg actcttgaca aaatgctgac ttccccatca ccggagcaat ccggcttttc | 1980 |
| tagtctgtac agattgctat tagaggttgt cccgcaaaaa tgcggtgcca cggagggggc | 2040 |
| tttcatctat gccgttgaaa ggatgttgaa ggattgtcca agttccaagc aggccatggc | 2100 |
| tctcctagca aaagtcaaag tcccatcctc aaaggcctcg tctgtgacct tggatgagtg | 2160 |
| tttttcctacg gacgttccgg ccgacttcaa gccagcgtct catgagaagc tcaaagttc | 2220 |
| cggtactgtt gttgtcctgt gttcaccggg agcagaagag tcagaaaaag tgacccctaga | 2280 |
| agaagttcgg gagggtggct ataaaaccat ctgccctgca cccccttactg agggtcctaa | 2340 |
| tgatgaacag gcacaagtag ctgtcggcga gcagctgagg ctcagcggtt gtggtttggc | 2400 |
| agccgggaac gctccagccc cggctggtcc aattgacaca gtaagcagag atcttccct | 2460 |
| tccggacttc atgaaagaaa acatgtccaa taattgggag gatggaccat tggatttgtc | 2520 |
| ccaatcggca tcagctgtca tgacaacccc tgtaggagag cacacatcca aaaatccagg | 2580 |
| ttctggtatc ggtgacttcc ctgttactgt tcgaggcttt acctcaacgg ggctcgtact | 2640 |

```
tcgtcacgtt gagcactgcg gtacggagtt gggcgacgac agtccgcctt tggatttgtc    2700
tgattcgcag acctcgaacc ggcctctgga tctatcccta gctgcttggc cagtgaagac    2760
caccgcatct gaccctggct gggttcatgg tagacgcgaa cctgtctttg taaagcctcg    2820
gaatgttttc tctgatggcg attcagttct tcagttcggg ggacctcctg aatctagctc    2880
tgtcaccgag tttgaccgga caaaagatac tccggcggtc gacacccttg tcaacttgac    2940
gactccaaac gaggcccccc ctgtaaccga ttctcgtgaa cttgccgaac tcaaacgccc    3000 gcgttttttcc gcacaagccc taattgaccg aggcggtcca ctcgctgatc tccatgcaga    3060
gataaaaaat cgggtatacg aacaatgcct ccaagcttgt gagcccggta gtcgtgcgac    3120
cccagccacc aagaagtggc ttgacaaaat gtgggatagg gtggacatga aacttggcg    3180 ctgcacctcg cagttccaag ctggtcgtat tcttgcatcc ctcagtttcc ttcctgacat    3240
gatccgagac acaccacctc ctgtacccag gaagagccgg gttagtgaca gtgtcggtct    3300
gaagcaacta gtgactcagt gggataagaa actgagtgtg gcccccgag aagggcttat    3360 tgagtcagtg ctcgaccaaa ccgttccgcc gcccacggat gtccagcaag gagataccac    3420
ccctccccat gaaccacccg atgcgccgga tttgcctggt cgagtgggta caagcagagg    3480
ttggaagggt cttacgcttt ccggcgcccg cctcgcgggg tctgtcagcc agcgcctcat    3540
ggcatgggtt tttgaagttt actcccatct cccagctttt atgctcacac tttctcgcc    3600 gcggggctct atggcttcag gtgattggct ttttgcaggt attgttctac ttgctctctt    3660
gctctgtcgc tcttacccaa tactcgggtg cctacccta ttgggtgtct tttctggttc    3720
tctgcggcgc gttcgtctgg gcgtatttgg ctcttggatg gcttttgctg tattttttatt    3780 cacgactcca tccaacccag tcggttcttc ttgtgagcac gattcgccgg aatgtcacgc    3840
tgagcttctg gctcttgagc agcgccaact ttgggaaccct gtgcgggcc ttgtggtggg    3900 cccctcaggt ctcctatgcg tcattcttgg taggttactc ggtgggtcac gttatctctg    3960
gcttgctttc ttacgtctat gcttgcttgc agatttggcc ttttctcttg tttatgtggt    4020
gtcccagggg cgttgccaca agtgctgggg aaagtgtata aggacagccc ccacggaggt    4080
ggctctcaat gtgttccctt tttcgcgcgc cacccgttcc tctcttgtgt ccttgtgtga    4140
tcgattccaa acaccaaaag gggttgatcc ggtgttcttg caacaggtt ggcgcgggtg    4200 ctggtgtggt gagagcccca ttcatcaatc acaccaaaaa cccatagctt acgccaactt    4260
ggatgaaaag aagatatctg cccaaacggt agtcgctgtt ccatacgatc ctaaccaagc    4320
tatcaaatgc ctgaaagttt tgcaggcggg ggggccatt gtggaccaac caacacctga    4380
ggtcgttcgt gtatccgaga tccccttttc agctccgttt ttcccgaaag ttccggtcaa    4440
cccagactgc aaggtagtgg tagattcgga cacttttgtg gctgcggttc gttgcggtta    4500
ctcaacaaca caactggttt tgggtcgggg caattttgcc aagttgaatc aggccccttc    4560
taaggcctct gcttacacaa aaacgactgg tgggcctct tatactttg ctgtagttca    4620 agtgtctgtg tggactctta tccacttcat tctcggcctt tggttgatgt cgcctcaagt    4680
ttgtggtcga ggaacttccg acccatggtg ttcagatcct ttttcgtacc ccacttatgg    4740
cccaggcgtt gtgtgctcgt ctcaactttg tgtatccgcc gatggtgtta ccctaccgtt    4800
gttttcggcc gtggcccgac tttctggcag ggaggtgggg attttttattt tagtgtttgt    4860 ctccttggct gctttagccc atcgctgggc ccttaaggct gacatgttag taatcttttt    4920
agcgttttgt gcttacgcat ggcccatgag ttcctggcta atttgccttt tcccaacact    4980
cttaaggtgg atcaccctcc accctctcac catactttgg gtgcattcat tcttagtgtt    5040
```

```
ctgcctgccg gctgccggcg ttctttcatt agggataact ggtcttctct gggcagttgg    5100
acgctttacc caagttgccg gacttatcac accttatgac atccaccaat atacttctgg    5160
gccgcgtggt gcaactgctg tggccacggc tccagagggc acttacatgg ccgccgtccg    5220
gagagctgct ctaactgggc gaactctaat cttcaccccg tctgcggtcg ggtcccttct    5280
cgaaggtgct ttcaggactc ataaaccttg cctcaacacc gtgaatgttg tgggttcttc    5340
cctcggttct ggaggagtct tcaccattga tggcaggaaa actgtcgtca ctgccaccca    5400
cgtgctgaat ggcgacacag ctagagttac cggtgactcc tacaaccgca tgctcacttt    5460
caagaccaat ggtgattatg cctggtccca tgctgatgac tggcagggtg ctgccccagt    5520
ggttaagatt acaaaaggat accgcggtcg tgcttattgg caaacatcaa ccggtgtcga    5580
gcccggtatc attggagagg ggttcgcctt ctgttttacc agctgcgtg actcggggtc      5640 gcctgttata tctgaagctg gtgaccttat cggcatccat actggttcaa acaaacttgg    5700
ttcaggtctt gtgacaaccc ctgaagggga gacctgctca attaaggaaa ctagactttc    5760
tgacctctct aagtattttg cgggtccgtg cgtccctctt ggggacatta agttaagccc    5820
tgccatcatt cctgacatga catctgttcc aagcgacttg gcatcgcttc ttgcttctgt    5880
ccctgtcatg gagggcggtc tctcgactgt tcaacttttg tgtgtctttt tcttctctg     5940 gcgcatgatg ggtcatgctt ggacacccat cgttgctgtg ggcttctttt tgctgaatga    6000
aatccttcca gcagttttag tccgagccgt gttctctttt gcactctttg tgcttgcatg    6060
ggccaccccc tggtctgcac aggtgcttat gatcagactt cttacagcgt cccttaaccg    6120
gaacaagtct tctctggcgt tttacgcatt cgggggtgtc gtcggcctgg ctgctgaaat    6180
cggaactttt gctggtaaac tacctgaatt gtctcaagct ctttcgacat actgcttttt    6240
gccaagattt cttgctgtat ctagttgtgt tcccatcatc atcatcggtg gcttcatgt     6300 tctcggcgtg attttgtggc tattcaaata ccggtacctt catgacgtgc tggttggtga    6360
tgggagtttt tcaaaagcct tcttcctacg gtattttgct gagggcaatc tcagaaaggg    6420
tgtttcacaa tcctgtggca tgagtaacga gtccctaacg gctgctttgg cctgcaagtt    6480
gtcgcaagct gaccttgaat ttttatccag cttaacgaac ttcaagtgct tgtgtctgc     6540 ctctaacatg aaaaatgctg ctggccagta cattgaagca gcgtatgcca aggccctgcg    6600
ccaagagttg gcctctctag ttcaggttga caaaatgaaa ggagttttgg ccaagcttga    6660
ggcctttgct gaaacagcca ccccgtctct agacacgggt gatgtgattg ttctgcttgg    6720
gcaacaccct cacggatccg tcctcgacat aaatgtgggg actgagagga aaactgtgtc    6780
cgtgcaagag acccggagtt tgggcggctc caggtttagt gtttgtactg ttgtgtccaa    6840
tacccctgtg gatgccttaa ccgacatccc acttcaaaca ccaacccccc tttttgagaa    6900
tggtccacgc catcgtagcg acgaagacga tcttaaggtt gagaggaaaa agaaacactg    6960
tgtgtccctc ggcttccaca acatcaacgg taaggtttac tgtaaaattt gggacaagtc    7020
caccggtgat accttttaca cagatgattc ccggtatact caagaccatg ttttttcagga   7080 caggtcagcc gactacaggg acagggacta tgaaggtgtg caagccaccc ccccacaggg    7140
atttgatcca aaatctgaaa ccccggttgg cactgtcgtg atcggcggta tcacgtataa    7200
caggtatctg gtaaaaggta gagaggttct ggttctcaag cccgacaact gtcttgaagc    7260
cgccaggttt tctcttgagc aagctctcgc tgggatgggc caaacttgtg acctcacggc    7320
cgctgaagtg gaaaagctaa agcgtatcat cagtcaactt caaggcttga ccactgaaca    7380
```

```
agctttaaac tgttagccgc cagcggcttg acccgctgtg gccgcggcgg cttagttgtg    7440
actgaaacgg cggtgaaaat cataaaatac cacaacagaa cttt caccttaggccccttta   7500
gacttgaaag tcacatccga ggtggagtg aagaaatcaa ctgagcaagg ccacgctgtt     7560
gtggcaaact tatgttccgg tgttgtcttg atgagacctc acccaccgtc ccttgttgac    7620
gttctcttga aacccggact tgacacgaca cctggtattc aaccggggca tggggccggg    7680
aatatgggcg tggacggttc tatttgggat tttgaaaccg cacctacaaa ggcggaactt    7740
gagttgtcca agcaaataat tcaagcatgt gaagtcaggc gcggggacgc cccgaacctc    7800
caactccctt ataagctcta ccctgttaga ggggatcctg aacggcataa gggtcgcctt    7860
atcaatacca ggttcggaga tttgccctat aaaactcctc aggacaccaa gtccgcgatc    7920
catgcggctt gttgcttgca ccccaatgga gcccccgtgt ctgatggcaa atccacgcta    7980
ggcaccactc ttcaacatgg ttttgagctt tatgtcccca ctgtgcccta gtgtgtcatg    8040
gagtaccttg attcacgccc tgacacccct ctcatgctca gcaaacatgg tacttccaag    8100
gctgctgcag aagatctcca aaaatatgat ctgtccaccc aaggatttgt cctgcctggg    8160
gttctgcgcc tagtgcgcaa attcatcttc ggccacatag gtaaggcgcc gccattgttc    8220
cttccatcaa cctatcccgc taagaattct atggcaggga tcaacggtca gaggtttcca    8280
acaaaggatg tccagagcat acctgaaatt gatgagatgt gtgcccgtgc cgtcaaggag    8340
aattggcaaa ctgtgacacc ttgtaccctc aagaagcagt actgttccaa gcctaaaacc    8400
aggaccatcc tgggcaccaa caatttcatt gccctggctc acagatcagc actcagcggc    8460
gtcacccagg catttatgaa gaaggcttgg gagtccccaa ttgctttggg aaaaaataaa    8520
ttcaaagagc tgcattgcac ggttgccggc aggtgccttg aggccgatct ggcctcctgt    8580
gatcgcagca cccccgccat tgtaagatgg tttactgcca acctcctgta tgaacttgca    8640
ggatgtgaag accatttgcc cagctatgtg cttaactgct gtcatgacct cgtggcaaca    8700
caagatggcg ccttcacgaa acgtggtggc ctgtcgtccg gggatcccgt cactagtgtg    8760
tccaacaccg tgtattcact agtgatttat gcccagcaca tggtattgtc agccctgaaa    8820
atgggccacg agattggtct caagttcctc gaggaacagc ttagattcga ggaccttctt    8880
gaaattcagc ccttgctggt atactctgac gaccttgtct tgtatgctga aaaacccact    8940
tttcccaatt accattggtg ggttgaacat ctcgacttga tgtttgggttt caagacggac    9000
ccgaagaaaa ctattataac agacaagccc agcttccttg gctgcagaat tgaggcaggg    9060
cgacaactag tccccaatcg tgaccgcatt ctcgccgctc ttgcatacca catgaaggca    9120
cagaacgttt cagagtatta tgcatctgct gctgcagttc ttatggattc atgtgcctgc    9180
atcgaccatg accctgagtg gtatgaggac ctcatctgcg gcatcgccag gtgcgctcgt    9240
caagatggct atagttttcc cggcccggca ttttttatgt ccatgtggga gagactgaaa    9300
agccacaatg agggaaagaa attccgccac tgccggcatct gtgatgccaa ggccgaccac    9360
gcgtccgcct gtggacttga cttgtgtctg tttcactcat attttcacca gcactgccca    9420
gtcactctgg gttgtggtca ctatgccggt tcaaggaat gccagcagtg tcagtcacct    9480
attggaaccg gcaagtctcc tcttgacact gtgctgaaac aaatcccgta taacctcct    9540
cgcactgtca tcatgagggt ggacaacaag acaacggccc tcgatccagg gagatatcag    9600
tcccgtcgag gcctcgttgc agtcagaaga ggcattgcag gcaatgaagt cgatcttgct    9660
gatgagact accaggtagt gccccttttg ccgacttgca aagacataaa tatggtgaag    9720
gtcgccagta atgtgctagt tagcaagttc ataagtggga cgccaggttc cggaaagacc    9780
```

```
acctggttat tgagtcaggt ccaggatgaa gatgtcattt acacacccac tcatcagacc    9840
atgtttgaca tagtcagtgc tctcaaagtt tgcaggtatt ccataccagg ggcctcagga    9900
ctcccttttc caccgcctgc caggtccggg ccgtgggtta agctcattgc cagcgggcac    9960
gtccccggtc gagtgtcgta cctcgatgag gccggatatt gcaatcattt ggatatactt   10020
agactacttt ctaaaacacc tctcgtgtgc ttgggtgacc ttcagcaact tcaccctgtc   10080
gggttcgatt cccactgtta tgtttttgat caaatgcctc aggagcagct gaccactatt   10140
tatagatttg gtcccaacat ctgcacagcc atccagcctt gctacagaga aaaacttgaa   10200
tccaaggcta ggaacaccag ggtggttttc accacccggc cagtgacctt tggtcaggtg   10260
ttaacaccgt accataaaga tcgcgttggc tctgcgataa caatagattc atcccaaggg   10320
gccacctttg atgttgtgac attacacttg ccatctccga aatccctaaa taaatcccga   10380
gcacttgtgg ccatcactcg ggcgagacat gggttgttca tttacgaccc ccacaaccaa   10440
ctccaggagt tttttaacct gactcctgag cacactgatt gtaacctagt gttcagccgt   10500
ggggacgagc tggtggtttt gagtgcggat aatacagtca caactgtagc gaaggcccta   10560
gaggtgggtc catctcgctt ccgagtgtca gacccgaggt gcaagtctct tttggctgcc   10620
tgttcggcta gtctggaggg gagctgcatg ccgctaccac aagtggcaca caacctgggg   10680
ttttactttt ccccggacag ttcagcattt gcacctctgc cagaagagtt ggcgccacat   10740
tggccagtgg ttacccacca gaacaattgg gcgtggcctg accggcttgt tgccagcatg   10800
cgcccgattg atgcccgcta cagcaaacca atggtcggtg cagggtatgt agtcgggccg   10860
tccacctttc tcggcacccc cggtgtggtg tcatattatc tcacactata cgtcaaaggt   10920
gagcctcagg ccttaccaga aacacttgtt tcaacaggac gtatagccac agactgtcgg   10980
gagtatctcg acacggctga agaagaggca gcaagggaac tcccccacgc attcattggc   11040
gatgtcaaag gtaccacgat tgggggatgt catcacatca catcaaaata tttgcccagg   11100
ttcctgccca aggactctgt tgccgtagta ggagtgagtt cgcctggtag agctgctaaa   11160
gccgtgtgca ctctcaccga tgtgtatctt cccgaactcc gaccatatct gcaacctgaa   11220
acggcatcaa aatgttggaa actcaagtta gatttcaggg acgttcgatt aatggtctgg   11280
aaaggagcta ccgcctactt ccagttggaa gggcttacat ggtcagcgtt gcccgattat   11340
gccaggttta ttcagctgcc caaggacgcc gtggtataca tcgacccatg cataggaccg   11400
gcgactgcca accgcaaggt tgtgcgaacc acggattggc gggccgacct ggcagtgaca   11460
ccgtatgatt acggggccca gcacattctg acaacagctt ggtttgagga cctcgggccg   11520
cagtggaaaa ttttgggggtt gcagcccttc aggcgagcgc ttggccttga aaacaccgag   11580
gactgggcga ttcttgcgcg ccgtatgaat gacggcaagg attacattga ctacaattgg   11640
cattgcgtcc gaggacgccc acgcgctatc tacgggcgcg ctcgtgacca tacttaccat   11700
tttgccttgg gcacagaatt gcaggtggag ctgggtaaac cccaactgcc gcctgagctg   11760
gtaccgtgaa cctgaagtga tgcaatgggg ttgttatgga gtaaaatcag ccagctgttt   11820
gtggacgcct tcacagagtt ccttgttagt gtggttgata tcgtcatctt tcttgccata   11880
ctgtttgggt tcaccgtcgc agggtggtta ctggtctttt ttctcagatt ggtttgctcc   11940
gcgattctcc gttcgcgctc tgccattcac tctcccgaac tatcgaaggt cctatgaagg   12000
cctgctaccc aattgcaggc ctgatgtccc acaattcgca ttcaagcacc cattgggtat   12060
gctttggcac atgcgagttt cccaattgat tgacgagatg gtctctcgtc gtgtctacca   12120
```

```
gaccatggaa caatcaggtc aagcggcctg gaagcaggta gttggtgagg ccacccttac    12180
gaagctatca aggctcgatg tagttaccca cttccagcac ttggccgcaa cagaggcgga    12240
ttcttgccgc tttcttagct cacgactcgt gatgctaaag aatcttgccg ttggtaatgt    12300
gagcctacag tacaacacca cgtcagacca cgttgaactc attttttccca ctccaggtgc    12360 gaggcccaag ttgaccgatt tcagacaatg gctgatcagt gtccatgctt ctattttttc    12420
ctctgtggcc tcatctgtta ccttgtttgt ggtgctttgg cttcgagtcc caatgctacg    12480
ctatgctttt ggtttccatt ggctcacggc aacacatcat tcgagttaac tattaattac    12540
accatatgca agccctgcct caccagtcaa gcggctaaac aaaggcttga acctggtcat    12600
agcatgtggt gcaggatagg ggacaccagt tgtgaggaga gtgaccacga tgagttgtca    12660
atgaccatcc cgtctgggta cgataacctc aaactcgagg ctattatgc ttggctggcc     12720 ttcctgtcct tttcctacgc ggcccaattc catccggagc tgtttggaat agggaacgtg    12780
tcgcgtgttt ttgtggacaa gcgacaccag ttcatttgtg cggagcatga tggacccaat    12840
tcaaccgtgt ccattaatca taacatctcc gcatcgtacg cggtgtatta ccatcatcag    12900
gtagacggag gtaactggtt ccacttggaa tggctgcggc cgttcttctc ctcctggttg    12960
gtgctcaatg tctcatggtt tctgaggcgt tcgcctgcaa gccctgtttc tcgacgcatc    13020
tatcagatat taagaccaac acgaccgcgg ctgccggttt tatggtcctt caaaacattg    13080
aatgtctcca acctcacacg ggccccgcag cgcaagggac catcccccaa gcgaaacggt    13140
cacaatgtcg ccaagccgtc ggcactcccc agtacatcac gataacggct aacgtgactg    13200
acgaatcata cttgtataac gcagatttgc taatgctttc tgcgtgcctt ttctatgcct    13260
cagaaatgag cgagaaaggc tttaaagtca tctttgggaa cgtctctggc gtcgtttccg    13320
cttgtgtcaa tttcacggat tatgtggctc atgtgaccca acatacccag cagcaccatc    13380
tggtaattga ccacgtccga ttactgcatt tcttgtctcc atccacaatg aggtgggcta    13440
caaccattgc ttgtttggtc gccattctcc tggcgtatatg aaatgttctc acagattggg    13500
gtgtttcttg actccgcact cctgcttttg gtggtttttt ttgctgtgta ccggcttgtc    13560
ctggtccttt gtcgatggca acggcaacag ctcgacatac caatacatat ataacttgac    13620
gatatgcgag ctgaacggga ccgcctggtt gtccagccac ttttcttggg cagtcgagac    13680
ctttgtgctt tacccagtcg tgactcatat tctctcactg gttttctca ccacaagcca     13740 ttttttgac gcgctcggtc tcggtgctgt gtccatcaca ggtttttttg gcaaacggta     13800
cgtactcagc agcatctacg gtgcttgtgc tctcgcagcg ttcgtgtgct ttgccatccg    13860
tgctgctaaa aattgcatgg cttgccgcta cgcccgcacc cggttcacta acttcattgt    13920
agacaaccgg gggaggatcc atcggtggag gtctccaata gtggtggaga aattgggtaa    13980
agctgaaatt ggcagcgacc ttgtcaccat caaacatgtc atcctcgaag gggttaaagc    14040
tcaacccttg acaaggactt ctgctgagca atgggaagcc tagatggttt ttgtgatgag    14100
cctcccgctg cgcaaaatct tgtgctagcc tttagcatta catacacacc tgtaatgata    14160 tatgcccta aggtgtcacg cggtcgactc ctagggctgt tgcacatctt gatattcctg     14220
aactgctctt tcactttcgg gtatatgacg tatgtgcatt ttcagtctgc caaccgtgtt    14280
gcactcactt tgggggccgt tgttgccctc ctgtggggcg tttacagctt cacagaatca    14340
tggaagtttg ttacttccag atgcagattg tgctgcctag gccggcggta cattctggcc    14400
cctgcccacc acgtagaaag tgctgcaggt ctccactcaa tcccagcgtc tggtaaccgc    14460
gcatacgctg tgagaaagcc cggactaaca tcagtgaacg gcactctagt accaggactt    14520
```

-continued

```
cggagcctcg tgctgggcgg caaacgagct gttaaacgag gagtggttaa cctcgttaag    14580
tatggccggt agaaaccagg gccagaagaa aagaaaagt acagctccaa tggggaatgg     14640
ccagtcagtc aatcaactgt gccagttgct gggcacaatg atgaagtccc agcgccagcg    14700
acctagggct ggacagacta aaggaaaaa gtctgagaag ccacatttt ccttggctgc     14760 tgaagatgat attcggcacc acctcaccca gactgaacgc tccctctgct tgcaatcgat    14820
ccagactgct ttcaaccaag cgcaggaac tgcgtcgctt tcatccagtg ggaaggtcag     14880
ctttcaggtc gagtttatgt tgccggttgc tcatacagtg cgcttaattc gcgtgacttc    14940
tacatccgct agtcaggatg caagttaatt cgacagtcag gtgaatggcc gcgattggcg    15000
tgtggccttt gagtcaccta ttcaattagg gcgatcacat gggggtcata cttattaggc    15060
aagatccatg tgaccgaaat t                                              15081

<210> SEQ ID NO 2
<211> LENGTH: 15014
<212> TYPE: DNA
<213> ORGANISM: Artificial Sequence
<220> FEATURE:
<223> OTHER INFORMATION: cDNA from Porcine Reproductive and Respiratory
      Syndrome virus

<400> SEQUENCE: 2
atgatgtgta ggggagatac cctacacaca caacactcct ggtgtttgtg tgccttggag       60
gcgtgggtac agccccgccc cacctcttgg cccctgttct agcccaacag gtatccttct      120
ccctcggggc gagtgcgccg cctgctgctc tcttgcagtg ggaaggacct cccgagtatt      180
tccggagagc acctgcttta cgggatctcc acccttaac catgtctggg acgttctccc       240
ggtgcatgtg caccccggct gcccgggtat tttggaacgc cggccaagtc tattgcacac       300
ggtgtctcag tgcgcggcct cttctctctc cagagcttca agacactgat ctcgctgcaa      360
ttggcttgtt ttacaagcca agaaacaagc ttcactggaa ggtccctatt ggcattcctc       420
aagtggagtg caccccatct gggtgctgct ggctctcagc catctttccc atagcgcgca      480
tgacctccgg caaccacaat ttcacccaac gactcataaa ggttgccgat gtgttgtacc       540
gtgatggttg tttgactcgt caacaccttc gtgaacttca gtttatgag cgcggctgca      600 attggtaccc gattacgggg cctgtgcccg gagtggctgt gtatgcgaac tccatgcacg       660
tgtccgacca gccgttccct ggtaccaccc atgtgttaac gaacttgcct ttacctcaac      720
aggcctgtcg gcagccgttc tgtccatttg aggaggctca ttctaacgtg tataggtgga       780
atggactcgc gatttttgtg gattccactt ccgacggccg gtcccgcatg atgtggacac      840
cggggtctag cgactcgact gccttagaag tgctaccacc tggactagga cgtcaagccg       900
aaatcctcac ccggagtttt cctgcccacc accctgttaa cctcgctgac tgggagctca      960
ccgagacccc tgaatccggt ttctccttca gcatgtctca gtcttgtggt taccttgccc     1020
aaaaccctga cgttttgat ggcaagtgct ggctttcctg tttttttgac ctgccgactg      1080
aggtatggcg tcgtgaggag catctggcta gtgccttcgg ttatcaaact aaatggggcg     1140
tgcatggcaa ataccctccag cgcagacttc aaatcaatgg agttcgcgct gtagtcgatc     1200
ctgatggtcc tatccatgtt gaagcgttgt cttgccccca tcttggatc agacacctga      1260 ctctagacgg tgacgtgacc ccaggattcg ttcgcctgat gtctctccgt attgtaccga     1320
acacagaacc ggccactctc ccggtctttc ggtttggagc gcataaatgg tatgcgctg      1380 ccggcaaacg agcccgtgct aggcgtgccg ccagaaatgg gaaggactca gccactgccc    1440
```

```
ccacggccac ccaactgatc cctgcctgtg gaacaaccac ttattccccg ccaacagacg    1500
ggtcttgtgg ctggcatgtt ctcgccgcca tagttaatcg gatgatgcat aatgatttta    1560
catctcctct gactcagtat aacagaccac aggacgattg ggcgtccgat tatgaccttg    1620
ctcaggcaat ccagtgtatg cgactgcctg ctactatagt tcgtggtcgt gcctgcccta    1680
acgccaagta ccttataaaa ctcaatggag tccattggga ggtagaggtg aggtctggaa    1740
tggctccgcg tcttctttct cgtgagtgca ttgttggcgt ctgctctgaa ggctgtatcg    1800
caacgcctta ccctgaaggc gagctacccg agcgtgcact agaggccttg gcggctgctt    1860
acagactacc ttccgactgt gtaagttctg cattgccga cttccttgct gacccacctc    1920
ctcaggaatt ctggaccctc gacaagatgc taacctcccc gtcaccggag cggtccggtt    1980
tctccagttt gtataaatta ctattagagg ttgttccaca aaagtgcgga gctacggagg    2040
gggctttcgt ctatgctgtt gagaggatgt tgaaggactg cccaagctcc aaacaggcaa    2100
tggccctcct ggctaaagtc aaagtcccgt cttcgaaggc cccgtctgtg tccttggacg    2160
agtgtttccc cacggacgtt ccagccgacc ccgagccaac atctcaggaa aagcctcaaa    2220
gttctggcac taccagagtc ctgtgttcgc cgaatacaaa agagtctgag gaggtggcct    2280
tgcaaggcgt tcaggagagc agccacaagg ccgcccactc tgcagtcctt gttgaggaac    2340
ttagcgggaa gcgggcgcag gaggttgccg gcgagctaca ggagttcggc gactgtggct    2400
tggtaatcgg gagtgctcaa gacggcattc tggaggatga gccattggac ttgtcccgat    2460
cagcgttggg ggccacaacg attctcgtga gaaaccaaac acccaacaat tcgggttttg    2520
gcactggtac tcctcctgcc actgttcaag agcccgtctt tacagggctc atgtcttatt    2580
gcgttgagca ttgtaaaacg gagtccgata acagcagttt acctctggat ctgtctaatg    2640
cgcaaacctc ggaccagcct ttaaatctac ccttggctgc ttggccagtg agaaccaccg    2700
catctgaccc tggctgggcc cacggtaggc gtgtgcctgt cttttgtaaag ccccggggca    2760 ctctctccga tggcgattca gtccttctgt ttgggggggct ttccgaatcc agctctgtta    2820
tcgagtttga ccaatcgaaa gacgtcccag tgaccgatgc ccccgtcgac ttgaccaccg    2880
cgaacggagc cctctctggg atcgactccc ttgaatttgc tgaactcaag cgcccgcgct    2940
actccgctca gctttgatt gaccgaggtg gtccactagc cgatgttcat gcaaagataa    3000
agagccgggt atatgaacaa tgccttcagg cttgtgagcc cggcagtcgt gcaaccccag    3060
ccaccaggga ttggctcaat aaaatgtggg aaagggttga tatgaagact tggcgctgta    3120
cttcgcagta ccaagctggt cacattctcg cgtctcttaa atttcttcct gacatgatcc    3180
aagacacgcc acctcctgtt cccaggaaga accgagctag tgatcatgcc gaaccaaaac    3240
gtctggtggc gcagtgggac aagaaattga gtgtggtctc ttccccaaaa ccggttgagc    3300
cagcgcctga ccggaccacc cctttgcctg cggacatcca gcaagagggt gttgcctcct    3360
ccgacagatt aacccgtgcg ccagacctcc ctagtcaagt gagcacgggc gggagttgga    3420
aagaccgcat gcttttcggc gctcgtttcg cggagtccat tggtcagcgc atcacagcac    3480 gggttttga aactttctcc catctcccag cttttgtgct cgcacttttc tcgccgcggg    3540
gcgctatggc ttcaggtgat tggctgtttg caggtattga tttacttgct ctcctgctct    3600
gtcgccctta cccagtactc gggtgcttac ccttactggg tgtcttttct gggtctgtgc    3660
ggcgtgttcg tctgggtgtt tttggttctt ggatggcttt tgctgtattt ttattctcga    3720
ctccacccga cccagtcggt tcttcttgcg gccacgattc gccggagtgt catgctgagc    3780
```

```
ttttggctct tgagcagcgc caactttggg aacctgtgcg cagccttgtt gttggcccct    3840
cgggtctcac gtgcgtcatt tttggtaggt tactcggtgg gtcacgttat ctctggcata    3900
ttctcctacg tttatgcatg cttgcagatt tggcccttc tcttatttat gtggtgtccc    3960
aagggcgttg tcacaagtgt tggggacagt gtataagaac agctcctgca gaagtggctc    4020
ttaacgtctt ccctttttg cgtgccaccc gtgcctctct cgtgtccgtg tgcgaccgat    4080
tccaatcgcc aaaaggtgtt gatcctgtgc acttggcaac cggctggcgt gggtgttggc    4140
gtggtgagag tcctatccac caaccacacc aaaagcccat agcttatgcc aatttagatg    4200
aaaagaaaat atccgccaaa acggtggtcg ctgtcccata tgatcccagt caggccatca    4260
aatgcctaaa agttctacag gcgggaggag ctattgtaga ccagcccacg ccagaggtcg    4320
ttcgcgtgtc tgaaatccct ttctcagccc cattttccc aaatgttccg gtcaacccgg    4380
attgcagggt tgttgtagac tcggacactt ttgtggcagc agtccgctgt ggttactcga    4440
cggcacaatt ggttttgggc caaggcaact tcgccaaatt aaaccaaatc ccccttggga    4500
gttccacctc taccagaacg actggcgggg cttcttacac ccttgctgtg gctcaagtgt    4560
ctgtgtggac cctcgttcat ttcattcttg gtctttggtt cacatcgcct caagtgtgtg    4620
gtcggggac ctccgacccg tggtgttcaa atccttttc atatcccact tatggccccg    4680
gagttgtttg ttcctcacga ctctgtgtgt ctgccgacgg ggtcactcta ccattgtttt    4740
cagccgtggc gcagctctcc ggtagagagg tgggaatttt tgttctggtg ctcgtctcct    4800
tgattgctct agctcatcgt atggctctta aggcagatat gttagtggtc tttttggctt    4860
ttgggggtta cgcctggcct atgagctctt ggttaatctg tttctttcct ttactcctga    4920
agtggatcac tcttcaccct ctcaccatgc tttgggtgca ctcgttttta gtgttttgtc    4980
tgcccgcagc cggcgtcctc tcgctgggga taactggcct cctttgggtg actgccgtt    5040
ttacccaggt agccggaatc atcacacctt atgacatcca tcagtacacc tctgggccgc    5100
gtggtgctgt tgctgtggcc accgcccag aaggcactta catggccgcc gttcggagag    5160
ctgccctaac cgggcgaacc ttaatcttca ctccgtccgc agtcgggtct cttcttgaag    5220
gtgctttcag gactcgcaaa ccctgcccta ataccgtgaa tgttgttggt tcttccctcg    5280
gttccggagg agttttcacc attaatggaa agaaaatcgt cgtcaccgct acccatgtgt    5340
tgaacggcga tgcagccaga gtcactggtg actcttacaa ccgcatgcac actttcaaga    5400
ccaatggtga ttacgcctgg tctgatgcag acaactggca aggtgttgcc cccatggtca    5460
aggttgcaaa ggggtatcgc ggtcgtgcct actggcaaac atcaactggt gttgaacccg    5520
gtattgtcgg ggaaggtttc gccttttgct tcactaactg cggtgactcg gggtcacccg    5580
tcatttcaga gtccggtgac ctcatcggga tccataccgg ttcaaataaa ctgggctctg    5640
gccttgtgac aaccctaac ggggagacct gttccatcaa agaaactaaa ctctctgatc    5700
tttccaagta ttttgctggc ccgagtgtcc ctctcgggga caccaagttg agcccgacca    5760
ttatccctga tgtgacatcc attccgagtg acttagcatc gctcctagct tccgtccctg    5820
taatggaagg tggtctttcg accgttcaac tcttgtgtgt cttctttctc ctctggcgta    5880
tgatgggtca tgcctggaca cctgtcgttg ccgtgggttt cttcttgcta aatgaaattc    5940
ttccagcagt tttagttcgt gccgtgtttt ccttcgcact ctttgtgctc gcgtggctta    6000
ccccttggtc cgcacaggtg ctaatgatta gactcctcac agcgtccctt aaccgcaaca    6060
agcttttcctt agcgttctac gcactcgggg gcatcgtcgg tttggctgct gaaatttgga    6120
ctttcgctgg cagactgcct gatctgtctc aagctctttc gacgtactgc ttcctgccta    6180
```

```
gggtcattgc tgtgaccagt tgtgttccca tcatcatcat tggcgggctt catgctctcg   6240
gtgtgatctt gtggttgttc aaatatcggc acctccacgc catgttggtt ggtgacgggg   6300
ctttctcaag tgcattcttc ctgcggtatt ttgcagaggg taaccttagg aaggggggttt  6360 cgcagtcctg tggcatgagc aacgaatccc taacggctgc cttagcttgt aagttatcac   6420
aggctgacct agatttcctg tcaagcttga cgaacttcaa atgctttgtg tctgcttcaa   6480
acatgaagaa tgctgctggc caatatatcg aagcagcata tgccaaagct ctgcgccgag   6540
agctggcctc cctagtccag gtcgacaaaa tgaaggagt cttgtccaag ttggaagctt    6600
ttgctgagac ggccacccg tcccttgaca caggtgacgt ggttgtgctg ctcgggcaac    6660
atccccatgg atctatcctt gacatcaatg tggggactga agaaaaact gtgtccgtgc    6720 aagagactcg gaacttgggc ggctccaagt tcagtgtctg tactgttgtg tccaacacac   6780
ctgtggacgc cttgaccgat gttccgcttc aaacaccgac tccgctcttc gagaacggcc   6840
cgcgtcaccg ctgtgaggaa gacgatctta agtcgagag aatgaggaaa cattgtgtgt    6900
ctctcggctt ccacaatatc aatggcaaaa tttattgcaa agtctgggat aagtccactg   6960
gtgacacctt ttatacggat gattcccggt atacccaaga ctatgctttt caggacaggt   7020
cagccgacta cagagaccgg gactatgagg gtgtgcaagt cgcctctcaa caaggattcg   7080
acccaaagtc tgaaactcct gttggcactg tcatgatcgg cggcatcatg tataacaaat   7140
acctagttaa aggcagggaa atcttggtcc ttaaacctga caactgccta gaagccgcca   7200
ggctgtccct tgaacaggcc cttgctggga tgggccagac ttgtgatctc acagccaccg   7260
aagtggaaaa gctaaagcgc atcattagtc aactccaagg tctgaccact gaacaagctt   7320
taaactgtta gccgccagcg gcttgacccg ctgtggccgc ggcggcttgg ttgtaactga   7380
aacggcggta aaaattgtaa ataccacag cagaactttc actttaggcc ctttagactt    7440
aaaagtcgct tctgaagtgg aagtaaagaa atcaactgag cagggccatg ctgttgtagc   7500
aaatttaagt tctggtgtcg tcttgatgag acctcaccca ccgtcccttg tcgatgtcct   7560
cctgaaaccc ggacttgaca caacacccgg cattcaacca gggcatggag ccggaacat    7620 gggtgttgac ggttctattt gggattttga aactgcaccc acaaaggcag aacttgaatt   7680
gtccaaacaa ataattcaag catgtgaggt cagacgcgga gacgccccga acctacaact   7740
cccttacaag ctctatcctg ttaggggga ccctgagcgc catgccggtc gtctcaccaa    7800
taccaggttt ggagatttgc cttacaagac tccaggagac accaagtctg ccatccatgc   7860
ggcttgttgt ctgcacccca acggggtccc cgtgtctgat ggcaagtcca cactaggcac   7920
tacccttcaa catggttttg agctttatgt tcccacagtg ccctatagtg ttatggagta   7980
ccttgattca cgctctgata cccctcctat gttcactaaa catggcactt ctaaggctgc   8040
tgcagaagac ctccaaaaat atgatttatc cacccaagga tttgtcctgc ctgggtcct    8100 acgccttgtg cgcagatttg tctttggcca tcggaaa gcaccgccgt tgttcctccc     8160
gtccacttac cctgccaaga actctatggc agggatcaac ggccagagat tcccaacgaa   8220
agacgttcag agtatacctg aaattgatga aatgtgtgcc cgcgccgtta aggaaaattg   8280
gcagaccgtg acgccctgca ccctcaagaa acagttctgt tccaagccca aaccaggac    8340 cattctgggc accaacaact ttattgccct ggctcaccga tcggcgctca gtggcgtcac   8400
ccaagcattt atgaagaagg cttggaagtc cccgattgcc ctggggaaaa acaaattcaa   8460
agagctacat tgcactgttg ctggcaggtg tcttgaggct gatttggcct cctgtgatcg   8520
```

```
tagcaccccg gccatcgtga ggtggtttgc tgccaacctc ctgtacgagc ttgcagggtg    8580
tgaagagtac ttgcctagct atgtactcaa ctgctgccac gacctcgtgg caacacagga    8640
tggtgccttc acaaaacgcg gtggtttgtc atccggtgac cctgttacca gtgtgtcaaa    8700
caccatatat tcactggtga tctatgccca gcacatggtt ttgtcagcct taaaaatggg    8760
tcatgagatt ggtcttaagt ttctcgagga acagctcaaa ttcgaagacc tcctcgaagt    8820
ccagcccatg ttagtgtact ctgacgacct agtcttgtac gccgaaaggc ccaccttccc    8880
taattaccac tggtgggtcg aacaccttga cctaatgctg ggtttcaaaa cggacccgaa    8940
gaaaactgta ataactgata agcccagctt cctcggctgt aaaattgaag cagggcggca    9000
gctagttccc aatcgcgacc gtatcctagc cgctcttgca taccacatga aggcgcaaaa    9060
cgcctcagaa tattatgcat ctgctgctgc gatcctaatg gattcgtgtg cttgcattga    9120
ccacgatcct gagtggtatg aggacctcat ttgtggtatt gcccggtgcg ctcgccaaga    9180
tggctatagt tttccaggcc cggcattttt catgtcgatg tgggaaaaac taaagagcca    9240
caacgaaggg aaaaaattcc gccactgcgg tatctgtgat gccatggccg atcatgcatc    9300
tgcctgtggg cttgatttgt gtttgtttca ttcgcatttt caccagcatt gtccagtcac    9360
tctgaactgc ggtcaccgtg ccggcgcaaa ggaatgtccg cagtgccagt cgccagttgg    9420
ggttagcaaa tcccctctcg acactgtgct agaacaaatt ccatacaaac cccctcgtac    9480
tgtcattatg aaggtgagtg atagaacgac tgtcctcgac ccgggcaggt accagtcccg    9540
tcgtggtctt gttgctgtta agaggggcat tgcaggcaat gaagttgatc ttcctgatgg    9600
agactaccaa gtggtgcctc tcttaccaac ttgcaaagat ataaacatgg taaaggtagc    9660
ttgcaatgta ctgctgagta agttcatagt aggaccacca ggttccggaa aaaccacttg    9720
gttactgagt caagtccagg acgacgatgt catttacaca cccacccatc agaccatgtt    9780
tgatatagtc agtgctctca aggtttgcag gtattctatt ccaggggcct ctgggctccc    9840 cttttccacca cctgccaggt ctgggccgtg ggtcaggctt gttgccagcg ggcacacccc    9900
cggccgagtg tcatacctcg atgaggccgg gtactgcaac catctggaca ttcttaggtt    9960
gctttccaaa acaccccttg tgtgtctggg tgaccttcag caacttcacc ccgtcggctt    10020
taattcctac tgctatgtgt ttgatcagat gcctcaaaag cagctgacca ccatttacag    10080
gtttggcccc aacatctgtg cagccatcca gccttgttac agggaaaaac ttgaatccaa    10140
ggccaggaac accaggatag ttttttactac acggcctgta gctttcgggc aggtcctgac    10200
accataccac aaagatcgca tcggttcagc gataaccata gattcgtctc aggggccac    10260 ttttgacatt gtgactttgc atttaccatc gccaaagtcc ctgaataaat cccgggcact    10320
tgtggccatc actcgggcaa ggcacgggtt gttcatctac gaccctcaca atcagcttca    10380
ggagtttttc aacctagctc ctgagcgtac tgattgtaac cttgtgttta accgtgggga    10440
tgagctagta gtcctgaact cggacaatgc agtcacaacc gtggcgaaag ccctagaggc    10500
aggcccatct cggtttcgag tatctgatcc gaggtgcaag tctctcttgg ccgcttgctc    10560
ggccagccta gaagggagct gcatgccgct gccgcaagtg cgcacaatc tggggttcta    10620 cttctcccca gatagcccag catttgcacc cctgccgaaa gaactagcgc cacattggcc    10680
ggtggtcact catcagaaca accgggcatg gcctgaccga cttgttgcta gcatgcgtcc    10740
aatcgatgcc cgttacagca agccaatggt cggcgctggg tatgtggtcg ggccatccac    10800
ttttctcggc accccggcg tggtgtcata ttatctgacg ctgtacgtca ggggtgagcc    10860
ccaggccttg ccagaaacac tcgtgtcaac ggggcgcata gccacagact gtcgagaata    10920
```

```
tctcgacgcc gctgaggaag aggtagcaaa agaactaccc cacgcattca ttggtgatgt    10980
caagggtacc acggttgggg ggtgtcatca catcacatca aaacacctac ctaggttcct    11040
acctaaggat tctgttgccg tggttggagt aagttcaccc ggcaaggctg ctaaagccgt    11100
gtgcacccct actgatgtgt acctaccgga actccggcca tatttgcaac ctgagacagc    11160
gtcaaagtgc tggaagctca aactggactt cagggatgtc cgtctgatgg tctggaaagg    11220
ggcaaccgcc tattttcaat tagaagggct cacatggtcg gcgctgcccg actatgccag    11280
gtttattcag ctgcctaagg aagccgtggt gtacatcgat ccgtgtatag gaccggcaac    11340
agccaaccgc aaagtcgtgc gaaccacaga ctggcgggct gacctggcag tgacaccgta    11400
tgattacggt gctcagtata ttttgacaac agcctggttc gaagacctcg gccacagtg    11460 gaaaattctg gggttgcaac cttttaggcg atcgcttggc tttgagaaca ccgaagattg    11520
ggcaatcctt gcacgccgta tggatgacgg caaagattac atcgactaca actggaattg    11580
tgttcaaaac cgtccacttg ctatccacgg gcgcgctcgt gaccacacat atcacttcgc    11640
cctcggcaca gagttgcagg tggaactggg caaaccccgg ctgccgccgg agcaagtgca    11700
gtgaacccgg agtgatgcaa tggggtcact gtggagtaaa atcagccagt tgttcgtgga    11760
cgctttcact gagttcctcg ttagtgtggt tgacattgtc attttccttg ccatactgtt    11820
tgggttcaca gtcgccgggt ggctactggt cttccttttc agaatggttt gctccgcgat    11880
tctccgttcg cgctctgcca tttactctcc cgaactatcg aaggtcctat gaaggcctgc    11940
tacccaactg caggccagat gtcccacaat tcgcattcaa gcatccactg ggcttgcttt    12000
ggcatatgcg agtttcccat ttgattgatg aaatggtctc ccgtcgtatt taccagacta    12060
tggaacattc aggtcaagcc gcttggaagc aagtggtcgc tgaggctacc ctcacaaaac    12120
tatcaaggct tgacgtagtc actcatttcc aacatctggc cgcggtggag gcggattctt    12180
gccgcttcct cagctcacga cttgcaatgt tgaaaaacct tgccgttggc aatgtgagct    12240
tgcagtataa caccacattg gacagagttg agctcgtctt ccctacgccg ggttcgagac    12300
ccaagttgac tgatttcaga caatggctca tcagtgttca cgcttccatc ttctcttctg    12360
tagcttcgtc tgtcaccttg ttcatagtgc tctggcttcg aattccagcc ttacgctatg    12420
tttttggttt ccattggccc acggtaatac atcattcgag ctaaccatca actatacaat    12480
atgtatgccc tgtcttaccc gccaagcggc tagtcagagg ctcgagcctg ccgcaacat    12540 gtggtgtaga atagggtacg acagctgtga agaacgtgac catgatgagc tgtcaatgtc    12600
catcccgtct gggtacgaca acctcaaact cgagggttat tacgcttggc tggcattctt    12660
gtccttctcc tacgccgctc aattccatcc agaattgttc ggaataggga atgtgtcacg    12720
cgttttcgtg gacaaacaac accaagccat ttgtgctgtg catgacggac aaaattccac    12780
catatccgct gagtacaaca tttctgcatt gtacgcggca tactaccacc accaagtaga    12840
cgggggcaac tggtttcatc tagaatggct gcggccattc ttttcttcct ggctggtgct    12900
caatatttca tggtttctga ggcgttcgcc tgcaagccct gcttctcggc gcatctatca    12960
gatgttaaga ccaacacaac tgcggctgcc ggtttcatgg tccttcagaa cattgaatgc    13020
cttcgacacg gagcctcaac aacgcaaaat ggccttcccc ttcggaagcc gtcgcaatgt    13080
cgtgaagccg ttggcacccc tcagtacatc acaattacgg cgaatgtgac cgatgaatca    13140
tatttgtaca acgctgactt gctgatgctt tctgcgtgcc tcttttacgc ctctgaaatg    13200
agcgagaaag gcttcaaagt catcttcggg aacgtttctg gcgttgtctc tgcctgcgtt    13260
```

```
aattttacag actatgtggc ccatgtgact caacacaccc agcagcatca cctggtaatt    13320
gatcacattc gattgcttca cttcttgtca ccgtctgcaa tgaggtgggc tacaaccatt    13380
gcttgcttgc tcgccattct cttggcgata tgagatgttc tcacaaactg gagccttcct    13440
cgactccgca ctcttgctcc tggtggcttt ttttgctgtg taccggcttg ttctggtcct    13500
ttgccgatgg caacggcaac agcccgacat accaatacat ataaacttg acgatatgcg    13560 agctgaatgg gaccgagtgg ttgtctaacc atttttaattg ggccgtcgaa acctttgtgc    13620
tctacccagt cgcaactcac attatttcac tgggttttct tacaacaagt catttccttg    13680
atgcgctcgg tctcggcgct gtgtccgtca ccggatttta caacaaccgg tatgtgctaa    13740
gcagtgtcta ctgcgcctgt gcttttgcag cactcgtgtg ctttgtcatc cgtgccgcta    13800
aaaattgcat ggcttgccgc tatgcccgca cccggtttac taatttcatc gtggacaacc    13860
gggggaggat ccaccgatgg aagtctccaa tagtggtgga gaagttgggg aaagctgagg    13920
ttggtagcga ccttgtcacc atcaaacatg ttgtccttga aggggttaaa gctcaacctt    13980
tgacgaggac ttcggctgag caatgggaag cttagacaat ttttgcggtg atcctgccgc    14040
cgtacaaaag cttgtgctgg cctttagcat tacatataca cctataatga tatcgccct    14100 taaggtgtca cgcggccgac tcttaggact attgcacatc ctaatattct tgaattgttc    14160
tttcacattt gggtatatga cttatgcgca ttttcaatcc accagtcgtg tcgcgcttgc    14220
tctgggggct gttgtcaccc tcctgtgggg catttacagt cttacagagt catggaagtt    14280
tgtcgcttcc agatgcagaa tgtgttgtct aggccggcga tacatcctgg cccctgccca    14340
tcacgtagaa agtaccgcag gtctccattc aatcccagcg tttggcaacc gagcatacgc    14400
tgtgagaaag cccggactaa catcagtgaa cggcactctg gtaccaggac ttcggagcct    14460
cgtgctgggc ggcaaacgag ctgttaaacg aggagtggtt aacctcgtca agtatggccg    14520
gtaaaagcca gagccagaag aaaaagaaaa atacagctcc aatggggaat ggccagccag    14580
tcaatcaact gtgccaattg ctgggttcga tgataaggtc ccagcgccag caacctagga    14640
gaggacaggc gaaaaaaaga aagcctgata agccacattt tcccctagct gctgaagatg    14700
acattcggca ccacctcacc cagactgaac gttccctctg cttgcaatcg atccaaacgg    14760
cttttaacca aggcgcaggt gttgcgtcgc tttcatccag cgggaaggtc agttttcagg    14820
ttgagttcat gttgccggtt gctcatacag tgcgcctaat tcgcgtgact tctgcatccg    14880
ctagtcagaa tgtagattaa tttgacagtc aggtgaatga ccacgattga cgtgtggcct    14940
ctaagtcacc tattcaatta gggcgatcac atggggtca aacttaattg ggcgagaacc    15000
atgtgaccga aatt                                                      15014
```

<210> SEQ ID NO 3
<211> LENGTH: 14876
<212> TYPE: DNA
<213> ORGANISM: Artificial Sequence
<220> FEATURE:
<223> OTHER INFORMATION: cDNA from Porcine Reproductive and Respiratory
      Syndrome virus

<400> SEQUENCE: 3

```
atgatgtgta gggtatcccc cttgttttg cagcactcct agtgtttgtg tgcctcggag      60
gcgtgggtac agccccgccc cacctcttgg cccctgtcct aacccgacag gtaccttct    120 ccctcggggc gagcgcgccg cctgctgctt tcttgcggcg ggaaggacct cccgagtatt    180
tctggagagc acctgcttta cgggatctcc acccttaac catgtctggg atgttctccc    240
```

```
ggtgcatgtg caccccggct gctcgggtgt tttggagtgc cggtcaagtc tattgcacac    300
ggtgtctcag tgcacggcct cttctccctc cagggctgca agacactgac ctcgcagcaa    360
ttggcttgtt ctacaagccc aaagataaac ttcactggaa agttcctatc ggcatccctc    420
aggtggagtg tactccgtct ggatgctgct ggctctcggc catcttcccc ttggcgcgca    480
tgacctccgg caaccacaac ttttctcagc gactcataaa agttgccgaa gtgttgtacc    540
gtgatggctg tttgactccc cgacaccttc gtgagcttca agtttacgag cgtggttgca    600
gttggtaccc gatcaccggg cccgtgcccg gagtaggtgt gtacgcgaac tccatgcacg    660
tgtccgatca atcgtttcct ggtgccactc atgtgctgac gaacttgcct ctacctcagc    720
aagcttgtcg acagcctttc tgtccattcg atgaggcccg ctctgacgtg tacaagtgga    780
acgaatttgt ggttttcgtg gattcctcct ccggcggtca attacgcatg atgtggatgc    840
cgggatccga tgattcggtc gccattgaag cattatcgcc tgagttggaa cgtcaggttg    900
aaatccttgt tcggagtttc cctgccacc accctgttaa cattgccgac tgggagcttg    960
ctgagtcccc ggagcacggt ttttccttcg gcacgtctca tcctagtggt taccttaccc   1020
gagacccttg gggttttgat ggcaaatgtt ggctctcttg cttcttgggc ctcccgacta   1080
gagttcagca tcatgaggag tacctagccg acgccttcgg ttaccaaacc aagtggggcg   1140
tgcacggtag gtatcttcag cgcaggcttc aagtcaacgg tgtccgtgct gtggttgatc   1200
ctgacggccc catccacgtt gaagcgctgt cttaccccca gtcttggatc aggcacctga   1260
cttttgacga tgatgttacc ccaggattcg ttcgcctgat gtctcttcgc attgtgccga   1320
atacagaacc taccactctc ccaattttcc ggtttgggc gcataaatgg tatggagcag   1380
ctggcaaacg agctcgcgcc aagcgtgctg ccaaaaacaa gggggattcg aattccaccc   1440
ccgaagtcgc ccgagtggct tctaccagtg aggttgttac ctattcccca ccggcagacg   1500
ggtcttgtgg ctggcatgtt gttgccgcca tgatgaacca catgatgaac ggtaaactca   1560
cgtccctttt gactccgtac aacagaccag aggacgactg ggcttctgat tatgatcttg   1620
tcaagataat tcaatatttg caactgcccg caaccgtagt tcgggcccgt acttgtccca   1680
acgctaagta ccttgtcaaa ctcaatgggg tccattggga agttgagatg aggccagaag   1740
tagctccttg ctctctttcc cgcgaatgtg tggttggtgt ctgttctgag ggctgtgttg   1800
cgtcgcctct tccagaaggg gggctgcctg accgcgcact tgaggcctg gcgtccgctt   1860 acagattgcc ttccgactgc gttggtgatg ctgttgctga cttcctctcc agcccgccct   1920
ctcaagaatc ctggaccctc gataaaatgt tgacctcccc atcaccagag cagtccggtt   1980
tttctagctt gtacaaactg ctactggagg ttgttccgca gaagtgcgga gccacggagg   2040
gggccttcgt ctatgctgtt gagaggatgc tgaaagattg tccgagcccc aaacaggcca   2100
tggccctttt gggaaaaatc aaaatcccat cctcaaaagc ctcgtccgtg tccttagacg   2160
agtgctttcc cactgatgtt ttgcaagagg gtaaccacag gacctccac cccgtggctc   2220 ctgctgatgg acttgacaaa cagcaagcac cgttggttga ggatgaacaa ttaggattcg   2280
gtggtcacga ttcggccgtt gcggcggtca gtggcaatca ggagagtgaa ccgttggacc   2340
tttcccgatc ggcaccagtt gtaacaacga ccttcgtcga agggcgagtg cccggcgacc   2400
cgggcccctg caccagcgac cgctccgctg ttgttcaaga gttagttgag cgatgtgacg   2460
cggagtcaaa tgacggcagt ttgccctgg atgtgactaa agtgcaaacc cccaatcaac   2520
ctctggatct atctctagct gcttggccag tgaagaccac tgcatctgac cccggtgggg   2580
ttgacggtag acgcgaaccc gtcttcgtca agcctcgcgg tgctttctct gacagtgagt   2640
```

```
cggtcttccg gtttggagga gtttctgaga ccggccctgt catcgggttt gatcgggtaa    2700
aagaaattcc ggcggctgac accccccatcg acttaacaat ctcaaaagag actctttccg    2760
gggcagaccc ctctgagttc gccgcactta agcgcccgcg tttctccgct caagccttga    2820
ttgaccgagg tggcccactt gctgatgcct gtgcaaagat aaagaatcga gtgtatgagc    2880
ggtgcctcca ggcttgcgaa cctggcagtc gtgcgactcc agccacaaag gagtggctcg    2940
acaagatgtg ggaaagggtc gacatgaaga cttggcattg tacctcgcag ttccaaacag    3000
tctatattct cgggccccctt aaattcctat cagatatgat tagtgacacg ccacctcctg    3060
tccctaggag ggatcggttt agtgacagtg ccagcttgaa acaattagcg gcacagtggg    3120
atgagaaatt gaacacagtc ccccccaag ggccggttga gccggggctt agtcgagccg    3180 cccctcgcc tgcgaatgcc cagcgagaag gcatcaaccc ctccgatgag ccaccccaaa    3240
cgccgaaccc ctctggacaa actgttgctg atggggtgt caaaagactt gtgtccttcg    3300
gcgtccgcct tgtagggtcc accagccagc gccttatgac atgggttttt gaaatttact    3360
cccatctccc agcttttatg ctcacactat tctcgccgcg gggctctatg gttgcaggtg    3420
attggttgtt tgcaggtgtt gtgttacttg ctctcttgtt ttgtcgttct tacccagtgc    3480
tcggatgcct tcccttattg ggtgtctttt ctggttctgt acggtgtgtt cgtctgggcg    3540
tttttggttc ttggatggct tttgctgtat ttttattctc aactccaacc aacccagtcg    3600
gttcttcttg tgaccacgat tcgccggagt gtcatgctga gcttttggct cttgagcagc    3660
gccaactttg ggaacctgtg cgcggccttt tggtggggcc ctcgggcctc ctatgcgtca    3720
ttcttggcaa gctactcggt gggtcacgtt atctctggca tgttctctta cgtttatgca    3780
tgcttgcgga tttggccttt tctcttattt atgtggtgtc ccaagggcgt tgtcacaagt    3840
gttggggaaa atgtataagg acggctccag ccgaggtggc cctcaacata ttccctttct    3900
cacgtgccac ccgtgcttcc cttgtatcct tgtgcgatcg gttccaagcg ccaaaagggg    3960
ttgaccccgt acacttggca acagggtggc gcgggtgttg gcgcggtgag agccctattc    4020
atcaggcgca ccagaaacct atagcttatg ccaacttgga tgagaagaaa atatccgccc    4080
aaacagtggt tgctgtccct tatgaccccca gtcaggccgt caaatgtttg aaagttctgc    4140
aggcgggggg ggccatcgta gatcagcccg tacctgaagt ggtccgtgtg tccgagatcc    4200 cttttcggc tccattcttc ccaaaagttc cagtcaaccc agattgcagg gttgtggtgg    4260
attcggacac tttcgtggct gcagtccgct gtggttactc gacaacgcaa ctggtcttgg    4320
gtcaaggcaa ctttgccaag ttgaacaaca cccctctcaa gaattccgtt tccaccaaga    4380
cgattggagg ggcctcttac acccttgccg tggttcaggt gtccgtgtgg actcttgttc    4440
attttgtaat cggtctttgg ttaatgtcgc ctcaagtgtg tggccgaggg acctctgacc    4500
cttggtgctc aaatcctttt tcatatccta cttatggtcc cggggttgtg tgttcctccc    4560
ggctttgtgt gtctgccgat ggagtcactc taccattgtt ttcagctgtg gcccaactgt    4620
ctggtagaga ggttgggatc tttattttgg tgtttgtctc tttaatcgcc ttggctaacc    4680
gcctagctct taagtctgac atattagtgg tatttctggc actttgtgct tatgcttggc    4740
ccatgagctc ctggctaatc tgtttctttc ctatactctt gaggtggatc accctccacc    4800
ctcttaccat gctttgggtg cattcgttct tagtattctg tttgccagcc gccggtgtcc    4860
tgtcaatagg ggttactggc tttctttggg cgattggtcg tttcacacaa gtcgccggaa    4920
ttatcacacc ttatgacatt catcaataca cctccgggcc acgcggtgcg gctgctgtag    4980
```

```
caacggcccc agagggtact tacatggcag ccgtccggag ggccgccctg accggacgga    5040
ctttaattt tacccatct gcagttgggt ctctccttga gggcgctttc aggacccaca    5100
agccctgtct caacaccgta aatgtcgtag gttcttccct cggttctgga ggggtcttca    5160
ctatcgacgg cagaaagact gtcattactg ctgcccatgt attgaacggt gacaccgcta    5220
gggtcaccgg cgactcctat aatcgcatgc acacttttaa aaccaatggt gattatgcct    5280
ggtcccatgc tgacgattgg cagggcccctt ctcccatagt caaagtcgcg aagaggtatc    5340
gcggccgcgc ttactggcaa acatcgactg gtgtcgaacc aggcatcatc ggggaagggt    5400
tcgctttctg tttcaccaat tgtggcgatt caggttcacc tgtcatctct gaagctggcg    5460
acctcatcgg gatccatact ggttcaaata aacttggatc tggacttgtg accgcccctg    5520
acggggaaac ctgctccatc aaagagacca aactttctga cctatctagg tactttgcag    5580
gtccaagcgt ccctctcgga gacataaagt tgagtccagc tatcatccct gatgtggcct    5640
ctgtcccgag tgacttggca tcacttcttg cttccgtgcc tgtgatggag ggcggccttt    5700
cgaccgttca acttctgtgt gttttcttcc ttctttggcg catgatgggc catgcctgga    5760
cccccgtcgt tgctgtgggc ttcttttttgc tgaacgaaat cctcccagca gtcttagtcc    5820
gcgctgtgtt ttcttttgca ctctttgtgc ttgcatgggc caccccctgg tctgcacagg    5880
tgctgatgat cagactcctc acggcagcac tcaatcgtaa caggttttcc ttggtctttt    5940
acgcactcgg gggcgtcgtc ggcttggctg ctgagattgg gacttttgct ggtaaactga    6000
ctgaactgtc ccaggccttg tccacatact gcttcttacc tagggttgct gccatgacta    6060
gttgcgttcc catcatcatc atcggtgggc tccacaccct tggtgtgatt ctgtggctgt    6120
tcaaataccg tggtctccac aacatgctgg tcggtgatgg gagtttctca agcgccttct    6180
ttctgcggta ttttgcagaa ggcaatctaa ggaaaggcgt ttcgcagtct tgtggcatga    6240
gtaatgaatc tttaacggct gccctggcct gtaagttgtc acaggctgac ctagattttc    6300
tgtccagcct gacgaacttc aagtgctttg tgtctgcctc aaacatgaaa aatgctgctg    6360
gccagtacat tgaagcagcg tacgccaagg ccctgcgtca ggagttagct tctctagtcc    6420
aagttgataa aatgaaagga gtcctgtcca agctcgaagc ttttgctgaa acagcaaccc    6480
catccctgga cacaggagat gtgattgttc tactcgggca acatcctcac gggtccgttc    6540
ttgacatcaa tgttgggact gaaaggaaga ccgtgtcagt gcaagagacc cggagcctag    6600
gcgggtctaa attcagtgtc tgcaccgttg tgtccaacac accagtcgac accttgaccg    6660
gcatcccact tcaaacgccg accccactct ttgaaaatgg cccgcgccac cgcggtgagg    6720
atgacgacct taaagttgag aggatgaaga acactgcgt ctccctcggt ttccataaca    6780
tcaatggcaa aatttactgc aaggtctggg acaagtccac cggagacacc ttctacacgg    6840
atgattcccg gtatacccaa gactatgcct ttcaggacag atcggctgat tacagagaca    6900
gagattatga gggtgtgcaa actgcccctc aacaaggatt tgacccgatg tctgaaaccc    6960
ccgttggtat tatcgtgatt ggcggtgtca cgtacaacag gtacttagct aaaggcaagg    7020
aggttttgat ccccaaacct gataaccatc tcgaggccgc taggcttttcc ctcgagcaag    7080
ccctcgctgg gatgggccaa acttgtgatc ttacggctgt cgaggtggag aagttgaagc    7140
gcattatcag tcaactccaa ggcttgacca ctgagcaggc tttaaactgt tagccgccag    7200
cggcttgacc cgctgtggcc gcggcggctt agttgtgaca gaaacggcgg tgaagattgt    7260
gaaataccac agtagaactt tcaccttggg tcctctagac ttgaaagtca cttctgaggc    7320
ggaagtaaag aaatcaactg agcagggcca cgctgttgtg gcaaacttat gctccggtgt    7380
```

```
cgtcttaatg aggcctcacc cgccatctct cgttgatgta cttctggtgc ccggacttga    7440
cacagcaccc ggcattcaac cagggcatgg ggccggaaac atgggtgtga acggtgctat    7500
ttgggatttc gagactgcac ccactaaggc agagctcgag ttgtccaagc agataatcca    7560
ggcctgtgag gttaggcgcg gggacgcccc gaatctccag ctcctctaca agctttaccc    7620
tgttaggggg gatcctgaac ggcgcaatgg ctgtctcatc aacaccaggt tcggagattt    7680
gccctataag actcctcaag acaccaagtc cgcgatccac gcggcttgct gcctgcaccc    7740
cgatggggcc ccggtgtctg atggcaagtc tacattaggt tccaccctcc aacgtggttt    7800
tgagctttac gtcccacag tgccttacag tgttttggag taccttgatt cacgccctga    7860
cacccccctc atgtgtacca acatggcac ttctgaggct gctgcggagg acctccaaaa    7920
atacaacctg tccactcaag gatttgtcct gcctggagtc cttcgtttag ttcgcagatt    7980
cattttcggc catatcggaa aggcgccacc gttgtacctc ccatcaacct atcctgccaa    8040
aaactccatg gcagggatta atggccaaag gtttccgaca aaggatgtcc agagcatacc    8100
tgaaattgac gaaatgtgcg ctcgcgccgt caaagagaat tggcagactg tgacgccttg    8160
caccctcaag aagcagtact gttccaaacc caaaactaga accatcctgg gcactaacaa    8220
cttcattgcc ttggcgcaca gatcagcact cagtggtgtc acccatgcgt tcatgaagaa    8280
agcctggaaa tctccaattg ccttgggaaa gaacaaattt aaggagttgc actgtactgt    8340
cgccggcagg tgccttgagg ccgacttggc ttcctgtgat cgcagcaccc cagccatcgt    8400
aaggtggttt actgctaatc ttttgtatga acttgcaggg tgtgaggagt acttgcctag    8460
ctatgtgctc aactgctgtc atgatctcgt ggcaactcag gatggcgctt ttacaaagcg    8520
tggtggtctg tcgtctgggg accccgttac cagtgtgtcc aacactgtgt actcactggt    8580
gatttacgcc cagcacatgg tgctgtcagc actgaagatg ggccacgaaa ttggcctcaa    8640
gttcctcgag gaacaactca gttcgagga cttattgaa attcagccca tgttggtgta    8700
ctctgatgac ctcgtcttgt atgctgagaa gcccaccttt cctaattacc actggtgggt    8760
cgagcacctt gatttgatgc tgggtttcaa gacggaccca aaaaaaacta ttataactga    8820
caaacccagc tttctcggct gcagaattga ggcagggcgg cagttagtcc ccaatcgcga    8880
ccgcatcctg ccgcccttg cataccacat gaaagcgcag aacgcttcag aatattacgc    8940
gtctgctgcc gcaatcctga tggattcatg tgcttgtatt gactatgacc ctgagtggta    9000
tgaggatctc atctgcggca ttgcccggtg cgctcgtcaa gatggctata gttttccagg    9060
cccgccattt tttatgtcca tgtgggaaaa gctgaaaagt cacaatgaag ggaaaaaatt    9120
ccgccactgc ggtatctgtg atgccaaggc tgaccatgcg tccgcctgcg ggcttgattt    9180
gtgtttgttc cattctcact ttcatcagca ttgcccagtc atgcttagct gtggtcatca    9240
cgctggttta aaagaatgcc cgcagtgtca gtcaccagtc ggggctggca agtcccctct    9300
tgacaccgtg ttgcaacaaa tcccgtataa accaccccga actgtcataa tgaaggtgaa    9360
cagtaaaaca acagcccttg acccggggag gtatcagtcc cgtcggggtc ttgtcgcagt    9420 caagaggga attgcaggca atgaggttga tctcgctgac ggggactacc aggtggtacc    9480
cctcctgccg acctgcagag acataaatat ggtgaaggtg gcttgcaatg tactactcag    9540
caaattcata gtagggccac ccggctccgg aaagactacc tggttgctga accaagtcca    9600
agatgatgat gttatctata cacccaccca tcagaccatg tttgatatag tcagtgctct    9660
taaggtttgc aggtattcaa tcccaggagc ctcaggactc cctttccac cgcctgccag    9720
```

```
atccggacca tgggtcaggc ttatcgccag cgggcacatc cctggccggg tctcatacct    9780
tgacgaggcc gggtattgca atcatctgga catcctcaga ctgctttcca aaacacccct    9840
cgtgtgtttg ggcgatcttc aacaacttca ccctgtcggc tttgattcct gttgttatgt    9900
ttttaatcag atgccacaca aacagctgac caccatttac aggttcggcc ctaatatctg    9960
tgccgccatc cagccttgtt acagggagaa gcttgaatcc aaggcaagaa acaccagggt   10020
ggttttcacc actcaacctg tggcctatgg tcaagtgctg acaccatttc acaaggatcg   10080
cgtagactca gccataacca tagattcatc tcagggtgcc acctttgacg tcgtgacgtt   10140
acacttgccg acgccaaaat ccctgaacaa atcccgagca cttgtggcta tcacccgggc   10200
gaggcatggg ctgttcatct atgatcctca taaccaactt caggagttct tcaacctaac   10260
ccctgagcgc acggattgca accttgtgtt caaccgtggg gatgaactgg tcgtcctgga   10320
tccagataat gcagtcacga ccgtagccaa ggccctgggg gccggccgt ctcaattccg    10380
ggtgtccgat ccgaggtgca agtccctctt ggccgcttgc tcagtcagcc tggaaggtgg   10440
ctgcatgccg ctgccgcagg tggcccataa tttggggttt tatttctccc cagacagtcc   10500
ggcgtttgca cctctgccaa agaactggc accacattgg ccggtggtta cctgccagaa    10560
caaccgggca tggcctgatc gactcgttgc cagcatgcgc ccgattgacg cccgttacag   10620
caagcctatg gttggtgcgg ggtatgttgt tgggccgtcc acctttcttg gaacccctgg   10680
tgtagtgtca tattacctca cactgtacat caagggtgag ccccaagccc taccagaaac   10740
actcgtttcg acagggcgta tagccacaga ctgccgggaa taccttgata cagctgaaga   10800
agaagcagct aaagaactcc ctcatgcttt cataggtgat gtcaaaggca ccacagtagg   10860
ggggtgtcac cacattacat caaaatactt acccaggtcc ctacccaagg actctgttgc   10920
agtggttggg gtgagctcac ctggcaaggc tgccaaagcg gtgtgcactc tcactgatgt   10980
gtacctccct gaccttcggc cgtatctgca accagagaca gcatcaaaat gctggaaact   11040
caaattggac ttcagggacg tcagattgat ggttttggaa ggggccactg cctatttcca   11100
attggaagga ctcacatggt cggcattacc cgactatgcc aggttcattc agctacccaa   11160
agatgccgta gtatacattg acccgtgtat aggaccggca acggccaacc gcaaggttgt   11220
gcgaaccact gactggcgag ctgacctggc ggtaacaccg tatgattacg gtgcccagac   11280
tattctgaca acagcctggt tcgaggacct cggaccacaa tggaaaatcc tggggctgca   11340
gccctttaag cgggcatttg gcctcgaaaa cactgaagac tgggcaatcc tcgcacgccg   11400
tatgagtgac ggcagagatt acaccgacta caactggact tgtgttcgag aacgcccgca   11460
cgctatctac gggcgcgctc gtgaccacac gtatcatttc gcccctggca cagaattgca   11520
ggtagaactg gcaaacccc ggctgccgct tgagtgagta ctgcggctcg aaagccatgc    11580
aatgggttca ctgtggagta agatcactca gctgtttgtg gatgccttca ctgaattcct   11640
tgttagtgtg gttgacattg ttatcttcct tgccatacta ttcgggttca cagtcgcagg   11700
atggttactg gtctttctac tcagagtggt ttgctccgcg attctccgtt cgcgcactgc   11760
cattcactct cccgaattat cgaaggtcct atgaaggcct gctgcccaat tgcagaccgg   11820
atgttccaca attcgcaatc aagcatccat tgggcatcct ttggcacatg cgagtttccc   11880
atctaattga tgaaatggtc tctcgtcgtg tctaccaaac catggaacat tcaggccaag   11940
cggcctggaa gcaggcagtt gctgaagcca cacttacaaa gctatcgcag cttgacatgg   12000
tcacccactt ccagcatctt gccgcagtgg aagcggattc ttgtcgcttc ctcagttcgc   12060
gactcgtgat gctaaaaaac cttgctgtcg gcaatgtaag tctgctgtac aataccacat   12120
```

```
tggaccgtgt tgaactcatt ttccccacgc caggtgcgag gcccaaattg accgatttca   12180
gacaatggct catcagtgtt catgcttcta ttttctcttc tgtagcttcg tcagtcactt   12240
tgtttgtagt gctttggctt cgaattccag tgctacgcta tgtttttggt ttccattggc   12300
ccacggcaac acgtcgttcg aactgaccat caattacacc gtatgcaagc cttgcattac   12360
tagacaagct gctgcccaac gactcgagcc tggtcgtaac atgtggtgca aaattgggta   12420
cgatcactgt gaagagcgtg atcacgatga gttgtcaatg ccatcccgt ccgggtacga    12480
caacactaaa cttgaaggct attatgcttg gcttgccttc ttgtcttttt cttatgcggc   12540
ccagtttcat ccagagctgt ttggaatagg aatgtgtca cacgttttcg tggacaagca    12600
gcatcaattc atctgtgccg agcatgatgg gcaaaattca accatacccca acccacacaa  12660
catctctgca ttgtatgcgg tgtattatca ccaccaagtg gacggggca actggttcca    12720
tctagaatgg ctgcggccat tcttctcctc ctggttggtg ctcaatattt catggtttct   12780
gaggcgttcg cctgcaagcc ctgtttctcg acgcatctat cagatattaa aaccaacaca   12840
accgcggctg ccggtttcat ggtccttcaa gacattagct gttcccaacc ccatgagaga   12900
tcgggcacgc ggtcgtccgt tcgcgggaag ccatcccaat gtcgtacagc catcggcacc   12960
cccctgtaca tcacgctaac ggcgaatgtg actgatgaat cttatttgta caatgctgat   13020
ttattgatgc tttctgcttg cctgttttac gcctcggaaa tgagtgagaa gggcttcaaa   13080
gtcatttttg gaaacgtctc tggtgttgtt ccgcgtgcg tcaatttcac agactatgtt    13140
acccatgtga ctcagcatac ccaacagcat catctggtag tcaaccatat ccggttgctg   13200
cactttatga caccgtcaac gatgaggtgg gccacaacca tcgcttgttt gctcgccatt   13260
ttattggcga tatgagatgt tttcccagat tggggcgttt tttgactcct cactcttact   13320
tctggtggct ttctttgttg tgtaccggtt tatcctggtc ctttgccgat ggcgacggca   13380
acagcccgac ataccaatac atatataact tgacgatatg tgagctgaat gggaccacct   13440
ggctgtccaa caattttac tgggcagtcg aaacttttgt gctttacccg gtggtgaccc    13500
acatcgtctc actgggtttc ctcacaacta gccatttctt tgacgcgctc ggcctcggag   13560
ctgtgtccgc tgtgggattt gctggcgggc ggtatgtcct cagcagcata tacggcgttt   13620
gtgcattcgc agcgctcgtg tgtttcatca tccgtgttgt taaaaattgc atggcgtgcc   13680
gctatgcccg tactcggttc accaacttca ttgttgacga ccgaggaaga attcacagat   13740
ggaagtcccc aatagtggtg gaaaaaatgg gtaaggccga agttggcagc agtctcgtca   13800
ccatcaagca tgttgttctc gaaggggtta aagctcaacc cttgacgagg actccggctg   13860
agcaatggga agcctagatg acttttgcta tgattccgcc gctacacaaa gcttctact    13920
agctttcagt atcacatacca cacctgttat gatatacgcc cttaaggtat cacgcggccg   13980
acttttgggg cttttgcaca tcttgatttt cctgaattgt tccttcacat tcggatacat   14040
gacccatgag cgtttccatt ccaccaatcg tgtggcgctt actatgggag ctgttgtcgc   14100
tctcctgtgg ggcatctata gcctcacaga atcatggaag tttattactt ccaggtgcag   14160
attgtgttgc ctaggccggc aatacatcct ggcccctgcc caccacgtag aaagtgccgc   14220
aggactccat tcaatcccgg cgtctggcaa ccgagcatac gccgtgagaa agcccggatt   14280
aacatcagtg aacggcactt tagtaccagg gcttcggagc ctcgtgttgg gcggcaagcg   14340
agctgttaaa cgaggagtgg ttaacctcgt caaatatggc cggtaaaaac cagagccaga   14400
agaagaagaa aaatacagct ccaatgggga atggccagtc agtcaatcaa ctgtgtcagt   14460
```

-continued

| | |
|---|---|
| tgctgggcac gatgatgaga tcccagcgcc agcgatccaa ggggggacag gccaaaaaga | 14520 |
| aaaagcttga gaagccgcat ttcccctgg ccgctgaaga tgatgtccgg caccacctca | 14580 |
| cccaaaccga acgttcctt tgtctgcaat cgatccagac agcctttaat caaggtgcgg | 14640 |
| gaactgcgtc gctttcatcc agtgggaagg tcggttttca ggttgagttt atgctgccgg | 14700 |
| ttcctcatac ggtgcgcctg attcgcgtga cttccacatc cgccagtcag ggtgcaaatt | 14760 |
| aatttgatag tcaggtgaat ggccacgatt ggcgtgtggc ctctgagtca cctattcaat | 14820 |
| tagggcgatc acatgggggc tagacttaat caggcgagaa ccatgtgacc gaaatt | 14876 |

<210> SEQ ID NO 4
<211> LENGTH: 15043
<212> TYPE: DNA
<213> ORGANISM: Artificial Sequence
<220> FEATURE:
<223> OTHER INFORMATION: cDNA from Porcine Reproductive and Respiratory
      Syndrome virus

<400> SEQUENCE: 4

| | |
|---|---|
| atgatgtgta ggggagatac cctacacaca caacactcct agtgtttgtg taccttggag | 60 |
| gcgagggtac agccccgccc cactccttgg ccctgtttc agcccaacag ggacccttct | 120 |
| ccctcgggc gagtgtgccg cctgctgctc tctcgcagcg ggaaggacct cccgagtatt | 180 |
| tccggagagc acctgcttca cgggatctcc acccttaac catgtctggg atgttctccc | 240 |
| ggtgcatgtg caccccggct gcccgggtat tttggaacgc cggccaagtc ttttgcacac | 300 |
| ggtgtctcag tgcgcggtct cttctccctc tagagcttca ggactctgac ctcggcgctg | 360 |
| ttggctgttt ttataagcct agggacaagc ttcattggaa ggtccccatg gcatccctc | 420 |
| aggtggagtg cactccatcc ggatgctgtt ggctcgcagc catttttcct atagcgcgta | 480 |
| tgacctccgg caatcacaat ttctcccagc gacttgtgaa agttgctgat gttttgtacc | 540 |
| gcgacggttg tctaacacct caacaccttc gtgaactcca agtttacgaa cgcggctgca | 600 |
| actggtaccc gatcacgggg ccagtgcccg ggatgggttt atttgcgaac tccgtgcacg | 660 |
| tgtctgacca gccgttcccc ggcgccactc atgtgttaac caactcacca ttgcctcagc | 720 |
| aggcttgtcg acagccgttc tgtccatttg aggtggctca ttctaacgta tacaggtggg | 780 |
| gggagtttgt gatctttgtg gactctcctt ccggcggtcg atcgcgtatg atgtggacac | 840 |
| cgggatccag tgactcggct gccctagaag cgttaccgtc cgcattagaa cgtcaggccg | 900 |
| gagtccttgt tcgaagtttc cctgcccacc acccgtcga ccttgctgac tgggagctta | 960 |
| ccgaatcccc tgaacacggt ttttccttca gcacatttca ttcttgtggt taccttgctc | 1020 |
| aaaaccccga agttttgac ggtaagtgct ggctttcctg cttcctgggc ttgccgaccg | 1080 |
| gcgtgcggc ttgtgaggaa tttttagctg gcgcctttgg ttatcaaacc aaatgggggg | 1140 |
| tgcacggaaa gtacctccaa cgtaggcttc agattaacgg ccttcgcgct gtggtcgatc | 1200 |
| ctgacggtcc catccatgtt gaagcacttt cttgtcccca gtcttggatc aggcatctga | 1260 |
| cttttgacga tgatgtcacc ccgggattcg ttcgcttaac atcccttcgc attgtgtcaa | 1320 |
| atacagagac cacctcctcc cagatctttc ggttcggggc gcataagtgg tacgcgctg | 1380 |
| ccggcaagcg ggctcgcgct aagcgtgctg caaagagtga aagaaatcg gttcccaccc | 1440 |
| ccgagactgt tccgctgacc ccgcctgtg gagtcaccat ctattcccca ccggcagacg | 1500 |
| ggtcctgtgg ttggcatgcc cttgccgcca tattgaacca gatgatgaac ggtgacttca | 1560 |
| cgtcccttt gcctcagtac aacaggccag aggatgattg ggcctctgac aacgaccttg | 1620 |

-continued

| | |
|---|---|
| ctcaagcaat tcaactcctg cgactaccgg ctaccatagt tcggactcgt gcctgtccta | 1680 |
| atgccaggta ccttataaag ctgaatgggg ttcactggga agtggaggag aggctgggga | 1740 |
| cggctctttg ctccctttct cgtgaatgtg tggttggtgt ttgctctgaa ggctgtgtcg | 1800 |
| catcgcctta tccaacagac ggggtaccag agcgtgcact cgaggccttg gcatctgctt | 1860 |
| acagactacc ctccgattgt gtttgctctg gtatttctga cttccttacc gaaccgcctc | 1920 |
| ctcaggaact ctggactctc gacaggatgt tgacctctcc atcacctgag cggtccggct | 1980 |
| tctccagttt gtataaatta ctgctcgagg ttgtccctca aaaatgcggt gctacggaag | 2040 |
| gggctttcac ctatgctgtt gagagaatgt gagggactg ccgaagctcc aaacaagcca | 2100 |
| tggctctttt ggcgaaaatt aaagttccgt cttcaaaggc ttcatctgtg tccctggacg | 2160 |
| agtgttt ccc tacgggtgct ccaggtgatt ctgagccagc acttcaggag gggcctcgaa | 2220 |
| gcctcggtgc tgccgttgtc ccatgcctgc ctggtgcaaa aggattcgag gaagcagccc | 2280 |
| cggaaggggt tcatgagaat ggctacgatg ccacccaccc tgcgctcttt gctgagcgtt | 2340 |
| ctaccaacga gcaggcacga atggcagccg gtaggcaatt ggggttcagc gatcgtgatt | 2400 |
| tggcagtcaa gaacattaat gaaggtgatt cggtctcggt tggtccaaca gaaggcacac | 2460 |
| tcaatggtca gggagacgaa ccactggatt tgtcccgacc agcactgacc actacaacga | 2520 |
| cccttatggg agaacgagaa cccgacaacc ctggttctga tgccggtgct tcccctgata | 2580 |
| ctgttcgaga attttccttg acggggctca cattccgtca tgttgagcac tgtggtacgg | 2640 |
| agtcgggtga cagcgattcg cctttggatt tgtctgacac gcagacccag gaccaacctt | 2700 |
| tagatctatc cctggcctct tggccagtga aagctaccgc atctgacccc ggctgggttc | 2760 |
| acggtaggcg tgagcctgtc tttgtgaagc ctcgaaatgc tttctctgat ggcgattcag | 2820 |
| tccttcagtt tggagggctt tctgaacccg gctctgtcat cgagcctgac cagataaaag | 2880 |
| gtgccccggt gactgacacc cctaccgacc taacgacttc tgacgagtcc tttcccgcag | 2940 |
| gtgatcctct tgaactcgct gagcttaagc gcccacagtt ctccgtacag gccttaattg | 3000 |
| atcgaggggg cccacttgct gcattttatg caaaaataaa gaatcgggta tatgaacagt | 3060 |
| gcctccaagc ctgtgagccc ggtagtcgtg caaccccggc cactaaggag tggctcaaca | 3120 |
| aaaatgtgggg tagggtagac atgaagactt ggcgttgtac ttcgcagttc gaagctggtc | 3180 |
| gctctcttgc gtcccttgaa ttcctccctg atatgatcaa cgacactcca cccctgttc | 3240 |
| ccaggaataa ccgggtcagt gacgacgccg gcttgaagca actggtagca caatgggata | 3300 |
| agaaattgag cgcacccccc ccccaaaac tggttgggcc agtgatcgac cagagcgccc | 3360 |
| tcccaccagc aggtgtccaa caggaaaata tcaccccttc cgatgggccg cctcaagcgc | 3420 |
| cggattttcc tggtcgagcg ggtacaggca gaggttggaa aggctttgtg ctttccggca | 3480 |
| ctcgtcttgc agagtctgtt agtcagcgcc ttatgacgtg ggttttgaa gtctactccc | 3540 |
| atctcccagc ttttatgctc gcacttttct cgccacgggg ctctatggtt ccaggtgatt | 3600 |
| ggttgtttgc aggtgttgtg ttacttgctc tcttgctctg tcgttcttac ccagtactcg | 3660 |
| ggtgtctacc cttactgggt gtattttctg gttctctacg gtgtgttcgt ctgggtgttt | 3720 |
| ttggttcttg gatggctttt gctgtatttt tattctcaac tccagccgat ccagtcggtt | 3780 |
| cttcttgtga ccacgattcg ccgaagtgtc atgctgagct tttggctctt gagcagcgcc | 3840 |
| aactttggga acctgtgcgc ggccttgttg tgggcccctc gggtctctta tgcgtcattc | 3900 |
| ttggcaagtt actcggtggg tcacgttatc tctggcatgt tttcttacgt ttatgcatgc | 3960 |
| ttgcggattt ggcccttt ct cttgtttatg tggtgtccca ggggcgttgt cgcaggtgtt | 4020 |

```
ggggaaagtg tataaggaca gctcctatgg aggtggccct caacgtattc ccttttttcgc    4080
gtgccacccg ctcctctctc gtgtccttgt gtgatcgttt tcaaacgcca aaaggggttg    4140
atcctgtgca cctggcaacg ggttggcgcg ggtgctggtg cggtgagagt cccatccatc    4200
aatcacatca aaagcccata gcttatgcca atttggatga aaagaaaata tctgcccaaa    4260
cagtagtcac tgtcccatat gatcccagtc aggctgtcaa gtgcctaaaa gttttgcagg    4320
cagggggggc catcgtagac cagcccacac ctgaggtcgt tcgtgtgtcc gagatcccct    4380
tctcagcccc atttttccca aaagttcccg tcaacccaaa ttgccgggtt gtagtggatt    4440
cagacacttt cgtggccgca gtccgatgcg gttactcaac agcacaactg gttctaggcc    4500
gtggtaactt tgctaagtta aatcaggccc ctcccaaaaa ctctgccctc accaaagcaa    4560
ctggtggggc ttcttacacc cttgctgtgg ctcaagtgtc tgtgtggact cttgttcatt    4620
tcatccttgg catttggctc acaacacctc aagtgtgtgg acgagggacc gtcgacccat    4680
ggtgtacaaa ccccttttcg taccccactt acggccccgg agttgtgtgc tctgctcgac    4740
tttgtgtgtc cgccgacggg gttaccctgc cgttgttctc tgccgtggca cagctctccg    4800
gtagggaggt agggatcttc attttggtac tcgcctcttt gggtgctctt gtccaccgcc    4860
tggctcttaa ggcagacatg ttaatggtct ttttggcttt ttgtgcttac gcctggccta    4920
tgagctcctg gttgatttgc ttcttcccca tactcttgaa gtgggtcaca cttcaccccc    4980
tcaccatgtt ttgggtacac tcatttttag tgttttgtct gccagcagcc ggtatcctct    5040
cactgggagt gactggtctt ctctgggcaa ttggccgctt tacccaggtt gccggaatta    5100
ttacaccta tgacatccat cagtacacct ctgggccacg tggtgcggcg gctatagcca    5160
cagcccctga aggcacttac atggccgccg tccggagagc cgctttaact gggcgaactt    5220
tgatcttcac cccgtcagca gtaggatccc ttcttgaggg agcctttagg accgtaaac    5280
cctgcctcaa caccgtgaat gtcgtgggct ctttcccttgg ttcaggaggg gttttcaccg    5340
ttggtggaaa gaaaataatc gtcaccgcag cccacgtgct gaatggtgac acggctagag    5400
tcaccggtga ctcctacaac cgcttgcaca ccttcaatac taatggtgat tacgcctggt    5460
ctcatgctga agactggcag ggcgttgccc ctgcagtcaa cattgcgaag gggtaccgcg    5520
gccgcgccta ttggcaaacg tcaaccggtg tcgagcccgg agttgttggg ggagggtttg    5580
ccttctgttt tactaactgc ggagactcgg ggtcacctgt tatctcagaa tctggtgatc    5640
ttattgggat tcacaccggc tcaaacaaac tcggctctgg tcttgtaaca acccctgaag    5700
gggaaacctg cactattaaa gaaaccaagc tctctgacct ttctaaacac tttgcaggcc    5760
caagcgttcc cctcggggac atcaaattga gtccggccat tatccctgac gtgacatcca    5820
ttccgagtga cttggcgtcg ctcttgactt ctgtccctgt aatggaaggc ggcctctcga    5880
ccgtccaact tttgtgtgtc ttttttcttc tctggcgcat gatgggccat gcctggacac    5940
ccgttgttgc cgtgggcttc ttcctgctga atgaaatcct cccagcagtc ttggtccgga    6000
ctgtgttttc ttttgcactc tttgtgctgg catgggcaac cccttggtct gcacaggttt    6060
taatgatcag gcttctcacg gcatctctca atcgtaacag gtcttcttta gtgttctacg    6120
catttggagg catcgtcggc ttggccgttg aaatcggac cttctctggc agattgcctg    6180
cattgtctca gcccttttcg acatattgct ttttacccag agcccttgtc atgaccagct    6240
gtgtccccac cattatcatt gggggattcc atatcctcgg tgtaatcttg tggttgttca    6300
aataccggta cctccacaac atgctggtcg gtgatgggag tttttcaagc gccttttttcc    6360
```

```
tacggtattt tgctgaaggc aatctcagga agggtgtctc aaagtcttgt ggcatgagta    6420
acgagtccct aacggctgca ctggcctgca aattatcaca ggctgacctt gattttctat    6480
ccagcttgac gaacttcaag tgctttgtat ccgcttcaaa catgaaaaat gctgccggcc    6540
agtacattga agcagcgtat gccaaggccc tgcgccaaga gttggcctcc ctagttcaag    6600
tcgacaaaat gaaaggagtc ttgtccaagc tcgaagcttt tgctgagaca gccactccgt    6660
cccttgacgc gggtgacgtg atcgttcttc taggacaaca tcctcacggg tctgttctcg    6720
acatcaatgt gggggctgaa aggaaaactg tatctgtaca agagacccgg agtctaggcg    6780
gctccaaatt cagcgtctgc actgtcgtgt ccaacacacc catcgatgcc ttaactagta    6840
ttccactcca gacaccaacc ccactcttcg agaatggtcc gcgtcatcgt ggcgaggagg    6900
acgatctcaa agttgagagg atgaagaaac actgtgtgtc cctcggcttt cacaacatca    6960
atggcaaagt ttactgtaaa atttgggaca gtctaccggc gacaccttc tacacagatg    7020 attcccggta tacccaggac tatgcttttc aagacagatc agtcgattac agggacaggg    7080
actatgaggg cgtacaaacc gtctcccatc agggattcga tccaaagtcc gaaacccctg    7140
tcggcactgt tgtgatcggc ggcattacgt ataacaggta tctgacaaag ggtaaagaaa    7200
ttctggttcc caggcctgac aactgccttg aagctgctaa attgtcctta gagcaagctc    7260
tcgccgggat gggtcagact tgcgaactta cgaccgccga gatggaaaag ttgaagcgca    7320
tcattagtca actccaaggt ttgaccactg aacaagcttt aaactgctag ccgccagcgg    7380
cttgacccgc tgtggccgcg gcggcttagt tgtgactgaa acggcggtaa aaattgtgaa    7440
ataccatagt agaactttta ccttaggctc cttagacctg aaggtcgctt ccgaggtaga    7500
ggttaaaaag tcagctgagc aaggccacgc tgttgtggca aacttatgct ccggtgtcat    7560
tttgatgaga ccccacccac cgtcccttgt tgatgttctt ctgaaacccg gacttgacac    7620
aaaacccggc attcaaccag ggcatggggc cgggaacatg ggcgtggatg gttctacttg    7680
ggattttgag accgcgccca caaaggcaga gcttgagtta tcgaagcaga taatccaagc    7740
atgtgaagtt aggcgcggag acgctcccaa cctccaactc ccttacaaac tttaccctgt    7800
caggggaaac cctgagcggc atgacggccg tctcactaac accaggtttg agatttgcc    7860 ttacaagacc cctcaggaca ctaaatccgc aatccacgcg gcttgttgcc tgcatcccaa    7920
tggggtcccc gtatctgatg gcaaatctac actaggtacc actcttcaac atggtttcga    7980
gctttatgtc cctaccgtgc cctatagtgt catggagtac cttgattcgc gttctgacac    8040
ccctctcatg tgtactagac atggcacttc caaagctgcc gcagaggacc tccaaaagta    8100
tgatttatcc acccagggtt ttgtcctgcc tgggtccta cgccttgtgc gcaagtttgt    8160
ttttggccat gttggtaagg caccgccatt gttccttcca tcaacctacc ccgcaaaaaa    8220
ctccatggca ggggtcaatg ccaaaggtt cctacaaaa gatgttcaga gcatacctga    8280
agttgatgaa atgtgtgctc gcgccgtcaa ggagaattgg caaactgtga cgccttgtac    8340
tcttaagaaa cagtactgct ccaagctcaa aaccagaacc atcctgggca ccaacaattt    8400
tattgcccta gcccacagat cggcgctgag tggcgtcacc caggctttta tgaagaaggc    8460
ctggaattcc ccaattgcct tggggaaaaa taaattcaaa gagctgcact gtgttgtcgc    8520
cggcaggtgc cttgaggctg atctggcctc ctgtgaccgc agcaccctg ccgttgtaag    8580 atggtttgtt gccaacctcc tgtacgaact cgcggggtgt gaagagtatt gcctagcta    8640 tgtgctcaat tgctgccatg atctcgtagc aacacaggat ggtgccttta cgaaacgcgg    8700
tggcctgtcg tctggggacc ccgtcactag cgtgtccaac actgtgtatt cactgataat    8760
```

```
ttatgcccag catatggtgt tatcagcttt gaaaatgggt cacgaaattg gtctcaagtt    8820
ccttgaggaa cagcttaaat tcgaagacct tcttgaaatt cagcccatat tggtgtattc    8880
tgatgacctc gtattgtatg ccgaaagacc aacttttccc aactaccact ggtgggttga    8940
gcatcttgac ctaatgctgg gcttcaaaac ggacccggca aaaaccgtca taaccgacaa    9000
gcccagcttc ctcggctgta gaattgaggc agggcggcag ctagttccca atcgcgaccg    9060
catcctggct gctctcgcat accacatgaa ggcgcagaac gcctcagagt attatgcgtc    9120
tgctgctgca atcctaatgg attcatgtgc ttgcattgac cacgaccctg agtggtatga    9180
ggacctcatt tgcggtattg cccggtgcgc ccgccaggat ggttacagct cccaggtcc     9240
accattttc atgtctatgt gggagaaatt gagaagtcat aatgagggga agaaattccg     9300
ccattgcgga atctgcgacg ccaaagccga ccatgcgtcc gcttgcgggc ttgatttgtg    9360
tttgttccat tcgcactttc atcaacactg cccagtcact cttaactgcg gtcatcatgc    9420
cggttcaaag gaatgttcgc ggtgccagtc acctgttggg gctggaaaat cacctcttga    9480
tgccgtgcta gaacaaattc catacaaacc tcctcgcact gtcatcatga atgtgaacag    9540
tggaacgacg gcccttgatc cagggaggta ccagtcccgt cgtggcctcg ttgcagttaa    9600
gaggggtatc gcaggtaatg aagttgatct ccctgatgga gactatcaag tggtgcctct    9660
tttaccgact tgcaaagaca taaacatggt gaaggtggct tgcaatgtgc tgctcagtaa    9720
gttcatagtg gggccgccag gttccgggaa aaccacctgg ctattgagtc aagttcagga    9780
cgatgacgtc atttacacac ctacccacca gaccatgtat gacatagtta gcgccctcaa    9840
ggtttgtagg tattctatcc caggagcctc gggacttcct tttccgccac ctgccagatc    9900
cgggccgtgg gttaggcttg ttgctagcgg ctacgtccct ggccgagtgt catacctcga    9960
tgaggctgga tattgcaatc acctggacat tcttagactg ctttctaaaa cacccettgt    10020
ttgtttgggt gacctccagc aacttcaccc tgtcggcttt gattcctact gttatgtgtt    10080
tgatcagatg cctcagaagc agttgactac catttataga ttcggtccta acatctgtgc    10140
agccatacag ccttgttaca gggagaaact cgaatccaag gctaggaata ccagggtggt    10200
cttcaccacc cgacctgtgg cctttggcca ggtgctgaca ccataccata aagatcgcgt    10260
cgactccgcg ataaccatag attcgtcaca gggggccacc ttcgacattg taacgttgca    10320
tttgccatca ccaaaatcct taaacaaatc ccgagcactt gtagccatca ctcgggctag    10380
gcacgggttg ttcatttacg atccccataa ccagctcagg gagttttca acctgacccc    10440
tgagcgtact gaatgcaacc tcgtgttcag ccgtggggat gagctggtgg ttctgaacgc    10500
ggacaatgca gtcacgactg tagtaaaagc cctagaggtg ggttcatccc agtttcgagt    10560
gtcagacccg aggtgtaaat ctctcttagc tgcttgttca gccagtctgg aggggagctg    10620
tatgccgtta ccccaagttg ctcataacct agggttttat ttttcccctg acagtccggc    10680
atttgcaccc ctgccaaaag agttggcacc acattggcca gtagttactc accagaataa    10740
tcgggcatgg ccagaccggc tcgtcgctag catgcgccca attgatgctc gctacagtaa    10800
accaatgatt ggtgctggtt atgtagtcgg accatccacc tttctcggca ctcctggcgt    10860
agtgtcatac tatctcaccc tatacattag gggtgagccc caggccttgc cagaaacact    10920
cgtgtcaaca ggacgcatag ccacagattg tcgggagtat cttgatacag ccgaggaaaa    10980
tgcggcaaaa gaactccctc acgcatttat tggtgatgtg aaaggcacta cggtcggtgg    11040
gtgccatcat attacatcaa aatacctgcc taggaccttg cctaaggact ctgttgccgt    11100
```

```
ggtcggagtg agttcgcccg gcaaggctgc taaagccatg tgtaccctca ccgatgtgta   11160
ccttcctgaa ctccgaccat atctgcaacc aaagacggca tcaaaatgct ggaaactcaa   11220
gttagacttc agggacgtcc gactgatggt ctggaagggg gctaccgcct acttccagct   11280
tgaagggctc acatggtctg cgctgcctga ttacgccagg ttcatccagc tacccacgaa   11340
tgccgtcgtg tacatcgacc cgtgcatagg accggcagca gccaaccgta aagttgtgcg   11400
aaccacggat tggagagcgg acctggcggt aacaccatat gactacgdtg ctcaaaccat   11460
tctgacgaca gcctggttcg aggacctcgg gccacagtgg aaaattttag gactacagcc   11520
cttcaggcga gcattaggct ttgacaacac tgaggactgg gcaattcttg cacgccgtat   11580
ggatgacggt aaggattaca ttgactacaa ctggagttgt gttcgaaacc gcccatgcgc   11640
tatccatgga cgtgcgcgtg accacaccta tcattttgct catggtacgg aattagggg    11700
ggagctgggt aaacctcggt taccgcctga ataagacccc cttgaaccca aagcaatgcg   11760
atgggttcat tatggagcaa aatcagtcaa ttgttcgtgg acgcttttac cgaattcctt   11820
gttagcgtgg ttgatattgt catctttctt gccatattgt tcgggttcac agtcgctgga   11880
tggctcctgg tcttttttct cagagtggtt tgctccgcga ttctccgttc gcgctctgcc   11940
attcactctc ccgagttatc gaaggtccta tgagggcctg ctgcccaatt gcaaaccaga   12000
tgtcccacaa ttcgcaatca agcacccact aggtttgctc tggcacatgc gagtctctca   12060
gttaatcgac gagatggtct ctcgtcgcat ttaccagacc atggaacact caggtcaggc   12120
agcctggaag caggtagtca gtgaggccac ccttacaaag ttgtcaaggc tcgatgtagt   12180
tgcccatttc caacatttgg ctgcagtgga ggcggattcc tgcaacttcc tcagctcacg   12240
acttgtgatg ctgaaaaatt tagctgtcgg taacgtgagt gtattttaca acgccacgtt   12300
ggaccgcgtt gaactcgtct tccccacgcc aggcacgagg cccaaattga ccgactttag   12360
gcaatggctt atcagcgtgc atgcttccat tttctcctct gtggcttcat cggttacctt   12420
gttcatggtc ctttggcttc gggttccaac tctacgctat gttttttggtt tccattggcc   12480
cacggcaaca cgtcattcga gctgaccatc aactacacca tatgtatgcc ctgtcccacc   12540
agccaagcgg ctcaacaaag gctcgaaccc ggtcgtaata tgtggtgcaa gattggatac   12600
tctacgtgcg aggagcatga tcacgatgaa ctgtcgatgg ctataccacc tgggtatgac   12660
aatctcaaac ttgaaggcta ttatgcatgg ttggctttct tgtccttttc ttacgcggct   12720
caattccatc cggagttatt cggaataggg aatgtgtcgc gcgttttcgt ggacaagcag   12780
catcagttca tttgcgccga gcatgatgga cccaattcaa ccgtaaccac tggacataac   12840
atttccgcat tgtatgcggt gtactaccat caccaagttg acggggcaa ctggtttcat   12900
ttagaatggc tgcggccgtt cttctcctcc tggctggtgc tcaatatctc atggtttctg   12960
aggcgttcgc ctgcaagccc tgtttctcga cgcatctatc agatattaag accaacacga   13020
ccgcggctgc cggtttcatg gtccttcaga acatcgactg cctctcagca gcgcagagga   13080
gtgctcccgt cataaagtca tctcaatgcc gtgaagccat tggtacccca cagtacatta   13140
cgataacagc aaatgtgacc gatgaagcgt atttgtacaa tgcagactta ctgatgcttt   13200
ctgcatgcct tttctatgcc tcagaactga gcgagaaagg ctttaaagtt atctttggga   13260
atatctccgg tgtcgtctct gcatgcgtca atttcacgga ttatgtgact catgtgactc   13320
aacacacaca acagcatcat ttggtgatcg atcacgttcg gttgctgcat ttcctgacac   13380
cgtcagtgat gaggtgggct acaaccatcg cttgcttact tgccatcctt ctggcgtatat   13440
gagatgttct cacaaattgg ggtgtttttc gactctgtat tcctgctcct ggtggctttc   13500
```

```
tttgctgtgt accggcttgt cctggtcctt tgtcgatggc aacggcgaca gctcgacata   13560
ccaatatata tataatttga cgatatgcga gctgaatgga accaaatggt tgtccaacca   13620
ttttgattgg gcagtcgaga ctttcgtgct ttacccggtc accactcaca tcatctcatt   13680
gggtttcctc acaacaagcc atttttttga cgcgctcggt cttagcgctg tatccattgt   13740
aggatttgct gatgagcggt acgtacttag tggtgtgtac ggtgcttgtg cttttgccgc   13800
gctcgtgtgt tttgtcatcc gtgctgctaa gaactgtatg gcttgtcgct atgcccgtac   13860
ccggttcacc aatttcattg tggacgaccg ggggaaaatc caccgctgga agtcaccgat   13920
agtggtggaa aagttgggca aagctgaagt cggtgatgct cttgtcacca tcaagcatgt   13980
cgtcattgaa ggggttaaag ctcaacccct gacgagaact tcggccgagc aatggcaaac   14040
ctagatgact tctgcaatga tcccactgcc gcgcaaaagc ttgtgctagc cttcagtatt   14100
acatacacac ctataatgat atatgccctc aaagtgtcac gcggccggct cctggggctg   14160
ttgcacatcc tgatatttct gaactgttct ttcacgtttg ggtacatgac gtatgtgcat   14220
tttcaatcca ccaatcgtgt cgcgcttact atggggggctg ttgttgccct tttgtggggc   14280
atctatagtt ttacagaatc atggaggttt gtcacctcca ggtgcagact gtgttgccta   14340
ggccggcgat acattctggc ccctgcccat cacgtggaaa gtgccgcagg tctccattca   14400
atcccagcgt ctggcaaccg agcatacgct gtgagaaagc ccggactaac atcagtgaac   14460
ggcactctag taccaggact tcggagcctc gtgctgggcg gcaaacgagc tgttaaacgg   14520
ggagtggtta acctcgtcaa gtatggccgg taagaaccag agccagaaga aaaagcaaaa   14580
tacagctcct atggggaatg gccagtcagt caatcaactg tgccagctgc tgggtgtaat   14640
gatgaaatcc cagcgccaac ggcctagggg aggacaggca aaaagaaaa agcctgagaa   14700 gccacatttc cccctggctg ctgaggatga cattcggcac cacctcaccc aaactgaacg   14760
ttctctctgc ttgcaatcga tccaaacggc tttcaaccaa ggcgcaggaa ttgcgtcgct   14820
ttcacccagc gggaaggtca gttttcaggt tgagtttatg ttgccggttg ctcatacagt   14880
gcgcttgatt cgcgtgactt ctacacccgt cagtcagggt gctagttaat ttgacagtca   14940
ggtgaatggc cgcgattgac gtgtggcctc taagtcacct attcaattag ggcgatcaca   15000
tgggggttac acttaattag gcgagaacca tgtgaccgaa att                    15043
```

PORCINE REPRODUCTIVE AND RESPIRATORY SYNDROME VACCINE VIRUS

CROSS-REFERENCE TO RELATED APPLICATIONS

This application is the National Stage entry of International Application No. PCT/EP2019/076174, filed 27 Sep. 2019, which claims priority to European Patent Application No. 19382734.2, filed 29 Aug. 2019.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_listing_2920951-236000_ST25.txt" created on 13Dec. 2021, and 79,098 bytes in size) is submitted concurrently with the instant application, and the entire contents of the Sequence Listing are incorporated herein by reference.

BACKGROUND

Field

The present invention relates to modified, live Porcine Reproductive and Respiratory Syndrome viruses. The modified, live viruses are useful in vaccines, particularly in vaccines which provide protection against heterologous viruses.

Description of Related Art

Porcine Reproductive and Respiratory Syndrome (PRRS), originally called Mystery Swine Disease, was first described in Europe but has now spread worldwide. PRRS causes late-stage abortions, stillbirths, and infertility in breeding age sows, and respiratory disease, decreased growth performance, and even death in nursery and growing/finishing pigs. PRRS causes significant economic losses.

Symptoms of PRRS virus infection in adult porcine animals include, without limitation, reduced appetite, lethargy, and fever. Pregnant sows may prematurely farrow, abort fetuses, or deliver mummified or stillborn piglets, and up to 10% of pregnant sows may die from PRRS virus infection. Infected piglets have a high pre-weaning mortality rate, are often weak, and can have edema around the eyes. PRRS virus infection in weaned nursery or grow/finish pigs can cause, without limitation, a failure to thrive, respiratory distress, labored or rapid breathing, blotchy reddening of the skin, and rough hair coats.

The PRRS virus is an enveloped virus with an approximately 15 kb, linear, positive-stranded RNA genome, and the virus has been classified to the family *Arteriviridae*. To date at least eleven open reading frames have been identified in the genome. PRRS viruses are divided into two genotypes. The European genotype, Type 1 PRRS viruses (PRRSV-1), are exemplified by the Lelystad strain, while the Type 2 North American PRRS viruses (PRRSV-2) are exemplified by the strain VR-2332.

The two genotypes can have as little as about 60% sequence identity in their genomes, and even within genotypes individual strains can vary up to about 20% in the identity of their genomes. This variability has complicated the development of vaccines to effectively treat and/or prevent PRRS. Modified, live virus (MLV) variants of the PRRS virus can generate immunity against challenge with PRRS viruses, but the vaccine is most effective when the challenge is with a PRRS virus genetically homologous to the MLV. The MLV vaccines have been less effective against challenge with heterologous viruses. Further, MLV have shown some reversion to virulence, such that the vaccine virus causes disease in vaccinated animals. Vaccines containing inactivated (i.e. killed) PRRS viruses have better safety profiles, but efficacy against heterologous challenge has been limited.

Because current PRRS vaccines do not show sufficient safety and efficacy to reduce the economic impact of PRRS virus infection, new and improved vaccines are needed. Preferably, those vaccines would be both safe and efficacious. If the vaccines comprise attenuated MLV, those attenuated MLV should not demonstrate reversion to virulence in order to be considered safe to use in the field. For example, by adapting a PRRS strain to growth in tissue culture cells for at least 60 passages, at least 70 passages, at least 80 passages, or preferably at least 85 passages, the MLV should not demonstrate reversion to virulence. To be efficacious, a vaccine virus strain should be able to elicit protective immunity in a porcine animal against a range of phylogenetically diverse wild type PRRS strains. Preferably, a new PRRS vaccine virus strain would be able to elicit protective immunity in a porcine animal against at least three phylogenetically diverse wild type PRRS strains.

SUMMARY OF THE INVENTION

The present invention provides for a modified, live Porcine Reproductive and Respiratory Syndrome vaccine virus strain, wherein the consensus complementary DNA sequence of said PRRS strain is at least 90% identical to a sequence selected from the group of SEQ ID NO: 1, SEQ ID NO: 2, SEQ ID NO: 3, and SEQ ID NO: 4. Preferably, the modified, live strain could have a consensus complementary DNA sequence that is at least 95% identical to a sequence selected from the group of SEQ ID NO: 1, SEQ ID NO: 2, SEQ ID NO: 3, and SEQ ID NO: 4. More preferably, the modified, live strain could also have a consensus complementary DNA sequence that is at least 98% identical to a sequence selected from the group of SEQ ID NO: 1, SEQ ID NO: 2, SEQ ID NO: 3, and SEQ ID NO: 4. As a person of ordinary skill will appreciate, due to the high mutation rate of the PRRS virus, a modified, live PRRS strain might comprise a multiplicity of subpopulations, each having a homologous but not identical genome.

The present invention provides for a modified, live Porcine Reproductive and Respiratory Syndrome (PRRS) virus strain, wherein the PRRS virus strain is a DE 14-3073, a ES 13-49, a IT 14-32, or a PL 14-02 strain. The PRRS virus strain should be passaged preferably at least 60 times, or more preferably 70 times, or even more preferably 80 times, in tissue culture cells. Most preferably, the PRRS virus strain should be passaged 85 times in tissue culture cells. Such passaging in tissue culture cells is useful in attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Most preferably, modified, live PRRS virus strains passaged 85 times have a low probability of reverting to wild-type virulence.

The present invention provides for an immunogenic composition comprising a modified, live PRRS virus strain having a consensus complementary DNA sequence at least 90% identical to a sequence selected from the group consisting of SEQ ID NO: 1, SEQ ID NO: 2, SEQ ID NO: 3, and SEQ ID NO: 4. Preferably, the modified, live strain could have a consensus complementary DNA sequence that is at least 95% identical to a sequence selected from the group consisting of SEQ ID NO: 1, SEQ ID NO: 2, SEQ ID NO: 3, and SEQ ID NO: 4. More preferably, the modified, live strain could also have a consensus complementary DNA sequence that is at least 98% identical to a sequence selected from the group consisting of SEQ ID NO: 1, SEQ ID NO: 2, SEQ ID NO: 3, and SEQ ID NO: 4. As a person of ordinary skill will appreciate, due to the high mutation rate of the PRRS virus, a modified, live PRRS strain might comprise a multiplicity of subpopulations, each having a homologous but not identical genome.

The present invention provides for an immunogenic composition comprising a modified, live PRRS virus strain, wherein said PRRS virus strain is a DE 14-3073 strain, a ES 13-49 strain, a IT 14-32 strain, or a PL 14-02 strain. The DE 14-3073 strain or the ES 13-49 strain or the IT 14-32 strain or the PL 14-02 strain that may be passaged at least 80 times, or preferably even 85 times, in tissue culture cells. Most preferably, the immunogenic composition comprises at least one pharmaceutically-acceptable excipient. The immunogenic composition may also comprise a further antigen from a different virus or from a bacterial strain or from a parasite.

The present invention provides for a vaccine comprising a modified, live PRRS virus strain, wherein the consensus complementary DNA sequence of said PRRS strain is at least 90% identical to a sequence selected from the group consisting of SEQ ID NO: 1, SEQ ID NO: 2, SEQ ID NO: 3, and SEQ ID NO: 4. Preferably, the modified, live strain could have a consensus complementary DNA sequence that is at least 95% identical to a sequence selected from the group consisting of SEQ ID NO: 1, SEQ ID NO: 2, SEQ ID NO: 3, and SEQ ID NO: 4. Most preferably, the modified, live strain could also have a consensus complementary DNA sequence that is at least 98% identical to a sequence selected from the group consisting of SEQ ID NO: 1, SEQ ID NO: 2, SEQ ID NO: 3, and SEQ ID NO: 4. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a vaccine for use in preventing Porcine Reproductive and Respiratory Syndrome in a porcine animal. As PRRS is caused by a PRRS virus, the present invention provides a vaccine for use in preventing a PRRS virus infection. The present invention also provides for a vaccine for use in a porcine animal for reducing a symptom caused by a PRRS virus infection. The infection may be from a wild-type virulent strain of a PRRS virus. A symptom may be, without limitation, reduced appetite, lethargy, fever, premature farrowing, abortion, stillbirths, edema, a failure to thrive, cough, respiratory distress, labored or rapid breathing, blotchy reddening of the skin, rough hair coats, lung lesions, viral shedding, and mortality. The present invention provides for a vaccine for use in prevention of PRRS in a porcine animal. Preferably, the vaccine comprises a modified, live PRRS strain having a consensus complementary DNA sequence that is at least 90%, at least 95%, or at least 98% identical to a sequence selected from the group consisting of SEQ ID NO: 1, SEQ ID NO: 2, SEQ ID NO: 3, and SEQ ID NO: 4. Most preferably, the vaccine comprises a modified, live PRRS strain which is a DE 14-3073 strain, a ES 13-49 strain, a IT 14-32 strain, or a PL 14-02 strain. The vaccine may further comprise a pharmaceutically-acceptable excipient. The vaccine may further comprise an adjuvant. The vaccine may comprise a further antigen from a different virus or from a bacterial strain or from a parasite.

The present invention provides for a method of preventing a symptom of Porcine Reproductive and Respiratory Syndrome in a porcine animal, comprising administering to said porcine animal an immunogenic composition comprising a modified, live PRRS virus strain. The present invention also provides for a method of preventing Porcine Reproductive and Respiratory Syndrome in a porcine animal, comprising administering to said porcine animal an immunogenic composition comprising a modified, live PRRS virus strain. Preferably, the modified, live PRRS virus strain for use in the method would have a consensus complementary DNA sequence at least 90% identical to a sequence selected from the group consisting of SEQ ID NO: 1, SEQ ID NO: 2, SEQ ID NO: 3, and SEQ ID NO: 4. More preferably, the modified, live PRRS virus strain for use in the method would have a consensus complementary DNA sequence that is at least 95% identical to a sequence selected from the group consisting of SEQ ID NO: 1, SEQ ID NO: 2, SEQ ID NO: 3, and SEQ ID NO: 4. Most preferably, the modified, live PRRS virus strain for use in the method would have a consensus complementary DNA sequence that is at least 98% identical to a sequence selected from the group consisting of SEQ ID NO: 1, SEQ ID NO: 2, SEQ ID NO: 3, and SEQ ID NO: 4. The immunogenic composition may further comprise a pharmaceutically-acceptable excipient. The immunogenic composition may comprise a further antigen from a different virus or from a bacterium or from a parasite.

The present invention provides for a method of preventing Porcine Reproductive and Respiratory Syndrome in a porcine animal, comprising administering to said porcine animal an immunogenic composition comprising a modified, live Porcine Reproductive and Respiratory Syndrome (PRRS) virus strain, wherein the said PRRS virus strain is a DE 14-3073 strain, a ES 13-49 strain, a IT 14-32 strain, or a PL 14-02 strain for use in the method may be passaged at least 80 times, or preferably even 85 times, in tissue culture cells. The immunogenic composition may further comprise a pharmaceutically-acceptable excipient. The immunogenic composition may comprise a further antigen from a different virus or from a bacterial strain or from a parasite.

The present invention provides for a method of preventing a symptom caused by a PRRS virus infection in a porcine animal, comprising administering to said porcine animal an immunogenic composition comprising a modified, live Porcine Reproductive and Respiratory Syndrome (PRRS) virus strain, wherein the consensus complementary DNA sequence of said PRRS strain is preferably at least 90% identical to a sequence selected from the group consisting of SEQ ID NO: 1, SEQ ID NO: 2, SEQ ID NO: 3, and SEQ ID NO: 4. More preferably, the modified, live strain for use in the method could also have a consensus complementary DNA sequence that is at least 95% identical to a sequence selected from the group consisting of SEQ ID NO: 1, SEQ ID NO: 2, SEQ ID NO: 3, and SEQ ID NO: 4. Most preferably, the modified, live strain for use in the method could also have a consensus complementary DNA sequence that is at least 98% identical to a sequence selected from the group consisting of SEQ ID NO: 1, SEQ ID NO: 2, SEQ ID NO: 3, and SEQ ID NO: 4. The immunogenic composition may further comprise a pharmaceutically-acceptable excipient. The immunogenic composition may also comprise a further antigen from a different virus or from a bacteria strain or from a parasite.

The present invention provides for a method of reducing a symptom caused by a PRRS virus infection in a porcine animal, comprising administering to said porcine animal an immunogenic composition comprising a modified, live Porcine Reproductive and Respiratory Syndrome (PRRS) virus strain, wherein the said PRRS virus strain is a DE 14-3073 strain, a ES 13-49 strain, a IT 14-32 strain, or a PL 14-02 strain for use in the method may be passaged at least 80 times, or preferably even 85 times, in tissue culture cells. The immunogenic composition may further comprise a pharmaceutically-acceptable excipient. The immunogenic composition may also comprise a further antigen from a different virus or from a bacteria strain or from a parasite. The PRRS virus infection may be an infection by a virulent PRRS virus heterologous to the modified, live PRRS virus strain in the immunogenic composition. Two PRRS virus strains are considered to be heterologous if a genomic consensus sequence of each virus strain maps to a different phylogenetic group. Two PRRS virus strains are considered to be heterologous if a complementary DNA consensus sequence of each virus strain maps to a different phylogenetic group.

The present invention provides for the use of a modified, live PRRS virus strain in the manufacture of a medicament for preventing or reducing a symptom of PRRS, wherein the modified, live PRRS virus comprises a consensus complementary DNA sequence at least 90% identical to a sequence selected from the group consisting of SEQ ID NO: 1, SEQ ID NO: 2, SEQ ID NO: 3, and SEQ ID NO: 4. Preferably, the modified, live strain could also have a consensus complementary DNA sequence that is at least 95% identical to a sequence selected from the group of SEQ ID NO: 1, SEQ ID NO: 2, SEQ ID NO: 3, and SEQ ID NO: 4. More preferably, the modified, live strain could also have a consensus complementary DNA sequence that is at least 98% identical to a sequence selected from the group consisting of SEQ ID NO: 1, SEQ ID NO: 2, SEQ ID NO: 3, and SEQ ID NO: 4.

The present invention provides for the use of a modified, live PRRS virus strain comprising a DE 14-3073 strain, a ES 13-49 strain, a IT 14-32 strain, or a PL 14-02 strain in the manufacture of a medicament for preventing or reducing a symptom of PRRS. The modified, live PRRS virus strain should be passaged at least 80 times, or preferably even 85 times, in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence.

The present invention provides for the use of an immunogenic composition comprising a modified, live PRRS virus strain in the manufacture of a medicament for preventing a PRRS virus infection, wherein the modified, live PRRS virus strain comprises a consensus complementary DNA sequence at least 90% identical to a sequence selected from the group consisting of SEQ ID NO: 2, SEQ ID NO: 3, and SEQ ID NO: 4. The modified, live strain for such use could also have a consensus complementary DNA sequence that is at least 95% identical to a sequence selected from the group consisting of SEQ ID NO: 1, SEQ ID NO: 2, SEQ ID NO: 3, and SEQ ID NO: 4. The modified, live strain for such use could also have a consensus complementary DNA sequence that is at least 98% identical to a sequence selected from the group consisting of SEQ ID NO: 1, SEQ ID NO: 2, SEQ ID NO: 3, and SEQ ID NO: 4.

The present invention provides for the use of an immunogenic composition comprising a modified, live PRRS virus strain comprising a DE 14-3073 strain, a ES 13-49 strain, a IT 14-32 strain, or a PL 14-02 strain in the manufacture of a medicament for preventing a PRRS virus infection. The PRRS virus strain should be passaged at least 80 times, or preferably even 85 times, in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 85 times have a low probability of reverting to wild-type virulence.

The present invention provides for the use of an immunogenic composition comprising a modified, live PRRS virus strain in the manufacture of a medicament for protecting a porcine animal from a PRRS virus infection, wherein the modified, live PRRS virus strain comprises a consensus complementary DNA sequence at least 90% identical to a sequence selected from the group consisting of SEQ ID NO: 1, SEQ ID NO: 2, SEQ ID NO: 3, and SEQ ID NO: 4. The modified, live strain for such use could also have a consensus complementary DNA sequence that is at least 95% identical to a sequence selected from the group consisting of SEQ ID NO: 1, SEQ ID NO: 2, SEQ ID NO: 3, and SEQ ID NO: 4. The modified, live strain for such use could also have a consensus complementary DNA sequence that is at least 98% identical to a sequence selected from the group consisting of SEQ ID NO: 1, SEQ ID NO: 2, SEQ ID NO: 3, and SEQ ID NO: 4.

The present invention provides for the use of an immunogenic composition comprising a modified, live PRRS virus strain comprising a DE 14-3073 strain, a ES 13-49 strain, a IT 14-32 strain, or a PL 14-02 strain in the manufacture of a medicament for protecting a porcine animal from a PRRS virus infection. The PRRS virus strain should be passaged at least 80 times, or preferably even 85 times, in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 85 times have a low probability of reverting to wild-type virulence.

BRIEF DESCRIPTION OF THE DRAWINGS

FIG. 1. Phylogenetic analysis of PRRSV-1 a DE 14-3073 strain, a ES 13-49 strain, a IT 14-32 strain, or a PL 14-02 strain and commercially available vaccines and selected isolates based on ORFS nucleotide sequences constructed by the neighbor joining method.

DETAILED DESCRIPTION OF THE INVENTION

As used in the following discussion, the terms "a" or "an" should be understood to encompass one or more, unless otherwise specified.

As used herein, the term "virus" could mean either the species of virus, or, interchangeably, an individual infectious unit which may contain nucleic acids and proteins. An individual infectious unit is also called a "viral particle" or a "virion", the latter terms being synonymous.

As used herein, a "strain" or "isolate" a virus means a collection of genetically homologous virions. Two viruses would be considered "homologous" if those viruses map to the same phylogenetic Glade. Two viruses would be considered "heterologous" if those viruses map to different phylogenetic clades. As the PRRS virus has a high mutation rate, it will be appreciated that a single PRRS strain comprises individual virions with related but variable genetic sequences. Thus, subpopulations of strains exist within each PRRS strain, and the genetic sequence of a PRRS strain is a consensus sequence such that the genetic sequence of an individual member of the PRRS strain may not be identical to the consensus sequence for that strain. A "consensus" sequence is a nucleic acid sequence in which each nucleic acid residue at a given position is present in >51% of the polynucleotides in a PRRS virus strain or isolate.

"Percent identity" can be determined by calculating the number of identical nucleotides or amino acids at the same positions in a nucleic acid or protein. Calculation of percent identity includes determination of the optimal alignment between two or more sequences. Alignment can take into account insertions and deletions (i.e. "gaps") in each of the sequences to be tested, such as, without limitation, in the non-coding regions of nucleic acids and truncations or extensions of polypeptide sequences. Computer programs and algorithms such as the Basic Local Alignment Search Tool (BLAST) may be used to determine the percent identity. BLAST is one of the many resources provided by the U.S. National Center for Biotechnology Information. Because the genetic code is degenerate, and more than one codon can encode a given amino acid, coding regions of nucleic acids are considered identical if the nucleic acids encode identical polypeptides. Thus, percent identity could also be calculated based on the polypeptide encoded by the nucleic acid. Percent identity could be calculated based on full length consensus genomic sequences or on a fraction of the genomic sequence, such as for example without limitation on individual open reading frames (ORFs).

As used herein, the term "modified, live virus" applies to any individual viral particle (i.e. a "virion") or to a multiplicity of viral particles whose genetic sequence has been altered from the genetic sequence of a naturally-occurring wild type virus yet still elicits protective immunity against wild type virus. Alterations include, without limitation, genetic mutations such as insertions and deletions of nucleotides and transitions and transversions which change one nucleotide for another nucleotide. Alterations can be accomplished by adapting a wild-type virus to replication in a tissue culture system, and continuing to passage a virus in a tissue culture system, whereby the virus accumulates genetic mutations. Alterations can also be accomplished using molecular techniques. Attenuated viruses form a subset of modified, live viruses.

As used herein, the term "attenuated" or "attenuation" means the ability of virus to cause or exacerbate clinical disease has been reduced or eliminated. An attenuated virus can still infect a host cell, either in vitro or in vivo, and that infection may result in subclinical effects in the host organism, but that infection does not result in one or more clinical disease symptoms.

In contrast, as used herein, "inactivated" viruses mean viruses which can no longer replicate in a host cell. Inactivated viruses are considered to be killed or dead viruses. Inactivation can be accomplished by a variety of methods, including but not limited to chemical alteration of viral proteins, to chemical or physical alterations in the structure of a virion, or to chemical or physical alterations in viral nucleic acids.

An "antigen" is any molecule capable of being specifically detected by the immune system of an organism. Typically a viral antigen is a viral protein encoded by the viral genome or derived from products of the viral genome. The presence of viral antigens can be specifically detected by the surface antigen receptors of both host T lymphocytes and host B lymphocytes and by antibody molecules synthesized by host cells.

"Immunogenicity" refers to the ability of an antigen to elicit an immune response, said immune response comprising both antigen-specific responses and non-antigen-specific responses or innate immune responses. "Protective immunity" is an immune response which can reduce or prevent clinical symptoms when an immunized animal is challenged or exposed to a pathogenic virus strain. As one skilled in the art would appreciate, protective immunity may decline with time or increased age of the immunized animal. Protective immunity as used herein should be effective for at least four months, but preferably at least six months, from the latest date of immunization. Protective immunity may be elicited with a single dose of a vaccine. A second or further dose may be used to increase or prolong the protective immune response. For example, increasing the protective immune response in a breeding sow may result in an increased level of maternally derived antibody in piglets.

In contrast to an antigen, an "adjuvant" is a non-specific stimulator of an immune response. An adjuvant could stimulate the innate immune response by binding and activating a pattern recognition receptor (PRR). Such stimulators of PRRs could be, for example, viral or bacterial nucleic acids, lipids from bacteria or parasites, or bacterial proteins or toxins, or any artificially-constructed mimic of such molecules. Adjuvants also include, without limitation: inorganic compounds that aggregate antigens to facilitate recognition by B lymphocytes or uptake by phagocytes, such as alum, aluminum hydroxide, aluminum phosphate, calcium phosphate hydroxide or ammonium sulfate; oils; and detergents. Adjuvants could also be host mediators of immune signaling, such as, without limitation, cytokines, lymphokines, chemokines, interferons, anaphylatoxins, growth factors, differentiation factors, and adhesion molecules.

As used herein, an "immunogenic composition" is a composition that elicits an immune response when administered to an animal. An immunogenic composition comprises at least one antigen and at least one pharmaceutically-acceptable excipient. The antigen can be a whole virus, bacterium, or other pathogen, either live or inactivated. The antigen can also be isolated, purified, or partially purified antigenic molecule from a virus, bacterium, or other pathogen. The antigen can be a polypeptide, a polysaccharide, a nucleic acid, or a lipid.

As used herein, a "vaccine" is an immunogenic composition which confers protection from, resistance to, prevention of, or reduction for a disease symptom when administered to an animal, wherein said symptom is caused by a pathogenic organism, for example a virus. A PRRS vaccine may include, without limitation, viral antigens or intact virions, either live or inactivated, in composition with at least one pharmaceutically-acceptable excipient.

As used herein, the terms "treating", "to treat", or "treatment", include without limitation restraining, slowing, stopping, reducing, ameliorating, or reversing the progression or severity of an existing symptom, disorder, condition, or disease. A treatment may be applied or administered therapeutically.

As used herein, the terms "preventing", "to prevent", or "prevention", include without limitation decreasing, reducing, or ameliorating the risk of a symptom, disorder, condition, or disease, and protecting an animal from a symptom, disorder, condition, or disease. A prevention may be applied or administered prophylactically.

As used herein, "administering to an animal" includes but is not limited to cutaneous, subcutaneous, intramuscular, mucosal, submucosal, transdermal, oral or intranasal administration. Administration could include injection or topical administration.

The term "pharmaceutically-acceptable excipient" refers to refers to those typically used in preparing veterinary and pharmaceutical compositions and should be pure and non-toxic in the amounts used. In certain embodiments, the pharmaceutical composition may contain excipients for modifying, maintaining or preserving, for example, the pH, osmolarity, viscosity, clarity, isotonicity, sterility, stability, adsorption or penetration of the composition. Some examples of acceptable excipients are found in, for example, Remington's Pharmaceutical Sciences and the Handbook of Pharmaceutical Excipients, $18^{th}$ Edition, (A. R. Genrmo, ed.), 1990, Mack Publishing Company and later editions and Remington: The Science and Practice of Pharmacy, Lloyd V. Allen, ed., Pharmaceutical Press, London, UK, $22^{nd}$ edition, 2012. and include diluents, vehicles, carriers, stabilizing agents, preservatives, solvents, suspending agents, emulsifiers, antimicrobials, antioxidants, buffers, chelating agents, complexing agents, carbohydrates, proteins, diluting agents, and/or pharmaceutical adjuvants. In certain embodiments, the primary vehicle or carrier in a pharmaceutical composition may be either aqueous or non-aqueous in nature. For example, a suitable vehicle or carrier may be water for injection, physiological saline solution with other materials common in compositions for parenteral administration.

As used herein, the term "porcine animals" refers to pigs, any of the animals in the genus Sus within the even-toed ungulate family Suidae.

The following experimental examples are illustrative of modified, live PRRS viruses. The following experimental examples are also illustrative of immunogenic compositions comprising modified, live PRRS viruses. The following experimental examples are also illustrative of using modified, live PRRS viruses to prevent or reduce porcine animals for symptoms of PRRS. It will be appreciated that other embodiments and uses will be apparent to those skilled in the art and that the invention is not limited to these specific illustrative examples or preferred embodiments.

Example 1

The objective of this study was to identify potential strains for development of vaccines. A total of 36 PRRS Type 1 field isolates have been evaluated for their potential as vaccines. Below is the preparation of pre-master seed viruses (Pre-MSVs) of four type 1 (European) PRRS virus (PRRSV-1) strains: DE 14-3073, ES 13-49, IT 14-32, and PL 14-02.

Initial isolation for PRRSV-1 strains was done using serum and lung tissues originating from pig herds diagnosed by PRRSV-positive test results during 2013 to 2014 in Europe. The pig herds were not vaccinated against PRRSV but experienced clinical signs characteristic for PRRSV infections, including reproductive failure in pregnant gilts and sows (i.e. late-term abortions, early farrowings, birth of weak and stillborn piglets and/or increased pre-weaning mortality) and/or growth retardation and respiratory disease problems in pigs of young ages.

Virus isolation was carried out in primary cultures of porcine alveolar macrophages (PAMs). To obtain PAM cultures 3-week-old piglets were used as donors. Briefly, lungs were obtained in aseptic conditions after the piglets were humanely euthanized and then flushed with phosphate buffer saline to retrieve PAM cells. The cell suspension obtained was centrifuged at 800×g for 15 minutes at 4° C. and the supernatant discarded. Pelleted cells were resuspended in Dulbecco's modified Eagle's medium (DMEM) and washed twice using DMEM as diluent after the above-mentioned centrifugation conditions.

The cells were counted and seeded in different supports (i.e. cellular culture flasks or plates of different sizes) at the final concentration of $3\times10^6$ cells/mL in DMEM supplemented with 10% fetal bovine serum (FBS) and antibiotic-antimycotic solution (100 units/mL of penicillin, 100 µg/mL of streptomycin and 0.25 µg/mL of amphotericin B). The cells were cultured at 37° C. in an atmosphere with 5% $CO_2$.

Clinical samples were processed following different procedures depending on their nature. Thus, serum samples were filtered through a 0.22 µm sterile syringe filter and kept at −80° C. until used for virus isolation. On the other hand, tissue samples, including tonsils and lungs, were homogenized 1:10 using DMEM as diluent. The homogenates were clarified by centrifugation at 2500×g for 15 minutes and the supernatants were filtered through a 0.22 µm sterile syringe filter and kept at −80° C. until used for virus isolation.

To infect PAM cultures the media was removed and the clinical samples (i.e. processed serum samples or processed tissue samples) were added in variable amounts depending on the support used. After 1.5 hours at 37° C. for adsorption, the cultures were washed and fresh DMEM supplemented as for cell maintenance was added. Cultures were observed daily for cytopathic effect (CPE). When CPE was observed, the cultures were harvested. After 3 cycles of freezing and thawing, cell debris was removed by centrifugation at 2500×g at 4° C. for 15 min and the supernatant was frozen and stored at −80° C. The presence of porcine reproductive and respiratory syndrome virus (PRRSV) in the culture was confirmed by reverse transcription and polymerase chain reaction (RT-PCR).

When no CPE was observed the culture was considered negative and the original clinical samples (i.e. serum samples or tissue samples) were used in a bioassay and inoculated to 3-week-old piglets housed in isolation. For this purpose, clinical samples were filtered and injected, by the intramuscular route, to the pigs. After one week, blood samples were taken from the exposed pigs to confirm viremia by RT-PCR. Pigs confirmed to be viremic were euthanized and blood, tonsil and lung samples were collected at necropsy and used as inocula for a second attempt of virus isolation in PAM cultures following the method previously described.

The growth of the PRRSV isolates in the MARC-145 cell line was attempted only for those isolates which grew well in PAMs and for which a seed stock could be produced. For this purpose, MARC-145 cells seeded in 25 $cm^2$ cell culture flasks at a concentration of $5\times10^5$ cells/flask and maintained at 37° C. in at atmosphere with 5% $CO_2$ in DMEM supplemented with 10% FBS and antibiotic-antimycotic solution (100 units/mL of penicillin, 100 µg/mL of streptomycin and 0.25 µg/mL of amphotericin B). Pre-confluent cultures were infected with the supernatants of positive PAM cultures following the same protocol described for the infection of PAM cultures. After adsorption, cells were washed and cultured in DMEM supplemented with 5% FBS and the previously mentioned antibiotic-antimycotic solution.

After the initial isolation, the viruses were amplified and primary virus stock (with a volume of at least 100 mL) were produced for each isolate in PAM cultures. For this purpose, PAM cells were cultured for 24 h at 37° C. in an atmosphere with 5% $CO_2$ in 75 $cm^2$ bottles at a concentration of $3 \times 10^6$ cells/mL in DMEM supplemented with 10% FBS and the antibiotic-antimycotic solution previously described. Then the medium was discarded, the cells were washed with fresh DMEM and the viral inocula were added. After 1.5 hours at 37° C. for adsorption, the cultures were washed and fresh DMEM supplemented as for cell maintenance was added. Cultures were observed daily for CPE. When most cells in a culture were killed, the cultures were harvested. After 3 cycles of freezing and thawing, cell debris was removed by centrifugation at 2500×g at 4° C. for 15 min and the supernatant containing virus was frozen and stored at −80° C. Virus titrations were calculated according to the method of the Reed and Muench (1938) and expressed as log $TCID_{50}$/mL. Viral stocks were kept at −80° C. and used in the different objectives of the study.

The same procedure were used with MARC-145 cell cultures. MARC-145 cell cultures were inoculated as previously described for initial isolation and maintained at 37° C. in an atmosphere of 5% $CO_2$. When CPE was evident (i.e. affecting approximately 70-80% of the monolayer) or after 5 days of culture if CPE is not observed, cultures are subjected to three cycles of freezing and thawing, clarified by centrifugation at 2500×g for 15 minutes and the supernatants used to inoculate fresh MARC-145 cell cultures. The remaining supernatant of each passage was stored at −80° C. A total of 60 passages in the MARC-145 cell line were undertaken for each PRRSV isolate.

On passages 30 and 50 viral stocks were cloned by plaque purification, following a standard methodology. Briefly, 6-well plates previously seeded with MARC-145 were inoculated when the cultures were pre-confluent with serial dilutions of each viral stock, from $10^1$ to $10^6$. After 1.5 hours of adsorption, the inoculum was removed from each well and the cells were covered with fresh DMEM media supplemented with 5% FBS, the abovementioned antibiotic-antimycotic solution and 1% low melting agarose. After 2-4 days of culture, depending on the isolate, individual plaques were selected under a phase contrast microscope and picked up. At least five plaques were selected for each virus in each purification round based on their complete isolation in the monolayer to guarantee the clonal nature of the selected viruses. Selected plaques were used as inocula for the next purification round. The procedure was repeated three times to assure that the obtained viral progeny derived from one single virus.

Example 2

The objective of this study was to further characterize the PRRS-1 isolates. The portion of ORF1 coding for nsp2 and ORFs 2 to 7 were amplified by RT-PCR using a set of primers previously designed. For this purpose, total RNA was obtained from all viral stocks using QIAMP® Viral RNA Mini kit (Qiagen, USA) following the manufacturer's instructions. For reverse transcription and polymerase chain reaction (RT-PCR), 15 µL of total RNA were used as template. The reaction was performed using a commercial one step RT-PCR kit (SuperScript III OneStep RT-PCR PLATINUM TAQHIFI®, Invitrogen, USA), following the manufacturer's instructions. RT-PCR products were purified using a commercial kit (QIAQUICK® Purification Gel Kit, Qiagen, USA) following the manufacturer's instructions. Individual sequences of both strands of DNA of each PCR product were determined using the same pair of primers used for RT-PCR, amplifying the samples by asymmetric PCR with fluorescent terminators and analyzing the products by electrophoresis on an ABI prism 310 Genetic Analyzer (Applied Biosystems, USA). At least two different RT-PCR products were sequenced to verify that no errors had occurred during DNA amplification and that the sequence obtained was correct. Sequences were manually corrected, purged of errors and aligned using Clustal Omega software. The sequences obtained were compared to the genotype 1 PRRSV prototype Lelystad virus and the vaccine strains which constitute the basis of the vaccines PORCILIS® PRRS (MSD Animal Health) (DV strain), UNISTRAIN® PRRS (Laboratorios Hipra) (VP-046 BIS strain) and INGELVAC PRRSFLEX® EU (Boehringer Ingelheim) (strain 94881). In addition they have been compared to the genotype 2 prototype strain VR-2332, which is the strain of INGELVAC PRRS® MLV vaccine (Boehringer Ingelheim), also commercially available in Europe.

The nucleotide similarity among the PRRSV isolates obtained was calculated as well as the similarity between each field isolate and the vaccine strains available at the time of isolation with the objective to confirm that the isolates were not related to one another and that they were not derivatives of commercially available vaccines at the time of clinical sample collection. Additionally, a phylogenetic tree was constructed using the neighbor joining method and including VR-2332, the prototype of the American genotype, as an outgroup to determine the subtype to which the European isolates belonged. To assess the statistical reliability of the dendrograms, bootstrapping values were calculated (random number seed: 123; 1,000 replicates). All phylogenetic analyses were performed with MEGA 5.0 software.

The PRRSV-1 was further attenuated by passing 10 times (to P70) in MARC-145 cells in the growth medium OPTI-MEM® I (Cat No. 31985, Life Technologies) supplemented with 2% fetal bovine serum (FBS; Cat No. 12003C and 12007C from Sigma and Cat No. 04-4000DJ from Gibco) and 50 µg gentamicin/mL (Cat No. 15750, Life Technologies) and by additionally passing 15 more times (to P85) in the same growth medium supplemented with 2% FBS without gentamicin. The identity of the 85th passage (P85) PRRSV-1 was confirmed by indirect immunofluorescence assay (IFA) using PRRSV-specific monoclonal antibody and the P85 PRRSV-1 was considered as the Pre-Master Seed Viruses (pre-MSV).

The following procedure was used to determine the titer of PRRSV-1. MARC-145 cells were seeded into 96-well plates at a density of 0.75 to $1.5 \times 10^4$ cells in 100 µL of growth medium (OPTI-MEM® I media supplemented with 5% FBS and 50 µg/mL gentamycin). Cells were incubated in 37±2° C. and 5±1% $CO_2$ incubator for 48-72 hours until cells were over 95% confluent. On the day of titration, all media was removed from the 96-well plate and replaced with 100 µL of fresh growth media.

Ten-fold serial dilutions of the PRRSV-1 were prepared with diluent (OPTI-MEM® I media, 50 µg/mL gentamycin) and transferred to corresponding wells on the plates prepared as above along with a negative control consisting of diluent alone and a positive control with a known titer.

Titration plates were incubated in 37±2° C. with 5±1% $CO_2$ incubator for 4 days. At the end of the incubation period, each plate was observed for the presence of virus-induced cytopathic effect (CPE) in each sample well using an inverted microscope. The 50% tissue culture infectious dose ($TCID_{50}$) was calculated using the Reed-Muench method and titer was recorded as $log_{10}$ $TCID_{50}$/mL. The titer range of P85 PRRSV-1 was 8.1-8.5 $log_{10}$ $TCID_{50}$/mL.

Example 3

The objective of this study was to determine the sequences of pre-MSV. To determine the genomic sequence of each virus isolate, viruses grown in MARC-145 cells were concentrated and purified by ultracentrifugation over a sucrose cushion and RNA was extracted using a MIN-ELUTE Virus Spin Kit (Qiagen) TRIZOL LS (Invitrogen). The full genome sequence was determined by multiple runs of next-Gen sequencing (NGS) using ILLUMINA® MISEQ® platform and/or NEXTSEQ500 system at Bioreliance (Rockville, Md.) and ACGT (Wheeling, Ill.). Variable and uncertain sequences and gaps were fixed and confirmed by Sanger dideoxy sequencing and consensus full genome sequences were generated. The nucleotide sequences were aligned and compared to selected known PRRSV-1 and commercial vaccine viruses by neighbor-joining tree nucleotide alignment tool using the software Geneious 10.1.3. (FIG. 1).

The PRRSV-1 MLV strains denoted as Pre-MSVs are deposited under conditions that will assure that access to the cultures during the pendency of this patent application to one determined by the Commissioner of Patents and Trademarks to be entitled thereto under 37 C.F.R. § 1.14 and 35 U.S.C. § 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it. A deposit of PRRSV-1 Pre-MSVs was entered into the permanent collection of the Patent Depository of the American Type Culture Laboratory, located at 10801 University Blvd., Manassas, Va., 20110-2209, USA, on Mar. 7, 2019 under the terms of the Budapest Treaty, whereupon the strains were assigned accession numbers PTA-125490 (DE 14-3073); PTA-125489 (ES 13-49); PTA-125488 (IT 14-32) PTA-125487 (PL 14-02); by the repository.

The safety and efficacy of immunogenic compositions and vaccines of modified, live Porcine Reproductive and Respiratory Syndrome viruses can be determined by methods well known in the art, including the dose response, onset of immunity, duration of immunity, and the shedding and transmission of a porcine reproductive and respiratory syndrome virus. The lack of reversion-to-virulence of any Pre-MSV can also be readily determined.

The cDNA consensus sequences for four PRRS virus isolates at passage 85 (P85) were deposited in GenBank genetic sequence database, an annotated collection of all publicly available nucleic acid sequences. The GenBank database is maintained by the National Center for Biotechnology Information (NCBI), part of the United States National Institutes of Health (NIH). GenBank is part of the International Nucleotide Sequence Database Collaboration.

The cDNA consensus sequence of PRRS strain DE14-3073 at P85 has been assigned GenBank Accession number MK024324 (SEQ. ID. NO:1). The cDNA consensus sequence designated SEQ. ID. NO:1 is:

```
atgatgtgta gggtattttc cctacgtgcg caacactttt tgtgtttgtg tgcctcggag    60
gcgtgggtat agccccgccc cacctcttgg ccctgttcta gcccaacagg tatccttctc   120
tctcggggcg agtgcgccgc ctgctgcttc cttgcagcgg gaaggacctc ccgagtactt   180
ccggagagcg cctgctttac gggatctcca ccctttaacc atgtctggga cgttctcccg   240
gtgcatgtgc accccggcgg ctcgggtgtt ttggaacgcc ggccaagtct tttgcacacg   300
gtgtctcagt gcacggtctc ttctctctcc agagcttcag gacctcagtt ttggtgcact   360
cggcttgttt tacaagccta aagataagct tcattggaaa gttcctgttg gtatacctca   420
ggtagagtgc actccatccg ggtgctgttg gctttcagct attttccctc tggcacgtat   480
gacctccggc aaccacaact ttctccagag acttgtgaag gttgctgacg ttttgtaccg   540
tgatggttgc ttggcgcccc gacatcttcg tgaacttcaa gtttacgagc gcggctgcag   600
ttggtacccg attacgggac ccgtgcccgg gatgggtctg tttgcgaatt ccatgcacgt   660
atccgaccag cctttccctg gtgccaccca tgtgctgact aactcgcctc tgcctcaaca   720
ggcttgtcgg cagccttttt gcccatttga ggaggctcat tctggtttgt tcaagtggaa   780
taaattcgtg atttttatag acccccccct taacgqtaga cgccgcatga tgtgggcacc   840
tgaatccgac gattcagcca acttggaggt gttgccgcct gaattagaac gtcaagttga   900
```

-continued

```
gattctcact cggagtttcc ctgctcacca ccctgtcaac ctcagcgact gggagctttc    960
cgactcccct gaacacggtt tttccttcag cacttatcat tcttctggtt acgttgccaa   1020
aaaccctgac gtgtttgata gcaagtgctg gctttcctgt tttctgagct tgtcgcctga   1080
ggtgtggcat cgtgaggagc tcttggctag cgcatttggt tatcaaacca agtggggcgt   1140
gcatggcaaa tacctccaac gcaggcttca aattaatggc atccgtgctg tggttgatcc   1200
agacggcccc attcacgttg aagcgctgtc ttgccccag tcttggatca ggcatttgac    1260
tctggacgat gaagtaaccc cagggttcgt tcgcctgacg tctcttcgca tcgtaccgaa   1320
cacagaacct accacctttc gcgtctttcg ttttggggcg cataagtggt atggtgccgc   1380
cggtaaacga gctcgcgcaa agcgtgctgc caagagcgag aaggactcgg ttactgcatc   1440
caaggctgtc caaccaactc ttgcctgtaa aaacaccacc tattcccccac caacggacgg  1500
gtcttgtggt tggcatgttc tcgccgccat aatgaaccgg atgttaaatg gtgacttcac   1560
gtccccttta accccgtaca acagaccaga agatgattgg gcatcggatt atgatccttgc  1620
tcaggcgatt caatgtctac aattacctgc taccatagtc cggaatcgcg cctgtcctaa   1680
tgctaaatac ctcataaaac tcaacggagt tcactgggag gtagaggcaa ggtctgggtt   1740
tgcccctcgc tcccttcccc gcgagtgtgt ggtcggtgtt tgctccgaag gctgtgtcgc   1800
aacaccctac ccagagaatg ggctgcctaa gcgggcactt gaggccttag cgtctgctta   1860
cagattgcct tccgattgcg tcagttctgg cattgctgac tttcttgctg accccccctcg  1920
ggagttttgg actcttgaca aaatgctgac ttccccatca ccggagcaat ccggcttttc   1980
tagtctgtac agattgctat tagaggttgt cccgcaaaaa tgcggtgcca cggaggggggc  2040
tttcatctat gccgttgaaa ggatgttgaa ggattgtcca agttccaagc aggccatggc   2100
tctcctagca aaagtcaaag tcccatcctc aaaggcctcg tctgtgacct tggatgagtg   2160
ttttcctacg gacgttccgg ccgacttcaa gccagcgtct catgagaagc ctcaaagttc   2220
cggtactgtt gttgtcctgt gttcaccggg agcagaagag tcagaaaaag tgaccctaga   2280
agaagttcgg gagggtggct ataaaaccat ctgccctgca ccccttactg agggtcctaa   2340
tgatgaacag gcacaagtag ctgtcggcga gcagctgagg ctcagcggtt gtggtttggc   2400
agccgggaac gctccagccc cggctggtcc aattgacaca gtaagcagag atcttcccct   2460
tccggacttc atgaaagaaa acatgtccaa taattgggag gatggaccat ggatttgtc    2520
ccaatcggca tcagctgtca tgacaacccc tgtaggagag cacacatcca aaaatccagg   2580
ttctggtatc ggtgacttcc ctgttactgt tcgaggcttt acctcaacgg ggctcgtact   2640
tcgtcacgtt gagcactgcg gtacggagtt gggcgacgac agtccgcctt tggatttgtc   2700
tgattcgcag acctcgaacc ggcctctgga tctatcccta gctgcttggc cagtgaagac   2760
caccgcatct gaccctggct gggttcatgg tagacgcgaa cctgtctttg taaagcctcg   2820
gaatgtttc tctgatggcg attcagttct tcagttcggg ggacctcctg aatctagctc    2880
tgtcaccgag tttgaccgga caaaagatac tccggcggtc gacacccttg tcaacttgac   2940
gactccaaac gaggccccccc ctgtaaccga ttctcgtgaa cttgccgaac tcaaacgccc  3000
gcgttttttcc gcacaagccc taattgaccg aggcggtcca ctcgctgatc tccatgcaga  3060
gataaaaat cggtatacg aacaatgcct ccaagcttgt gagcccggta gtcgtgcgac     3120
cccagccacc aagaagtggc ttgacaaaat gtgggatagg gtggacatga aacttggcg    3180
ctgcacctcg cagttccaag ctggtcgtat tcttgcatcc ctcagtttcc ttcctgacat   3240
gatccgagac acaccacctc ctgtacccag gaagagccgg gttagtgaca gtgtcggtct   3300
```

-continued

```
gaagcaacta gtgactcagt gggataagaa actgagtgtg gcccccccgag aagggcttat    3360 tgagtcagtg ctcgaccaaa ccgttccgcc gcccacggat gtccagcaag agataccac    3420 ccctccccat gaaccacccg atgcgccgga tttgcctggt cgagtgggta caagcagagg    3480
ttggaagggt cttacgcttt ccggcgcccg cctcgcgggg tctgtcagcc agcgcctcat    3540
ggcatgggtt tttgaagttt actcccatct cccagctttt atgctcacac ttttctcgcc    3600
gcggggctct atggcttcag gtgattggct ttttgcaggt attgttctac ttgctctctt    3660
gctctgtcgc tcttacccaa tactcgggtg cctacccttta ttgggtgtct tttctggttc    3720
tctgcggcgc gttcgtctgg gcgtatttgg ctcttggatg gcttttgctg tattttatt    3780 cacgactcca tccaacccag tcggttcttc ttgtgagcac gattcgccgg aatgtcacgc    3840
tgagcttctg gctcttgagc agcgccaact ttgggaacct gtgcggggcc ttgtggtggg    3900
cccctcaggt ctcctatgcg tcattcttgg taggttactc ggtgggtcac gttatctctg    3960
gcttgctttc ttacgtctat gcttgcttgc agatttggcc ttttctcttg tttatgtggt    4020
gtcccagggg cgttgccaca agtgctgggg aaagtgtata aggacagccc ccacggaggt    4080
ggctctcaat gtgttcccctt tttcgcgcgc cacccgttcc tctcttgtgt ccttgtgtga    4140
tcgattccaa acaccaaaag ggttgatcc ggtgttcttg caacaggtt ggcgcgggtg    4200 ctggtgtggt gagagcccca ttcatcaatc acaccaaaaa cccatagctt acgccaactt    4260
ggatgaaaag aagatatctg cccaaacggt agtcgctgtt ccatcgatc ctaaccaagc    4320 tatcaaatgc ctgaaagttt tgcaggcggg gggggccatt gtggaccaac caacacctga    4380
ggtcgttcgt gtatccgaga tcccctttc agctccgttt ttcccgaaag ttccggtcaa    4440
cccagactgc aaggtagtgg tagattcgga cacttttgtg gctgcggttc gttgcggtta    4500
ctcaacaaca caactggttt tgggtcgggg caattttgcc aagttgaatc aggcccctttc    4560 taaggcctct gcttacacaa aaacgactgg tggggcctct tatactttttg ctgtagttca    4620 agtgtctgtg tggactctta tccacttcat tctcggcctt tggttgatgt cgcctcaagt    4680
ttgtggtcga ggaacttccg acccatggtg ttcagatcct ttttcgtacc ccacttatgg    4740
cccaggcgtt gtgtgctcgt ctcaacttttg tgtatccgcc gatggtgtta ccctaccgtt    4800
gttttcggcc gtggcccgac tttctggcag ggaggtgggg atttttattt tagtgtttgt    4860
ctccttggct gctttagccc atcgctgggc ccttaaggct gacatgttag taatctttt    4920 agcgttttgt gcttacgcat ggcccatgag ttcctggcta atttgccttt tcccaacact    4980
cttaaggtgg atcaccctcc acccctctcac catactttgg gtgcattcat tcttagtgtt    5040
ctgcctgccg gctgccggcg ttctttcatt agggataact ggtcttctct gggcagttgg    5100
acgctttacc caagttgccg gacttatcac accttatgac atccaccaat atacttctgg    5160
gccgcgtggt gcaactgctg tggccacggc tccagagggc acttacatgg ccgccgtccg    5220
gagagctgct ctaactgggc gaactctaat cttcacccccg tctgcggtcg ggtcccttct    5280
cgaaggtgct ttcaggactc ataaaccttg cctcaacacc gtgaatgttg tgggttcttc    5340
cctcggttct ggaggagtct tcaccattga tggcaggaaa actgtcgtca ctgccaccca    5400
cgtgctgaat ggcgacacag ctagagttac cggtgactcc tacaaccgca tgctcacttt    5460
caagaccaat ggtgattatg cctggtccca tgctgatgac tggcagggtg ctgccccagt    5520
ggttaagatt acaaaaggat accgcggtcg tgcttattgg caaacatcaa ccggtgtcga    5580
gcccggtatc attggagagg ggttcgcctt ctgttttacc agctgcggtg actcggggtc    5640
gcctgttata tctgaagctg gtgaccttat cggcatccat actggttcaa acaaacttgg    5700
ttcaggtctt gtgacaaccc ctgaagggga gacctgctca attaaggaaa ctagactttc    5760
```

```
tgacctctct aagtattttg cgggtccgtg cgtccctctt ggggacatta agttaagccc    5820
tgccatcatt cctgacatga catctgttcc aagcgacttg gcatcgcttc ttgcttctgt    5880
ccctgtcatg gagggcggtc tctcgactgt tcaacttttg tgtgtctttt ttcttctctg    5940
gcgcatgatg ggtcatgctt ggacacccat cgttgctgtg ggcttctttt tgctgaatga    6000
aatccttcca gcagttttag tccgagccgt gttctctttt gcactctttg tgcttgcatg    6060
ggccaccccc tggtctgcac aggtgcttat gatcagactt cttacagcgt cccttaaccg    6120
gaacaagtct tctctggcgt tttacgcatt cggggggtgtc gtcggcctgg ctgctgaaat    6180
cggaaccttt gctggtaaac tacctgaatt gtctcaagct ctttcgacat actgcttttt    6240
gccaagattt cttgctgtat ctagttgtgt tcccatcatc atcatcggtg ggcttcatgt    6300
tctcggcgtg attttgtggc tattcaaata ccggtacctt catgacgtgc tggttggtga    6360
tgggagtttt tcaaaagcct tcttcctacg gtattttgct gagggcaatc tcagaaaggg    6420
tgtttcacaa tcctgtggca tgagtaacga gtccctaacg gctgctttgg cctgcaagtt    6480
gtcgcaagct gaccttgaat ttttatccag cttaacgaac ttcaagtgct ttgtgtctgc    6540
ctctaacatg aaaaatgctg ctggccagta cattgaagca gcgtatgcca aggccctgcg    6600
ccaagagttg gcctctctag ttcaggttga caaaatgaaa ggagttttgg ccaagcttga    6660
ggcctttgct gaaacagcca ccccgtctct agacacgggt gatgtgattg ttctgcttgg    6720
gcaacaccct cacggatccg tcctcgacat aaatgtgggg actgagagga aaactgtgtc    6780
cgtgcaagag accggagtt tgggcggctc caggtttagt gtttgtactg ttgtgtccaa    6840
taccctgtg gatgccttaa ccgacatccc acttcaaaca ccaacccccc tttttgagaa    6900
tggtccacgc catcgtagcg acgaagacga tcttaaggtt gagaggaaaa agaaacactg    6960
tgtgtccctc ggcttccaca acatcaacgg taaggtttac tgtaaaattt gggacaagtc    7020
caccggtgat acctttttaca cagatgattc ccggtatact caagaccatg tttttcagga    7080
caggtcagcc gactacaggg acaggggacta tgaaggtgtg caagccaccc ccccacaggg    7140
atttgatcca aaatctgaaa ccccggttgg cactgtcgtg atcggcggta tcacgtataa    7200
caggtatctg gtaaaaggta gagaggttct ggttctcaag cccgacaact gtcttgaagc    7260
cgccaggttg tctcttgagc aagctctcgc tgggatgggc caaacttgtg acctcacggc    7320
cgctgaagtg gaaaagctaa agcgtatcat cagtcaactt caaggcttga ccactgaaca    7380
agctttaaac tgttagccgc cagcggcttg acccgctgtg gccgcggcgg cttagttgtg    7440
actgaaacgc cggtgaaaat cataaaatac cacaacagaa cttccacctt aggccccttta    7500
gacttgaaag tcacatccga ggtggaggtg aagaaatcaa ctgagcaagg ccacgctgtt    7560
gtggcaaact tatgttccgg tgttgtcttg atgagacctc accaccgtc ccttgttgac    7620
gttctcttga acccggact tgacacgaca cctggtattc aaccggggca tggggccggg    7680
aatatgggcg tggacggttc tatttgggat tttgaaaccg cacctacaaa ggcggaactt    7740
gagttgtcca agcaaataat tcaagcatgt gaagtcaggc gcggggacgc cccgaacctc    7800
caactccctt ataagctcta ccctgttaga ggggatcctg aacggcataa gggtcgcctt    7860
atcaatacca ggttcggaga tttgcccttat aaaactcctc aggacaccaa gtccgcgatc    7920
catgcggctt gttgcttgca ccccaatgga gccccgtgt ctgatggcaa atccacgcta    7980
ggcaccactc ttcaacatgg ttttgagctt tatgtcccca ctgtgcccta tagtgtcatg    8040
gagtaccttg attcacgccc tgacacccct ctcatgctca gcaaacatgg tacttccaag    8100
gctgctgcag aagatctcca aaaatatgat ctgtccaccc aaggatttgt cctgcctggg    8160
```

-continued

```
gttctgcgcc tagtgcgcaa attcatcttc ggccacatag gtaaggcgcc gccattgttc    8220
cttccatcaa cctatcccgc taagaattct atggcaggga tcaacggtca gaggtttcca    8280
acaaaggatg tccagagcat acctgaaatt gatgagatgt gtgcccgtgc cgtcaaggag    8340
aattggcaaa ctgtgacacc ttgtaccctc aagaagcagt actgttccaa gcctaaaacc    8400
aggaccatcc tgggcaccaa caatttcatt gccctggctc acagatcagc actcagcggc    8460
gtcacccagg catttatgaa gaaggcttgg gagtccccaa ttgctttggg aaaaaataaa    8520
ttcaaagagc tgcattgcac ggttgccggc aggtgccttg aggccgatct ggcctcctgt    8580
gatcgcagca cccccgccat tgtaagatgg tttactgcca acctcctgta tgaacttgca    8640
ggatgtgaag accatttgcc cagctatgtg cttaactgct gtcatgacct cgtggcaaca    8700
caagatggcg ccttcacgaa acgtggtggc ctgtcgtccg gggatcccgt cactagtgtg    8760
tccaacaccg tgtattcact agtgatttat gcccagcaca tggtattgtc agccctgaaa    8820
atgggccacg agattggtct caagttcctc gaggaacagc ttagattcga ggaccttctt    8880
gaaattcagc ccttgctggt atactctgac gaccttgtct tgtatgctga aaacccact    8940 tttcccaatt accattggtg ggttgaacat ctcgacttga tgttgggttt caagacggac    9000
ccgaagaaaa ctattataac agacaagccc agcttccttg ctgcagaat tgaggcaggg    9060 cgacaactag tcccccaatcg tgaccgcatt ctcgccgctc ttgcatacca catgaaggca    9120
cagaacgttt cagagtatta tgcatctgct gctgcagttc ttatggattc atgtgcctgc    9180
atcgaccatg accctgagtg gtatgaggac ctcatctgcg gcatcgccag gtgcgctcgt    9240
caagatggct atagttttcc cggcccggca ttttttatgt ccatgtggga gagactgaaa    9300
agccacaatg agggaaagaa attccgccac tgcggcatct gtgatgccaa ggccgaccac    9360
gcgtccgcct gtggacttga cttgtgtctg tttcactcat attttcacca gcactgccca    9420
gtcactctgg gttgtggtca ctatgccggt tcaaaggaat gccagcagtg tcagtcacct    9480
attggaaccg gcaagtctcc tcttgacact gtgctgaaac aaatcccgta taaacctcct    9540
cgcactgtca tcatgagggt ggacaacaag acaacggccc tcgatccagg gagatatcag    9600
tcccgtcgag gcctcgttgc agtcagaaga ggcattgcag gcaatgaagt cgatcttgct    9660
gatggagact accaggtagt gccccttttg ccgacttgca aagacataaa tatggtgaag    9720
gtcgccagta atgtgctagt tagcaagttc atagtgggac cgccaggttc cggaaagacc    9780
acctggttat tgagtcaggt ccaggatgaa gatgtcattt acacacccac tcatcagacc    9840
atgtttgaca tagtcagtgc tctcaaagtt gcaggtatt ccataccagg ggcctcagga    9900 ctccctttc caccgcctgc caggtccggg ccgtgggtta agctcattgc cagcgggcac    9960
gtccccggtc gagtgtcgta cctcgatgag gccggatatt gcaatcattt ggatatactt    10020
agactacttt ctaaaacacc tctcgtgtgc ttgggtgacc ttcagcaact tcaccctgtc    10080
gggttcgatt cccactgtta tgttttgat caaatgcctc aggagcagct gaccactatt    10140
tatagatttg gtcccaacat ctgcacagcc atccagcctt gctacagaga aaaacttgaa    10200
tccaaggcta ggaacaccag gtggttttc accacccggc cagtgacctt tggtcaggtg    10260
ttaacaccgt accataaaga tcgcgttggc tctgcgataa caatagattc atcccaaggg    10320
gccacctttg atgttgtgac attacacttg ccatctccga atccctaaa taaatcccga    10380 gcacttgtgg ccatcactcg ggcgagacat gggttgttca tttacgaccc ccacaaccaa    10440
ctccaggagt ttttaacct gactcctgag cacactgatt gtaacctagt gttcagccgt    10500
ggggacgagc tggtggtttt gagtgcggat aatacagtca caactgtagc gaaggcccta    10560
gaggtgggtc catctcgctt ccgagtgtca gacccgaggt gcaagtctct tttggctgcc    10620
```

-continued

```
tgttcggcta gtctggaggg gagctgcatg ccgctaccac aagtggcaca caacctgggg    10680
ttttactttt ccccggacag ttcagcattt gcacctctgc cagaagagtt ggcgccacat    10740
tggccagtgg ttacccacca gaacaattgg gcgtggcctg accggcttgt tgccagcatg    10800
cgcccgattg atgcccgcta cagcaaacca atggtcggtg cagggtatgt agtcgggccg    10860 tccaccttc tcggcacccc cggtgtggtg tcatattatc tcacactata cgtcaaggt     10920 gagcctcagg ccttaccaga aacacttgtt tcaacaggac gtatagccac agactgtcgg    10980
gagtatctcg acacggctga agaagaggca gcaagggaac tcccccacgc attcattggc    11040
gatgtcaaag gtaccacgat tgggggatgt catcacatca catcaaaata tttgcccagg    11100
ttcctgccca aggactctgt tgccgtagta ggagtgagtt cgcctggtag agctgctaaa    11160
gccgtgtgca ctctcaccga tgtgtatctt cccgaactcc gaccatatct gcaacctgaa    11220
acggcatcaa aatgttggaa actcaagtta gatttcaggg acgttcgatt aatggtctgg    11280
aaaggagcta ccgcctactt ccagttggaa gggcttacat ggtcagcgtt gcccgattat    11340
gccaggttta ttcagctgcc caaggacgcc gtggtataca tcgacccatg cataggaccg    11400
gcgactgcca accgcaaggt tgtgcgaacc acggattggc gggccgacct ggcagtgaca    11460
ccgtatgatt acggggccca gcacattctg acaacagctt ggtttgagga cctcgggccg    11520
cagtggaaaa ttttggggtt gcagcccttc aggcgagcgc ttggccttga aaacaccgag    11580
gactgggcga ttcttgcgcg ccgtatgaat gacggcaagg attacattga ctacaattgg    11640
cattgcgtcc gaggacgccc acgcgctatc tacgggcgcg ctcgtgacca tacttaccat    11700
tttgccttgg gcacagaatt gcaggtggag ctgggtaaac cccaactgcc gcctgagctg    11760
gtaccgtgaa cctgaagtga tgcaatgggg ttgttatgga gtaaaatcag ccagctgttt    11820
gtggacgcct tcacagagtt ccttgttagt gtggttgata tcgtcatctt tcttgccata    11880
ctgtttgggt tcaccgtcgc agggtggtta ctggtctttt ttctcagatt ggtttgctcc    11940
gcgattctcc gttcgcgctc tgccattcac tctcccgaac tatcgaaggt cctatgaagg    12000
cctgctaccc aattgcaggc ctgatgtccc acaattcgca ttcaagcacc cattgggtat    12060
gctttggcac atgcgagttt cccaattgat tgacgagatg gtctctcgtc gtgtctacca    12120
gaccatggaa caatcaggtc aagcggcctg gaagcaggta gttggtgagg ccacccttac    12180
gaagctatca aggctcgatg tagttaccca cttccagcac ttggccgcaa cagaggcgga    12240
ttcttgccgc tttcttagct cacgactcgt gatgctaaag aatcttgccg ttggtaatgt    12300
gagcctacag tacaacacca cgtcagacca cgttgaactc atttttccca ctccaggtgc    12360
gaggcccaag ttgaccgatt tcagacaatg gctgatcagt gtccatgctt ctatttttc     12420 ctctgtggcc tcatctgtta ccttgtttgt ggtgctttgg cttcgagtcc caatgctacg    12480
ctatgctttt ggtttccatt ggctcacggc aacacatcat tcgagttaac tattaattac    12540
accatatgca agccctgcct caccagtcaa gcggctaaac aaaggcttga acctggtcat    12600
agcatgtggt gcaggatagg ggacaccagt tgtgaggaga gtgaccacga tgagttgtca    12660
atgaccatcc cgtctgggta cgataacctc aaactcgagg gctattatgc ttggctggcc    12720
ttcctgtcct tttcctacgc ggcccaattc catccggagc tgtttggaat agggaacgtg    12780
tcgcgtgttt ttgtggacaa gcgacaccag ttcatttgtg cggagcatga tggacccaat    12840
tcaaccgtgt ccattaatca taacatctcc gcatcgtacg cggtgtatta ccatcatcag    12900
gtagacggag gtaactggtt ccacttggaa tggctgcggc cgttcttctc ctcctggttg    12960
gtgctcaatg tctcatggtt tctgaggcgt tcgcctgcaa gccctgtttc tcgacgcatc    13020
```

```
tatcagatat taagaccaac acgaccgcgg ctgccggttt tatggtcctt caaaacattg 13080
aatgtctcca acctcacacg ggccccgcag cgcaagggac catcccccaa gcgaaacggt 13140
cacaatgtcg ccaagccgtc ggcactcccc agtacatcac gataacggct aacgtgactg 13200
acgaatcata cttgtataac gcagatttgc taatgctttc tgcgtgcctt ttctatgcct 13260
cagaaatgag cgagaaaggc tttaaagtca tctttgggaa cgtctctggc gtcgtttccg 13320
cttgtgtcaa tttcacggat tatgtggctc atgtgaccca acatacccag cagcaccatc 13380
tggtaattga ccacgtccga ttactgcatt tcttgtctcc atccacaatg aggtgggcta 13440
caaccattgc ttgtttggtc gccattctcc tggcgatatg aaatgttctc acagattggg 13500
gtgtttcttg actccgcact cctgcttttg gtggtttttt ttgctgtgta ccggcttgtc 13560
ctggtccttt gtcgatggca acggcaacag ctcgacatac caatacatat ataacttgac 13620
gatatgcgag ctgaacggga ccgcctggtt gtccagccac ttttcttggg cagtcgagac 13680
ctttgtgctt tacccagtcg tgactcatat tctctcactg gttttctca ccacaagcca 13740 tttttttgac gcgctcggtc tcggtgctgt gtccatcaca ggttttttg gcaaacggta 13800 cgtactcagc agcatctacg gtgcttgtgc tctcgcagcg ttcgtgtgct ttgccatccg 13860
tgctgctaaa aattgcatgg cttgccgcta cgcccgcacc cggttcacta acttcattgt 13920
agacaaccgg gggaggatcc atcggtggag gtctccaata gtggtggaga aattgggtaa 13980
agctgaaatt ggcagcgacc ttgtcaccat caaacatgtc atcctcgaag ggttaaagc 14040 tcaaccttg acaaggactt ctgctgagca atgggaagcc tagatggttt ttgtgatgag 14100
cctcccgctg cgcaaaatct tgtgctagcc tttagcatta catacacacc tgtaatgata 14160
tatgccctta aggtgtcacg cggtcgactc ctagggctgt tgcacatctt gatattcctg 14220
aactgctctt tcactttcgg gtatatgacg tatgtgcatt ttcagtctgc caaccgtgtt 14280
gcactcactt tgggggccgt tgttgccctc ctgtggggcg tttacagctt cacagaatca 14340
tggaagtttg ttacttccag atgcagattg tgctgcctag gccggcggta cattctggcc 14400
cctgcccacc acgtagaaag tgctgcaggt ctccactcaa tcccagcgtc tggtaaccgc 14460
gcatacgctg tgagaaagcc cggactaaca tcagtgaacg gcactctagt accaggactt 14520
cggagcctcg tgctgggcgg caaacgagct gttaaacgag gagtggttaa cctcgttaag 14580
tatggccggt agaaaccagg gccagaagaa aaagaaaagt acagctccaa tggggaatgg 14640
ccagtcagtc aatcaactgt gccagttgct gggcacaatg atgaagtccc agcgccagcg 14700
acctagggct ggacagacta aaaggaaaaa gtctgagaag ccacattttc ccttggctgc 14760
tgaagatgat attcggcacc acctcaccca gactgaacgc tccctctgct tgcaatcgat 14820
ccagactgct tcaaccaag cgcaggaac tgcgtcgctt tcatccagtg ggaaggtcag 14880
ctttcaggtc gagtttatgt tgccggttgc tcatacagtg cgcttaattc gcgtgacttc 14940
tacatccgct agtcaggatg caagttaatt cgacagtcag gtgaatggcc gcgattggcg 15000
tgtggccttt gagtcaccta ttcaattagg gcgatcacat gggggtcata cttattaggc 15060
aagatccatg tgaccgaaat t                                             15081
```

The cDNA consensus sequence of PRRS strain ES13-49 at P85 has been assigned GenBank Accession number MK024325 (SEQ. ID. NO:2). The cDNA consensus sequence designated SEQ. ID. NO:2 is:

```
atgatgtgta ggggagatac cctacacaca caacactcct ggtgtttgtg tgccttggag   60
gcgtgggtac agccccgccc cacctcttgg cccctgttct agcccaacag gtatcctttct  120 ccctcggggc gagtgcgccg cctgctgctc tcttgcagtg ggaaggacct cccgagtatt  180
```

-continued

```
tccggagagc acctgcttta cgggatctcc acccttaac catgtctggg acgttctccc    240
ggtgcatgtg cacccggct gcccgggtat tttggaacgc cggccaagtc tattgcacac    300
ggtgtctcag tgcgcggcct cttctctctc cagagcttca agacactgat ctcgctgcaa    360
ttggcttgtt ttacaagcca agaaacaagc ttcactggaa ggtccctatt ggcattcctc    420
aagtggagtg caccccatct gggtgctgct ggctctcagc catctttccc atagcgcgca    480
tgacctccgg caaccacaat ttacccaac gactcataaa ggttgccgat gtgttgtacc    540
gtgatggttg tttgactcgt caacaccttc gtgaacttca agtttatgag cgcggctgca    600
attggtaccc gattacgggg cctgtgcccg gagtggctgt gtatgcgaac tccatgcacg    660
tgtccgacca gccgttccct ggtaccaccc atgtgttaac gaacttgcct ttacctcaac    720
aggcctgtcg gcagccgttc tgtccatttg aggaggctca ttctaacgtg tataggtgga    780
atggactcgc gatttttgtg gattccactt ccgacggccg gtcccgcatg atgtggacac    840
cggggtctag cgactcgact gccttagaag tgctaccacc tggactagga cgtcaagccg    900
aaatcctcac ccggagtttt cctgcccacc accctgttaa cctcgctgac tgggagctca    960
ccgagacccc tgaatccggt ttctccttca gcatgtctca gtcttgtggt taccttgccc   1020
aaaaccctga cgtttttgat ggcaagtgct ggctttcctg ttttttgac ctgccgactg   1080 aggtatggcg tcgtgaggag catctggcta gtgccttcgg ttatcaaact aaatggggcg   1140
tgcatggcaa atacctccag cgcagacttc aaatcaatgg agttcgcgct gtagtcgatc   1200
ctgatggtcc tatccatgtt gaagcgttgt cttgccccca atcttggatc agacacctga   1260
ctctagacgg tgacgtgacc ccaggattcg ttcgcctgat gtctctccgt attgtaccga   1320
acacagaacc ggccactctc ccggtctttc ggtttggagc gcataaatgg tatggcgctg   1380
ccggcaaacg agcccgtgct aggcgtgccg ccagaaatgg gaaggactca gccactgccc   1440
ccacggccac ccaactgatc cctgcctgtg aacaaccac ttattccccg ccaacagacg   1500
ggtcttgtgg ctggcatgtt ctcgccgcca tagttaatcg gatgatgcat aatgattta   1560 catctcctct gactcagtat aacagaccac aggacgattg ggcgtccgat tatgaccttg   1620
ctcaggcaat ccagtgtatg cgactgcctg ctactatagt tcgtggtcgt gcctgccta   1680 acgccaagta ccttataaaa ctcaatggag tccattggga ggtagaggtg aggtctggaa   1740
tggctccgcg tcttctttct cgtgagtgca ttgttggcgt ctgctctgaa ggctgtatcg   1800
caacgcctta ccctgaaggc gagctacccg agcgtgcact agaggccttg gcggctgctt   1860
acagactacc ttccgactgt gtaagttctg gcattgccga cttccttgct gacccacctc   1920
ctcaggaatt ctggaccctc gacaagatgc taacctcccc gtcaccggag cggtccggtt   1980
tctccagttt gtataaatta ctattagagg ttgttccaca aaagtgcgga gctacggagg   2040
gggctttcgt ctatgctgtt gagaggatgt tgaaggactg cccaagctcc aaacaggcaa   2100
tggccctcct ggctaaagtc aaagtcccgt cttcgaaggc cccgtctgtg tccttggacg   2160
agtgtttccc cacggacgtt ccagccgacc ccgagccaac atctcaggaa aagcctcaaa   2220
gttctggcac taccacagtc ctgtgttcgc cgaatacaaa agagtctgag gaggtggcct   2280
tgcaaggcgt tcaggagagc agccacaagg ccgcccactc tgcagtcctt gttgaggaac   2340
ttagcgggaa gcgggcgcag gaggttgccg gcgagctaca ggagttcggc gactgtggct   2400
tggtaatcgg gagtgctcaa gacggcattc tggaggatga gccattggac ttgtcccgat   2460
cagcgttggg ggccacaacg attctcgtga gaaaccaaac acccaacaat tcgggttttg   2520
gcactggtac tcctcctgcc actgttcaag agcccgtctt tacagggctc atgtcttatt   2580
```

```
gcgttgagca ttgtaaaacg gagtccgata acagcagttt acctctggat ctgtctaatg  2640
cgcaaacctc ggaccagcct ttaaatctac ccttggctgc ttggccagtg agaaccaccg  2700
catctgaccc tggctgggcc cacggtaggc gtgtgcctgt ctttgtaaag ccccggggca  2760
ctctctccga tggcgattca gtccttctgt ttgggggggct ttccgaatcc agctctgtta  2820
tcgagtttga ccaatcgaaa gacgtcccag tgaccgatgc cccgtcgac ttgaccaccg  2880 cgaacggagc cctctctggg atcgactccc ttgaatttgc tgaactcaag cgcccgcgct  2940
actccgctca agctttgatt gaccgaggtg gtccactagc cgatgttcat gcaaagataa  3000
agagccgggt atatgaacaa tgccttcagg cttgtgagcc cggcagtcgt gcaaccccag  3060
ccaccaggga ttggctcaat aaaatgtggg aaagggttga tatgaagact ggcgctgta   3120 cttcgcagta ccaagctggt cacattctcg cgtctcttaa atttcttcct gacatgatcc  3180
aagacacgcc acctcctgtt cccaggaaga accgagctag tgatcatgcc gaaccaaaac  3240
gtctggtggc gcagtgggac aagaaattga gtgtggtctc ttccccaaaa ccggttgagc  3300
cagcgcctga ccggaccacc cctttgcctg cggacatcca gcaagagggt gttgcctcct  3360
ccgacagatt aacccgtgcg ccagacctcc ctagtcaagt gagcacgggc gggagttgga  3420
aagaccgcat gcttttcggc gctcgtttcg cggagtccat tggtcagcgc atcacagcac  3480 gggttttga aacttctcc catctcccag cttttgtgct cgcactttc tcgccgcggg     3540 gcgctatggc ttcaggtgat tggctgtttg caggtattgt tttacttgct ctcctgctct  3600 gtcgcccta cccagtactc gggtgcttac ccttactggg tgtcttttct gggtctgtgc   3660
ggcgtgttcg tctgggtgtt tttggttctt ggatggcttt tgctgtattt ttattctcga  3720
ctccacccga cccagtcggt tcttcttgcg ccacgattc gccggagtgt catgctgagc   3780
ttttggctct tgagcagcgc caactttggg aacctgtgcg cagccttgtt gttggcccct  3840
cgggtctcac gtgcgtcatt tttggtaggt tactcggtgg gtcacgttat ctctggcata  3900
ttctcctacg tttatgcatg cttgcagatt tggccctttc tcttatttat gtggtgtccc  3960
aagggcgttg tcacaagtgt tggggacagt gtataagaac agctcctgca gaagtggctc  4020
ttaacgtctt cccttttttg cgtgccaccc gtgcctctct cgtgtccgtg tgcgaccgat  4080
tccaatcgcc aaaaggtgtt gatcctgtgc acttggcaac cggctggcgt gggtgttggc  4140
gtggtgagag tcctatccac caaccacacc aaaagcccat agcttatgcc aatttagatg  4200
aaaagaaaat atccgccaaa acggtggtcg ctgtcccata tgatcccagt caggccatca  4260
aatgcctaaa agttctacag gcgggaggag ctattgtaga ccagcccacg ccagaggtcg  4320
ttcgcgtgtc tgaaatccct ttctcagccc catttttccc aaatgttccg gtcaacccgg  4380
attgcagggt tgttgtagac tcggacactt ttgtggcagc agtccgctgt ggttactcga  4440
cggcacaatt ggttttgggc caaggcaact tcgccaaatt aaaccaaatc ccccttggga  4500
gttccacctc taccagaacg actggcgggg cttcttacac ccttgctgtg gctcaagtgt  4560
ctgtgtggac cctcgttcat ttcattcttg gtctttggtt cacatcgcct caagtgtgtg  4620
gtcgggggac ctccgacccg tggtgttcaa atccttttc atatcccact tatggccccg  4680
gagttgtttg ttcctcacga ctctgtgtgt ctgccgacgg ggtcactcta ccattgtttt  4740
cagccgtggc gcagctctcc ggtagagagg tgggaatttt tgttctggtg ctcgtctcct  4800
tgattgctct agctcatcgt atggctctta aggcagatat gttagtggtc tttttggctt  4860 ttggggggtta cgcctggcct atgagctctt ggttaatctg tttctttcct ttactcctga  4920
agtggatcac tcttcacct ctcaccatgc tttgggtgca ctcgttttta gtgttttgtc   4980
tgcccgcagc cggcgtcctc tcgctgggga taactggcct cctttgggtg actggccgtt  5040
```

```
ttacccaggt agccggaatc atcacacctt atgacatcca tcagtacacc tctgggccgc   5100
gtggtgctgc tgctgtggcc accgcccag aaggcactta catggccgcc gttcggagag    5160
ctgcCctaac cgggcgaacc ttaatcttca ctccgtccgc agtcgggtct cttcttgaag   5220
gtgctttcag gactcgcaaa ccctgcccta ataccgtgaa tgttgttggt tcttccctcg   5280
gttccggagg agttttcacc attaatggaa agaaaatcgt cgtcaccgct acccatgtgt   5340
tgaacggcga tgcagccaga gtcactggtg actcttacaa ccgcatgcac actttcaaga   5400
ccaatggtga ttacgcctgg tctgatgcag acaactggca aggtgttgcc cccatggtca   5460
aggttgcaaa ggggtatcgc ggtcgtgcct actggcaaac atcaactggt gttgaacccg   5520
gtattgtcgg ggaaggtttc gccttttgct tcactaactg cggtgactcg gggtcacccg   5580
tcatttcaga gtccggtgac ctcatcggga tccataccgg ttcaaataaa ctgggctctg   5640
gccttgtgac aaccCctaac ggggagacct gttccatcaa agaaactaaa ctctctgatc   5700
tttccaagta ttttgctggc ccgagtgtcc ctctcgggga caccaagttg agcccgacca   5760
ttatccctga tgtgacatcc attccgagtg acttagcatc gctcctagct tccgtccctg   5820
taatggaagg tggtctttcg accgttcaac tcttgtgtgt cttctttctc ctctggcgta   5880
tgatgggtca tgcctggaca cctgtcgttg ccgtgggttt cttcttgcta aatgaaattc   5940
ttccagcagt tttagttcgt gccgtgtttt ccttcgcact cttgtgctc cgtggctta    6000 ccCcttggtc cgcacaggtg ctaatgatta gactcctcac agcgtccctt aaccgcaaca   6060
agctttcctt agcgttctac gcactcgggg gcatcgtcgg tttggctgct gaaattggga   6120
ctttcgctgg cagactgcct gatctgtctc aagctctttc gacgtactgc ttcctgccta   6180
gggtcattgc tgtgaccagt tgtgttccca tcatcatcat tggcgggctt catgctctcg   6240
gtgtgatctt gtggttgttc aaatatcggc acctccacgc catgttggtt ggtgacgggg   6300 cttttctcaag tgcattcttc ctgcggtatt ttgcagaggg taaccttagg aaggggggttt   6360 cgcagtcctg tggcatgagc aacgaatccc taacggctgc cttagcttgt aagttatcac   6420
aggctgacct agatttcctg tcaagcttga cgaacttcaa atgctttgtg tctgcttcaa   6480
acatgaagaa tgctgctggc caatatatcg aagcagcata tgccaaagct ctgcgccgag   6540
agctggcctc cctagtccag gtcgacaaaa tgaaggagt cttgtccaag ttggaagctt    6600
ttgctgagac ggccacccCg tcccttgaca caggtgacgt ggttgtgctg ctcgggcaac   6660
atccccatgg atctatcctt gacatcaatg tggggactga agaaaaaact gtgtccgtgc   6720
aagagactcg gaacttgggc ggctccaagt tcagtgtctg tactgttgtg tccaacacac   6780
ctgtggacgc cttgaccgat gttccgcttc aaacaccgac tccgctcttc gagaacggcc   6840
cgcgtcaccg ctgtgaggaa gacgatctta agtcgagag aatgaggaaa cattgtgtgt    6900
ctctcggctt ccacaatatc aatggcaaaa tttattgcaa agtctgggat aagtccactg   6960
gtgacacctt ttatacggat gattcccggt ataccaaga ctatgctttt caggacaggt     7020
cagccgacta cagagaccgg gactatgagg gtgtgcaagt cgcctctcaa caaggattcg   7080
acccaaagtc tgaaactcct gttggcactg tcatgatcgg cggcatcatg tataacaaat   7140
acctagttaa aggcagggaa atcttggtcc ttaaacctga caactgccta gaagccgcca   7200
ggctgtccct tgaacaggcc cttgctggga tgggccagac ttgtgatctc acagccaccg   7260
aagtggaaaa gctaaagcgc atcattagtc aactccaagg tctgaccact gaacaagctt   7320
taaactgtta gccgccagcg gcttgacccg ctgtggccgc ggcggcttgg ttgtaactga   7380
aacggcggta aaaattgtaa aataccacag cagaactttc actttaggcc ctttagactt   7440
```

-continued

```
aaaagtcgct tctgaagtgg aagtaaagaa atcaactgag cagggccatg ctgttgtagc    7500
aaatttaagt tctggtgtcg tcttgatgag acctcaccca ccgtcccttg tcgatgtcct    7560
cctgaaaccc ggacttgaca caacacccgg cattcaacca gggcatggag ccgggaacat    7620
gggtgttgac ggttctattt gggattttga aactgcaccc acaaaggcag aacttgaatt    7680
gtccaaacaa ataattcaag catgtgaggt cagacgcgga gacgcccga acctacaact    7740 cccttacaag ctctatcctg ttaggggga ccctgagcgc catgccggtc gtctcaccaa    7800
taccaggttt ggagatttgc cttacaagac tccaggagac accaagtctg ccatccatgc    7860
ggcttgttgt ctgcacccca acggggtccc cgtgtctgat ggcaagtcca cactaggcac    7920 taccccttcaa catggttttg agctttatgt tcccacagtg ccctatagtg ttatggagta    7980
ccttgattca cgctctgata cccctcctat gttcactaaa catggcactt ctaaggctgc    8040
tgcagaagac ctccaaaaat atgatttatc cacccaagga tttgtcctgc ctggggtcct    8100
acgccttgtg cgcagatttg tctttggcca catcggaaa gcaccgccgt tgttcctccc    8160
gtccacttac cctgccaaga actctatggc agggatcaac ggccagagat cccaacgaa    8220 agacgttcag agtatacctg aaattgatga atgtgtgcc cgcgccgtta aggaaaattg    8280
gcagaccgtg acgccctgca ccctcaagaa acagttctgt tccaagccca aaaccaggac    8340
cattctgggc accaacaact ttattgccct ggctcaccga tcggcgctca gtggcgtcac    8400
ccaagcattt atgaagaagg cttggaagtc cccgattgcc ctggggaaaa acaaattcaa    8460
agagctacat tgcactgttg ctggcaggtg tcttgaggct gatttggcct cctgtgatcg    8520
tagcaccccg gccatcgtga ggtggtttgc tgccaacctc ctgtacgagc ttgcagggtg    8580
tgaagagtac ttgcctagct atgtactcaa ctgctgccac gacctcgtgg caacacagga    8640
tggtgccttc acaaaacgcg gtggtttgtc atccggtgac cctgttacca gtgtgtcaaa    8700
caccatatat tcactggtga tctatgccca gcacatggtt ttgtcagcct taaaaatggg    8760
tcatgagatt ggtcttaagt ttctcgagga acagctcaaa ttcgaagacc tcctcgaagt    8820
ccagcccatg ttagtgtact ctgacgacct agtcttgtac gccgaaaggc ccaccttccc    8880
taattaccac tggtgggtcg aacaccttga cctaatgctg ggtttcaaaa cggacccgaa    8940
gaaaactgta ataactgata agcccagctt cctcggctgt aaaattgaag cagggcggca    9000
gctagttccc aatcgcgacc gtatcctagc cgctcttgca taccacatga aggcgcaaaa    9060
cgcctcagaa tattatgcat ctgctgctgc gatcctaatg gattcgtgtg cttgcattga    9120
ccacgatcct gagtggtatg aggacctcat ttgtggtatt gcccggtgcg ctcgccaaga    9180
tggctatagt tttccaggcc cggcatttt catgtcgatg tgggaaaaac taaagagcca    9240
caacgaaggg aaaaaattcc gccactgcgg tatctgtgat gccatggccg atcatgcatc    9300
tgcctgtggg cttgatttgt gtttgtttca ttcgcatttt caccagcatt gtccagtcac    9360
tctgaactgc ggtcaccgtg ccggcgcaaa ggaatgtccg cagtgccagt cgccagttgg    9420
ggttagcaaa tcccctctcg acactgtgct agaacaaatt ccatacaaac cccctcgtac    9480
tgtcattatg aaggtgagtg atagaacgac tgtcctcgac ccgggcaggt accagtcccg    9540
tcgtggtctt gttgctgtta agaggggcat tgcaggcaat gaagttgatc ttcctgatgg    9600
agactaccaa gtggtgcctc tcttaccaac ttgcaaagat ataaacatgg taaaggtagc    9660
ttgcaatgta ctgctgagta agttcatagt aggaccacca ggttccggaa aaaccacttg    9720
gttactgagt caagtccagg acgacgatgt catttacaca cccacccatc agaccatgtt    9780
tgatatagtc agtgctctca aggtttgcag gtattctatt ccaggggcct ctgggctccc    9840
cttcccacca cctgccaggt ctgggccgtg ggtcaggctt gttgccagcg ggcacacccc    9900
```

```
cggccgagtg tcatacctcg atgaggccgg gtactgcaac catctggaca ttcttaggtt   9960
gctttccaaa acaccccttg tgtgtctggg tgaccttcag caacttcacc ccgtcggctt  10020
taattcctac tgctatgtgt ttgatcagat gcctcaaaag cagctgacca ccatttacag  10080
gtttggcccc aacatctgtg cagccatcca gccttgttac agggaaaaac ttgaatccaa  10140
ggccaggaac accaggatag tttttactac acggcctgta gctttcgggc aggtcctgac  10200
accataccac aaagatcgca tcggttcagc gataaccata gattcgtctc aggggccac   10260 ttttgacatt gtgactttgc atttaccatc gccaaagtcc ctgaataaat cccgggcact  10320
tgtggccatc actcgggcaa ggcacgggtt gttcatctac gaccctcaca atcagcttca  10380
ggagtttttc aacctagctc ctgagcgtac tgattgtaac cttgtgttta accgtgggga  10440
tgagctagta gtcctgaact cggacaatgc agtcacaacc gtggcgaaag ccctagaggc  10500
aggcccatct cggtttcgag tatctgatcc gaggtgcaag tctctcttgg ccgcttgctc  10560
ggccagccta aagggagct gcatgccgct gccgcaagtg gcgcacaatc tggggttcta   10620
cttctcccca gatagcccag catttgcacc cctgccgaaa gaactagcgc cacattggcc  10680
ggtggtcact catcagaaca accgggcatg gcctgaccga cttgttgcta gcatgcgtcc  10740
aatcgatgcc cgttacagca agccaatggt cggcgctggg tatgtggtcg ggccatccac  10800 tttttctcggc acccccggcg tggtgtcata ttatctgacg ctgtacgtca ggggtgagcc  10860
ccaggccttg ccagaaacac tcgtgtcaac ggggcgcata gccacagact gtcgagaata  10920
tctcgacgcc gctgaggaag aggtagcaaa agaactaccc cacgcattca ttggtgatgt  10980
caagggtacc acggttgggg ggtgtcatca catcacatca aaacacctac ctaggttcct  11040
acctaaggat tctgttgccg tggttggagt aagttcaccc ggcaaggctg ctaaagccgt  11100 gtgcacccctt actgatgtgt acctaccgga actccggcca tatttgcaac ctgagacagc  11160
gtcaaagtgc tggaagctca aactggactt cagggatgtc cgtctgatgg tctggaaagg  11220
ggcaaccgcc tatttcaat tagaagggct cacatggtcg gcgctgcccg actatgccag  11280
gtttattcag ctgcctaagg aagccgtggt gtacatcgat ccgtgtatag gaccggcaac  11340
agccaaccgc aaagtcgtgc gaaccacaga ctggcgggct gacctggcag tgacaccgta  11400
tgattacggt gctcagtata tttgacaac agcctggttc gaagacctcg gccacagtg   11460 gaaaattctg gggttgcaac cttttaggcg atcgcttggc tttgagaaca ccgaagattg  11520
ggcaatcctt gcacgccgta tggatgacgg caaagattac atcgactaca actggaattg  11580
tgttcaaaac cgtccacttg ctatccacg gcgcgctcgt gaccacacat atcacttcgc  11640
cctcggcaca gagttgcagg tggaactggg caaaccccgg ctgccgccgg agcaagtgca  11700
gtgaacccgg agtgatgcaa tggggtcact gtggagtaaa atcagccagt tgttcgtgga  11760
cgctttcact gagttcctcg ttagtgtggt tgacattgtc attttccttg ccatactgtt  11820
tgggttcaca gtcgccgggt ggctactggt cttcctttc agaatggttt gctccgcgat  11880
tctccgttcg cgctctgcca tttactctcc cgaactatcg aaggtcctat gaaggcctgc  11940
tacccaactg caggccagat gtcccacaat tcgcattcaa gcatccactg ggcttgcttt  12000
ggcatatgcg agtttcccat ttgattgatg aaatggtctc ccgtcgtatt taccagacta  12060
tggaacattc aggtcaagcc gcttggaagc aagtggtcgc tgaggctacc ctcacaaaac  12120
tatcaaggct tgacgtagtc actcattcc aacatctggc cgcggtggag gcggattctt   12180
gccgcttcct cagctcacga cttgcaatgt tgaaaaacct tgccgttggc aatgtgagct  12240
tgcagtataa caccacattg gacagagttg agctcgtctt ccctacgccg ggttcgagac  12300
```

```
ccaagttgac tgatttcaga caatggctca tcagtgttca cgcttccatc ttctcttctg 12360
tagcttcgtc tgtcaccttg ttcatagtgc tctggcttcg aattccagcc ttacgctatg 12420
tttttggttt ccattggccc acggtaatac atcattcgag ctaaccatca actatacaat 12480
atgtatgccc tgtcttaccc gccaagcggc tagtcagagg ctcgagcctg ccgcaacat 12540 gtggtgtaga atagggtacg acagctgtga agaacgtgac catgatgagc tgtcaatgtc 12600
catcccgtct gggtacgaca acctcaaact cgagggttat tacgcttggc tggcattctt 12660
gtccttctcc tacgccgctc aattccatcc agaattgttc ggaataggga atgtgtcacg 12720
cgttttcgtg gacaaacaac accaagccat ttgtgctgtg catgacggac aaaattccac 12780
catatccgct gagtacaaca tttctgcatt gtacgcggca tactaccacc accaagtaga 12840 cggggggcaac tggtttcatc tagaatggct gcggccattc ttttcttcct ggctggtgct 12900
caatatttca tggtttctga ggcgttcgcc tgcaagccct gcttctcggc gcatctatca 12960
gatgttaaga ccaacacaac tgcggctgcc ggtttcatgg tccttcagaa cattgaatgc 13020
cttcgacacg gagcctcaac aacgcaaaat ggcccttccc ttcggaagcc gtcgcaatgt 13080
cgtgaagccg ttggcacccc tcagtacatc acaattacgg cgaatgtgac cgatgaatca 13140
tatttgtaca acgctgactt gctgatgctt tctgcgtgcc tcttttacgc ctctgaaatg 13200
agcgagaaag gcttcaaagt catcttcggg aacgtttctg gcgttgtctc tgcctgcgtt 13260
aattttacag actatgtggc ccatgtgact caacacaccc agcagcatca cctggtaatt 13320
gatcacattc gattgcttca cttcttgtca ccgtctgcaa tgaggtgggc tacaaccatt 13380
gcttgcttgc tcgccattct cttggcgata tgagatgttc tcacaaactg gagccttcct 13440
cgactccgca ctcttgctcc tggtggcttt ttttgctgtg taccggcttg ttctggtcct 13500
ttgccgatgg caacggcaac agcccgacat accaatacat atataacttg acgatatgcg 13560
agctgaatgg gaccgagtgg ttgtctaacc attttaattg ggccgtcgaa acctttgtgc 13620
tctacccagt cgcaactcac attatttcac tgggttttct tacaacaagt catttccttg 13680
atgcgctcgg tctcggcgct gtgtccgtca ccggatttta caacaaccgg tatgtgctaa 13740
gcagtgtcta ctgcgcctgt gcttttgcag cactcgtgtg ctttgtcatc cgtgccgcta 13800
aaaattgcat ggcttgccgc tatgcccgca cccggtttac taatttcatc gtggacaacc 13860
gggggaggat ccaccgatgg aagtctccaa tagtggtgga gaagttgggg aaagctgagg 13920
ttggtagcga ccttgtcacc atcaaacatg ttgtccttga aggggttaaa gctcaacctt 13980
tgacgaggac ttcggctgag caatgggaag cttagacaat ttttgcggtg atcctgccgc 14040
cgtacaaaag cttgtgctgg cctttagcat tacatataca cctataatga tatacgccct 14100
taaggtgtca cgcggccgac tcttaggact attgcacatc ctaatattct tgaattgttc 14160
tttcacattt gggtatatga cttatgcgca ttttcaatcc accagtcgtg tcgcgcttgc 14220
tctgggggct gttgtcaccc tcctgtgggg catttacagt cttacagagt catgaagtt 14280 tgtcgcttcc agatgcagaa tgtgttgtct aggccggcga tacatcctgg ccctgccca 14340 tcacgtagaa agtaccgcag gtctccattc aatcccagcg tttggcaacc gagcatacg 14400 tgtgagaaag cccggactaa catcagtgaa cggcactctg gtaccaggac ttcggagcct 14460
cgtgctgggc ggcaaacgag ctgttaaacg aggagtggtt aacctcgtca agtatggccg 14520
gtaaaagcca gagccagaag aaaaagaaaa atacagctcc aatggggaat ggccagccag 14580
tcaatcaact gtgccaattg ctgggttcga tgataaggtc ccagcgccag caacctagga 14640
gaggacaggc gaaaaaaaga aagcctgata agccacattt tccctagct gctgaagatg 14700 acattcggca ccacctcacc cagactgaac gttccctctg cttgcaatcg atccaaacgg 14760
```

-continued

```
cttttaacca aggcgcaggt gttgcgtcgc tttcatccag cgggaaggtc agttttcagg   14820
ttgagttcat gttgccggtt gctcatacag tgcgcctaat tcgcgtgact tctgcatccg   14880
ctagtcagaa tgtagattaa tttgacagtc aggtgaatga ccacgattga cgtgtggcct   14940
ctaagtcacc tattcaatta gggcgatcac atggggtca aacttaattg ggcgagaacc    15000
atgtgaccga aatt                                                      15014
```

The cDNA consensus sequence of PRRS strain IT 14-32 at P85 has been assigned GenBank Accession number MK024326 (SEQ. ID. NO:3). The cDNA consensus sequence designated SEQ. ID. NO: 3 is:

```
atgatgtgta gggtatcccc cttgttttg cagcactcct agtgtttgtg tgcctcggag    60
gcgtgggtac agcccccgccc cacctcttgg cccctgtcct aacccgacag gtacccttct   120
ccctcggggc gagcgcgccg cctgctgctt cttgcggcg ggaaggacct cccgagtatt    180
tctggagagc acctgcttta cgggatctcc accctttaac catgtctggg atgttctccc    240
ggtgcatgtg caccccggct gctcgggtgt tttggagtgc cggtcaagtc tattgcacac    300
ggtgtctcag tgcacggcct cttctccctc cagggctgca agacactgac ctcgcagcaa    360
ttggcttgtt ctacaagccc aaagataaac ttcactggaa agttcctatc ggcatccctc    420
aggtggagtg tactccgtct ggatgctgct ggctctcggc catcttcccc ttggcgcgca    480
tgacctccgg caaccacaac ttttctcagc gactcataaa agttgccgaa gtgttgtacc    540
gtgatggctg tttgactccc cgacaccttc gtgagcttca agtttacgag cgtggttgca    600
gttggtaccc gatcaccggg cccgtgcccg gagtaggtgt gtacgcgaac tccatgcacg    660
tgtccgatca atcgtttcct ggtgccactc atgtgctgac gaacttgcct ctacctcagc    720
aagcttgtcg acagcctttc tgtccattcg atgaggcccg ctctgacgtg tacaagtgga    780
acgaatttgt ggttttcgtg gattcctcct ccggcggtca attacgcatg atgtggatgc    840
cgggatccga tgattcggtc gccattgaag cattatcgcc tgagttggaa cgtcaggttg    900
aaatccttgt tcggagtttc cctgccccac ccctgttaa cattgccgac tgggagcttg    960
ctgagtcccc ggagcacggt ttttccttcg gcacgtctca tcctagtggt taccttaccc   1020
gagacccttg gggttttgat ggcaaatgtt ggctctcttg cttcttgggc ctcccgacta   1080
gagttcagca tcatgaggag tacctagccg acgccttcgg ttaccaaacc aagtggggcg   1140
tgcacggtag gtatcttcag cgcaggcttc aagtcaacgg tgtccgtgct gtggttgatc   1200
ctgacggccc catccacgtt gaagcgctgt cttaccccca gtcttggatc aggcacctga   1260
cttttgacga tgatgttacc ccaggattcg ttcgcctgat gtctcttcgc attgtgccga   1320
atacagaacc taccactctc ccaatttcc ggttttgggc gcataaatgg tatggagcag    1380
ctggcaaacg agctcgcgcc aagcgtgctg ccaaaaacaa gggggattcg aattccaccc   1440
ccgaagtcgc ccgagtggct tctaccagtg aggttgttac ctattcccca ccggcagacg   1500
ggtcttgtgg ctggcatgtt gttgccgcca tgatgaacca catgatgaac ggtaaactca    1560
cgtcccttt gactccgtac aacagaccag aggacgactg ggcttctgat tatgatcttg    1620
tcaagataat tcaatattg caactgcccg caaccgtagt tcgggcccgt acttgtccca    1680
acgctaagta ccttgtcaaa ctcaatgggg tccattggga agttgagatg aggccagaag    1740
tagctccttg ctctcttcc cgcgaatgtg tggttggtgt ctgttctgag ggctgtgttg    1800
cgtcgcctct tccagaaggg gggctgcctg accgcgcact tgaggccctg gcgtccgctt    1860
acagattgcc ttccgactgc gttggtgatg ctgttgctga cttcctctcc agcccgcct    1920
```

-continued

```
ctcaagaatc ctggaccctc gataaaatgt tgacctcccc atcaccagag cagtccggtt    1980
tttctagctt gtacaaactg ctactggagg ttgttccgca gaagtgcgga gccacggagg    2040
gggccttcgt ctatgctgtt gagaggatgc tgaaagattg tccgagcccc aaacaggcca    2100 tggcccttt gggaaaaatc aaatcccat cctcaaaagc ctcgtccgtg tccttagacg      2160
agtgctttcc cactgatgtt ttgcaagagg gtaaccacag gacctcccac cccgtggctc    2220
ctgctgatgg acttgacaaa cagcaagcac cgttggttga ggatgaacaa ttaggattcg    2280
gtggtcacga ttcggccgtt gcggcggtca gtggcaatca ggagagtgaa ccgttggacc    2340
tttcccgatc ggcaccagtt gtaacaacga ccttcgtcga agggcgagtg cccggcgacc    2400
cgggcccctg caccagcgac cgctccgctg ttgttcaaga gttagttgag cgatgtgacg    2460
cggagtcaaa tgacggcagt ttgccctgg atgtgactaa agtgcaaacc cccaatcaac     2520
ctctggatct atctctagct gcttggccag tgaagaccac tgcatctgac cccggttggg    2580
ttgacggtag acgcgaaccc gtcttcgtca agcctcgcgg tgctttctct gacagtgagt    2640
cggtcttccg gtttggagga gtttctgaga ccggccctgt catcgggttt gatcgggtaa    2700
aagaaattcc ggcggctgac accccatcg acttaacaat ctcaaaagag actctttccg     2760
gggcagaccc ctctgagttc gccgcactta agcgcccgcg tttctccgct caagccttga    2820
ttgaccgagg tggcccactt gctgatgcct gtgcaaagat aaagaatcga gtgtatgagc    2880
ggtgcctcca ggcttgcgaa cctggcagtc gtgcgactcc agccacaaag gagtggctcc    2940
acaagatgtg ggaagggtc gacatgaaga cttggcattg tacctcgcag ttccaaacag     3000
tctatattct cgggcccctt aaattcctat cagatatgat tagtgacacg ccacctcctg    3060
tccctaggag ggatcggttt agtgacagtg ccagcttgaa acaattagcg gcacagtggg    3120
atgagaaatt gaacacagtc cccccccaag ggccggttga gccggggctt agtcgagccg    3180 cccctcgcc tgcgaatgcc cagcgagaag gcatcaaccc ctccgatgag ccaccccaaa     3240
cgccgaaccc ctctggacaa actgttgctg atggggtgt caaaagactt gtgtccttcg     3300
gcgtccgcct tgtagggtcc accagccagc gccttatgac atgggttttt gaaatttact    3360
cccatctccc agcttttatg ctcacactat tctcgccgcg gggctctatg gttgcaggtg    3420
attggttgtt tgcaggtgtt gtgttacttg ctctcttgtt ttgtcgttct tacccagtgc    3480
tcggatgcct tcccttattg ggtgtctttt ctggttctgt acggtgtgtt cgtctgggcg    3540
tttttggttc ttggatggct tttgctgtat ttttattctc aactccaacc aacccagtcg    3600
gttcttcttg tgaccacgat tcgccggagt gtcatgctga gcttttggct cttgagcagc    3660
gccaactttg ggaacctgtg cgcggccttg tggtggggcc ctcgggcctc ctatgcgtca    3720
ttcttggcaa gctactcggt gggtcacgtt atctctggca tgttctctta cgtttatgca    3780
tgcttgcgga tttggccttt tctcttattt atgtggtgtc ccaagggcgt tgtcacaagt    3840
gttggggaaa atgtataagg acggctccag ccgaggtggc cctcaacata ttccctttct    3900
cacgtgccac ccgtgcttcc cttgtatcct tgtgcgatcg gttccaagcg ccaaaagggg    3960
ttgaccccgt acacttggca acagggtggc gcggtgttg gcgcggtgag agccctattc     4020
atcaggcgca ccagaaacct atagcttatg ccaacttgga tgaagagaaa atatccgccc    4080
aaacagtggt tgctgtccct tatgacccca gtcaggccgt caaatgtttg aaagttctgc    4140 aggcggggg ggccatcgta gatcagcccg tacctgaagt ggtccgtgtg tccgagatcc     4200
ctttttcggc tccattcttc ccaaaagttc cagtcaaccc agattgcagg ttgtggtgg    4260 attcggacac tttcgtggct gcagtccgct gtggttactc gacaacgcaa ctggtcttgg    4320
gtcaaggcaa ctttgccaag ttgaacaaca cccctctcaa gaattccgtt tccaccaaga    4380
```

-continued

```
cgattggagg ggcctcttac acccttgccg tggttcaggt gtccgtgtgg actcttgttc   4440
attttgtaat cggtctttgg ttaatgtcgc ctcaagtgtg tggccgaggg acctctgacc   4500
cttggtgctc aaatccttt tcatatccta cttatggtcc cggggttgtg tgttcctccc    4560
ggctttgtgt gtctgccgat ggagtcactc taccattgtt ttcagctgtg gcccaactgt   4620
ctggtagaga ggttgggatc tttattttgg tgtttgtctc tttaatcgcc ttggctaacc   4680
gcctagctct taagtctgac atattagtgg tatttctggc actttgtgct tatgcttggc   4740
ccatgagctc ctggctaatc tgtttctttc ctatactctt gaggtggatc accctccacc   4800
ctcttaccat gctttgggtg cattcgttct tagtattctg tttgccagcc gccggtgtcc   4860
tgtcaatagg ggttactggc tttctttggg cgattggtcg tttcacacaa gtcgccggaa   4920
ttatcacacc ttatgacatt catcaataca cctccgggcc acgcggtgcg gctgctgtag   4980
caacggcccc agagggtact tacatggcag ccgtccggag ggccgccctg accggacgga   5040
ctttaatttt tacccatcct gcagttgggt ctctccttga gggcgctttc aggacccaca   5100
agccctgtct caacaccgta atgtcgtag gttcttccct cggttctgga ggggtcttca    5160
ctatcgacgg cagaaagact gtcattactg ctgcccatgt attgaacggt gacaccgcta   5220
gggtcaccgg cgactcctat aatcgcatgc acactttaa aaccaatggt gattatgcct    5280
ggtcccatgc tgacgattgg cagggcccct ctcccatagt caaagtcgcg aagaggtatc   5340
gcggccgcgc ttactggcaa acatcgactg gtgtcgaacc aggcatcatc ggggaagggt   5400
tcgctttctg tttcaccaat tgtggcgatt caggttcacc tgtcatctct gaagctggcg   5460
acctcatcgg gatccatact ggttcaaata aacttggatc tggacttgtg accgcccctg   5520
acggggaaac ctgctccatc aaagagacca aactttctga cctatctagg tactttgcag   5580
gtccaagcgt ccctctcgga gacataaagt tgagtccagc tatcatccct gatgtggcct   5640
ctgtcccgag tgacttggca tcacttcttg cttccgtgcc tgtgatggag ggcggccttt   5700
cgaccgttca acttctgtgt gttttcttcc ttctttggcg catgatgggc catgcctgga   5760
cccccgtcgt tgctgtgggc ttcttttttgc tgaacgaaat cctcccagca gtcttagtcc   5820
gcgctgtgtt ttcttttgca ctctttgtgc ttgcatgggc cacccctgg tctgcacagg    5880 tgctgatgat cagactcctc acggcagcac tcaatcgtaa caggttttcc ttggtctttt   5940
acgcactcgg gggcgtcgtc ggcttggctg ctgagattgg gacttttgct ggtaaactga   6000
ctgaactgtc ccaggccttg tccacatact gcttcttacc tagggttgct gccatgacta   6060
gttgcgttcc catcatcatc atcggtgggc tccacaccct tggtgtgatt ctgtggctgt   6120
tcaaataccg tggtctccac aacatgctgg tcggtgatgg gagtttctca agcgccttct   6180
ttctgcggta ttttgcagaa ggcaatctaa ggaaaggcgt ttcgcagtct tgtggcatga   6240
gtaatgaatc tttaacggct gccctggcct gtaagttgtc acaggctgac ctagattttc   6300
tgtccagcct gacgaacttc aagtgctttg tgtctgcctc aaacatgaaa aatgctgctg   6360
gccagtacat tgaagcagcg tacgccaagg ccctgcgtca ggagttagct tctctagtcc   6420
aagttgataa aatgaaagga gtcctgtcca agctcgaagc ttttgctgaa acagcaaccc   6480
catccctgga cacaggagat gtgattgttc tactcgggca acatcctcac gggtccgttc   6540
ttgacatcaa tgttgggact gaaaggaaga ccgtgtcagt gcaagagacc cggagcctag   6600
gcgggtctaa attcagtgtc tgcaccgttg tgtccaacac accagtcgac accttgaccg   6660
gcatcccact tcaaacgccg acccactct ttgaaaatgg cccgcgccac cgcggtgagg    6720
atgacgacct taaagttgag aggatgaaga aacactgcgt ctccctcggt ttccataaca   6780
```

-continued

```
tcaatggcaa aatttactgc aaggtctggg acaagtccac cggagacacc ttctacacgg    6840
atgattcccg gtatacccaa gactatgcct ttcaggacag atcggctgat tacagagaca    6900
gagattatga gggtgtgcaa actgcccctc aacaaggatt tgacccgatg tctgaaaccc    6960
ccgttggtat tatcgtgatt ggcggtgtca cgtacaacag gtacttagct aaaggcaagg    7020
aggttttgat ccccaaacct gataaccatc tcgaggccgc taggctttcc ctcgagcaag    7080
ccctcgctgg gatgggccaa acttgtgatc ttacggctgt cgaggtggag aagttgaagc    7140
gcattatcag tcaactccaa ggcttgacca ctgagcaggc tttaaactgt tagccgccag    7200
cggcttgacc cgctgtggcc gcggcggctt agttgtgaca gaaacggcgg tgaagattgt    7260
gaaataccac agtagaactt tcaccttggg tcctctagac ttgaaagtca cttctgaggc    7320
ggaagtaaag aaatcaactg agcagggcca cgctgttgtg gcaaacttat gctccggtgt    7380
cgtcttaatg aggcctcacc cgccatctct cgttgatgta cttctggtgc ccggacttga    7440
cacagcaccc ggcattcaac cagggcatgg ggccggaaac atgggtgtga acggtgctat    7500
ttgggatttc gagactgcac ccactaaggc agagctcgag ttgtccaagc agataatcca    7560
ggcctgtgag gttaggcgcg gggacgcccc gaatctccag ctcctctaca gctttaccc     7620 tgttagggg gatcctgaac ggcgcaatgg ctgtctcatc aacaccaggt tcggagattt    7680
gccctataag actcctcaag acaccaagtc cgcgatccac gcggcttgct gcctgcaccc    7740 cgatgggcc ccgtgtctg atggcaagtc tacattaggt tccaccctcc aacgtggttt     7800
tgagctttac gtccccacag tgccttacag tgttttggag taccttgatt cacgccctga    7860 caccccctc atgtgtacca acatggcac ttctgaggct gctgcggagg acctccaaaa     7920
atacaacctg tccactcaag gatttgtcct gcctggagtc cttcgtttag ttcgcagatt    7980
cattttcggc catatcggaa aggcgccacc gttgtacctc ccatcaacct atcctgccaa    8040
aaactccatg gcagggatta atggccaaag gtttccgaca aaggatgtcc agagcatacc    8100
tgaaattgac gaaatgtgcg ctcgcgccgt caaagagaat tggcagactg tgacgccttg    8160
caccctcaag aagcagtact gttccaaacc caaaactaga accatcctgg gcactaacaa    8220
cttcattgcc ttggcgcaca gatcagcact cagtggtgtc acccatgcgt tcatgaagaa    8280
agcctggaaa tctccaattg ccttgggaaa gaacaaattt aaggagttgc actgtactgt    8340
cgccggcagg tgccttgagg ccgacttggc ttcctgtgat cgcagcaccc cagccatcgt    8400
aaggtggttt actgctaatc ttttgtatga acttgcaggg tgtgaggagt acttgcctag    8460
ctatgtgctc aactgctgtc atgatctcgt ggcaactcag gatggcgctt ttacaaagcg    8520
tggtggtctg tcgtctgggg accccgttac cagtgtgtcc aacactgtgt actcactggt    8580
gatttacgcc cagcacatgg tgctgtcagc actgaagatg ggccacgaaa ttggcctcaa    8640
gttcctcgag gaacaactca gttcgagga ccttattgaa attcagccca tgttggtgta     8700
ctctgatgac ctcgtcttgt atgctgagaa gcccaccttt cctaattacc actggtgggt    8760
cgagcacctt gatttgatgc tgggtttcaa gacggaccca aaaaaaacta ttataactga    8820
caaacccagc tttctcggct gcagaattga ggcagggcgg cagttagtcc ccaatcgcga    8880
ccgcatcctg gccgcccttg cataccacat gaaagcgcag aacgcttcag aatattacgc    8940
gtctgctgcc gcaatcctga tggattcatg tgcttgtatt gactatgacc ctgagtggta    9000
tgaggatctc atctgcggca ttgcccgtgt cgctcgtcaa gatggctata gttttccagg    9060
cccgccattt tttatgtcca tgtgggaaaa gctgaaaagt cacaatgaag ggaaaaaatt    9120
ccgccactgc ggtatctgtg atgccaaggc tgaccatgcg tccgcctgcg gcttgatttt    9180
gtgtttgttc cattctcact ttcatcagca ttgcccagtc atgcttagct gtggtcatca    9240
```

-continued

```
cgctggttta aaagaatgcc cgcagtgtca gtcaccagtc ggggctggca agtcccctct   9300
tgacaccgtg ttgcaacaaa tcccgtataa accaccccga actgtcataa tgaaggtgaa   9360
cagtaaaaca acagcccttg acccggggag gtatcagtcc cgtcggggtc ttgtcgcagt   9420
caagagggga attgcaggca atgaggttga tctcgctgac ggggactacc aggtggtacc   9480
cctcctgccg acctgcagag acataaatat ggtgaaggtg gcttgcaatg tactactcag   9540
caaattcata gtagggccac ccggctccgg aaagactacc tggttgctga accaagtcca   9600
agatgatgat gttatctata cacccaccca tcagaccatg tttgatatag tcagtgctct   9660
taaggtttgc aggtattcaa tcccaggagc ctcaggactc ccttttccac cgcctgccag   9720
atccggacca tgggtcaggc ttatcgccag cgggcacatc cctggccggg tctcatacct   9780
tgacgaggcc gggtattgca atcatctgga catcctcaga ctgctttcca aaacacccct   9840
cgtgtgtttg ggcgatcttc aacaacttca ccctgtcggc tttgattcct gttgttatgt   9900
ttttaatcag atgccacaca aacagctgac caccatttac aggttcggcc ctaatatctg   9960
tgccgccatc cagccttgtt acagggagaa gcttgaatcc aaggcaagaa acaccagggt  10020
ggttttcacc actcaacctg tggcctatgg tcaagtgctg acaccatttc acaaggatcg  10080
cgtagactca gccataacca tagattcatc tcagggtgcc acctttgacg tcgtgacgtt  10140
acacttgccg acgccaaaat ccctgaacaa atcccgagca cttgtggcta tcacccgggc  10200
gaggcatggg ctgttcatct atgatcctca taaccaactt caggagttct tcaacctaac  10260
ccctgagcgc acggattgca accttgtgtt caaccgtggg gatgaactgg tcgtcctgga  10320
tccagataat gcagtcacga ccgtagccaa ggccctgggg gccggcccgt ctcaattccg  10380
ggtgtccgat ccgaggtgca agtccctctt ggccgcttgc tcagtcagcc tggaaggtgg  10440
ctgcatgccg ctgccgcagg tggccataa tttgggggttt tatttctccc cagacagtcc  10500
ggcgtttgca cctctgccaa aagaactggc accacattgg ccggtggtta cctgccagaa  10560
caaccgggca tggcctgatc gactcgttgc cagcatgcgc ccgattgacg cccgttacag  10620
caagcctatg gttggtgcgg ggtatgttgt tgggccgtcc acctttcttg gaacccctgg  10680
tgtagtgtca tattacctca cactgtacat caagggtgag ccccaagccc taccagaaac  10740
actcgtttcg acagggcgta tagccacaga ctgccgggaa taccttgata cagctgaaga  10800
agaagcagct aaagaactcc ctcatgcttt cataggtgat gtcaaaggca ccacagtagg  10860
ggggtgtcac cacattacat caaaatactt acccaggtcc ctacccaagg actctgttgc  10920
agtggttggg gtgagctcac ctggcaaggc tgccaaagcg tgtgcactc tcactgatgt  10980 gtacctccct gaccttcggc cgtatctgca accagagaca gcatcaaaat gctggaaact  11040
caaattggac ttcagggacg tcagattgat ggtttggaaa ggggccactg cctatttcca  11100
attggaagga ctcacatggt cggcattacc cgactatgcc aggttcattc agctacccaa  11160
agatgccgta gtatacattg acccgtgtat aggaccggca acggccaacc gcaaggttgt  11220
gcgaaccact gactggcgag ctgacctggc ggtaacaccg tatgattacg gtgcccagac  11280
tattctgaca acagcctggt tcgaggacct cggaccacaa tggaaaatcc tggggctgca  11340 gcccttaag cggcatttg gcctcgaaaa cactgaagac tgggcaatcc tcgcacgccg  11400
tatgagtgac ggcagagatt acaccgacta caactggact tgtgttcgag aacgcccgca  11460
cgctatctac gggcgcgctc gtgaccacac gtatcatttc gccctggca cagaattgca  11520 ggtagaactg ggcaaacccc ggctgccgct tgagtgagta ctgcggctcg aaagccatgc  11580
aatggggtca ctgtggagta agatcactca gctgtttgtg gatgccttca ctgaattcct  11640
```

-continued

```
tgttagtgtg gttgacattg ttatcttcct tgccatacta ttcgggttca cagtcgcagg 11700
atggttactg gtcttctac tcagagtggt ttgctccgcg attctccgtt cgcgcactgc 11760
cattcactct cccgaattat cgaaggtcct atgaaggcct gctgcccaat tgcagaccgg 11820
atgttccaca attcgcaatc aagcatccat tgggcatcct ttggcacatg cgagtttccc 11880
atctaattga tgaaatggtc tctcgtcgtg tctaccaaac catggaacat tcaggccaag 11940
cggcctggaa gcaggcagtt gctgaagcca cacttacaaa gctatcgcag cttgacatgg 12000
tcacccactt ccagcatctt gccgcagtgg aagcggattc ttgtcgcttc ctcagttcgc 12060
gactcgtgat gctaaaaaac cttgctgtcg gcaatgtaag tctgctgtac aataccacat 12120
tggaccgtgt tgaactcatt ttccccacgc caggtgcgag gcccaaattg accgatttca 12180
gacaatggct catcagtgtt catgcttcta ttttctcttc tgtagcttcg tcagtcactt 12240
tgtttgtagt gctttggctt cgaattccag tgctacgcta tgttttggt ttccattggc 12300 ccacggcaac acgtcgttcg aactgaccat caattacacc gtatgcaagc cttgcattac 12360
tagacaagct gctgcccaac gactcgagcc tggtcgtaac atgtggtgca aaattgggta 12420
cgatcactgt gaagagcgtg atcacgatga gttgtcaatg ccatcccgt ccgggtacga 12480 caacactaaa cttgaaggct attatgcttg gcttgccttc ttgtcttttt cttatgcggc 12540
ccagtttcat ccagagctgt ttggaatagg gaatgtgtca cacgttttcg tggacaagca 12600
gcatcaattc atctgtgccg agcatgatgg gcaaaattca accatacccca acccacacaa 12660 catctctgca ttgtatgcgg tgtattatca ccaccaagtg gacggggca actggttcca 12720 tctagaatgg ctgcggccat tcttctcctc ctggttggtg ctcaatattt catgttttct 12780
gaggcgttcg cctgcaagcc ctgtttctcg acgcatctat cagatattaa aaccaacaca 12840
accgcggctg ccggtttcat ggtccttcaa gacattagct gttcccaacc ccatgagaga 12900
tcgggcacgc ggtcgtccgt tcgcgggaag ccatcccaat gtcgtacagc catcggcacc 12960
cccctgtaca tcacgctaac ggcgaatgtg actgatgaat cttatttgta caatgctgat 13020
ttattgatgc tttctgcttg cctgttttac gcctcggaaa tgagtgagaa gggcttcaaa 13080 gtcattttg gaaacgtctc tggtgttgtt tccgcgtgcg tcaatttcac agactatgtt 13140
acccatgtga ctcagcatac ccaacagcat catctggtag tcaaccatat ccggttgctg 13200
cactttatga caccgtcaac gatgaggtgg gccacaacca tcgcttgttt gctcgccatt 13260
ttattggcga tatgagatgt tttcccagat tgggcgtttt tttgactcct cactcttact 13320
tctggtggct ttcttgttg tgtaccggtt tatcctggtc cttgtgccgat ggcgacggca 13380 acagcccgac ataccaatac atatataact tgacgatatg tgagctgaat gggaccacct 13440
ggctgtccaa caattttac tgggcagtcg aaacttttgt gctttacccg gtggtgaccc 13500
acatcgtctc actgggtttc ctcacaacta gccatttctt tgacgcgctc ggcctcggag 13560
ctgtgtccgc tgtgggattt gctggcgggc ggtatgtcct cagcagcata tacggcgttt 13620
gtgcattcgc agcgctcgtg tgtttcatca tccgtgttgt taaaaattgc atggcgtgcc 13680
gctatgcccg tactcggttc accaacttca ttgttgacga ccgaggaaga attcacagat 13740
ggaagtcccc aatagtggtg gaaaaaatgg gtaaggccga agttggcagc agtctcgtca 13800
ccatcaagca tgttgttctc gaaggggtta aagctcaacc cttgacgagg actccggctg 13860
agcaatggga agcctagatg acttttgcta tgattccgcc gctacacaaa gcttctact 13920 agctttcagt atcacataca cacctgttat gatatacgcc cttaaggtat cacgcggccg 13980
acttttgggg cttttgcaca tcttgatttt cctgaattgt tccttcacat tcggatacat 14040
gacccatgag cgtttccatt ccaccaatcg tgtggcgctt actatgggag ctgttgtcgc 14100
```

```
tctcctgtgg ggcatctata gcctcacaga atcatggaag tttattactt ccaggtgcag   14160
attgtgttgc ctaggccggc aatacatcct ggccctgcc caccacgtag aaagtgccgc   14220
aggactccat tcaatcccgg cgtctggcaa ccgagcatac gccgtgagaa agcccggatt   14280
aacatcagtg aacggcactt tagtaccagg gcttcggagc ctcgtgttgg gcggcaagcg   14340
agctgttaaa cgaggagtgg ttaacctcgt caaatatggc cggtaaaaac cagagccaga   14400
agaagaagaa aaatacagct ccaatgggga atggccagtc agtcaatcaa ctgtgtcagt   14460
tgctgggcac gatgatgaga tcccagcgcc agcgatccaa gggggacag gccaaaaaga   14520 aaaagcttga aagccgcat ttcccctgg ccgctgaaga tgatgtccgg caccacctca   14580
cccaaaccga acgttccctt tgtctgcaat cgatccagac agcctttaat caaggtgcgg   14640
gaactgcgtc gctttcatcc agtgggaagg tcggttttca ggttgagttt atgctgccgg   14700
ttcctcatac ggtgcgcctg attcgcgtga cttccacatc cgccagtcag ggtgcaaatt   14760
aatttgatag tcaggtgaat ggccacgatt ggcgtgtggc ctctgagtca cctattcaat   14820
tagggcgatc acatgggggc tagacttaat caggcgagaa ccatgtgacc gaaatt      14876
```

The cDNA consensus sequence of PRRS strain PL 14-02 at P85 has been assigned GenBank Accession number MK024327 (SEQ. ID. NO:4). The cDNA consensus sequence designated SEQ. ID. NO:4 is:

```
atgatgtgta ggggagatac cctacacaca caacactcct agtgtttgtg taccttggag     60
gcgagggtac agccccgccc cactccttgg ccctgtttc agcccaacag ggacccttct    120
ccctcggggc gagtgtgccg cctgctgctc tctcgcagcg ggaaggacct cccgagtatt    180
tccggagagc acctgcttca cgggatctcc acccttaac catgtctggg atgttctccc    240
ggtgcatgtg caccccggct gcccgggtat tttggaacgc cggccaagtc ttttgcacac    300
ggtgtctcag tgcgcggtct cttctccctc tagagcttca ggactctgac ctcggcgctg    360
ttggctgttt ttataagcct agggacaagc ttcattggaa ggtccccatg gcatccctc    420 aggtggagtg cactccatcc ggatgctgtt ggctcgcagc cattttttcct atagcgcgta    480 tgacctccgg caatcacaat ttctcccagc gacttgtgaa agttgctgat gttttgtacc    540
gcgacggttg tctaacacct caacaccttc gtgaactcca agtttacgaa cgcggctgca    600
actggtaccc gatcacgggg ccagtgcccg gatgggtttt atttgcgaac tccgtgcacg    660
tgtctgacca gccgttcccc ggcgccactc atgtgttaac caactcacca ttgcctcagc    720
aggcttgtcg acagccgttc tgtccatttg aggtggctca ttctaacgta tacaggtggg    780
gggagtttgt gatctttgtg gactctcctt ccggcggtcg atcgcgtatg atgtggacac    840
cgggatccag tgactcggct gccctagaag cgttaccgtc cgcattagaa cgtcaggccg    900
gagtccttgt tcgaagtttc cctgcccacc acccgtcga ccttgctgac tgggagctta    960
ccgaatcccc tgaacacggt ttttccttca gcacatttca ttcttgtggt taccttgctc   1020
aaaaccccga aagttttgac ggtaagtgct ggctttcctg cttcctgggc ttgccgaccg   1080
gcgtgcggcg ttgtgaggaa tttttagctg gcgcctttgg ttatcaaacc aaatgggggg   1140
tgcacggaaa gtacctccaa cgtaggcttc agattaacgg ccttcgcgct gtggtcgatc   1200
ctgacggtcc catccatgtt gaagcacttt cttgtcccca gtcttggatc aggcatctga   1260
cttttgacga tgatgtcacc ccgggattcg ttcgcttaac atcccttcgc attgtgtcaa   1320
atacagagac cacctcctcc cagatctttc ggttcggggc gcataagtgg tacggcgctg   1380
ccggcaagcg ggctcgcgct aagcgtgctg caaagagtga aagaaatcg gttcccaccc   1440
```

-continued

```
ccgagactgt tccgctgacc cccgcctgtg gagtcaccat ctattcccca ccggcagacg 1500
ggtcctgtgg ttggcatgcc cttgccgcca tattgaacca gatgatgaac ggtgacttca 1560
cgtccccttt gcctcagtac aacaggccag aggatgattg ggcctctgac aacgaccttg 1620
ctcaagcaat tcaactcctg cgactaccgg ctaccatagt tcggactcgt gcctgtccta 1680
atgccaggta ccttataaag ctgaatgggg ttcactggga agtggaggag aggctgggga 1740
cggctctttg ctccctttct cgtgaatgtg tggttggtgt ttgctctgaa ggctgtgtcg 1800
catcgcctta tccaacagac ggggtaccag agcgtgcact cgaggccttg gcatctgctt 1860
acagactacc ctccgattgt gtttgctctg gtatttctga cttccttacc gaaccgcctc 1920
ctcaggaact ctggactctc gacaggatgt tgacctctcc atcacctgag cggtccggct 1980
tctccagttt gtataaatta ctgctcgagg ttgtccctca aaaatgcggt gctacggaag 2040
gggctttcac ctatgctgtt gagagaatgt tgagggactg ccgaagctcc aaacaagcca 2100
tggctctttt ggcgaaaatt aaagttccgt cttcaaaggc ttcatctgtg tccctggacg 2160
agtgtttccc tacgggtgct ccaggtgatt ctgagccagc acttcaggag gggcctcgaa 2220
gcctcggtgc tgccgttgtc ccatgcctgc ctggtgcaaa aggattcgag gaagcagccc 2280
cggaaggggt tcatgagaat ggctacgatg ccacccaccc tgcgctcttt gctgagcgtt 2340
ctaccaacga gcaggcacga atggcagccg gtaggcaatt ggggttcagc gatcgtgatt 2400
tggcagtcaa gaacattaat gaaggtgatt cggtctcggt tggtccaaca gaaggcacac 2460
tcaatggtca gggagacgaa ccactggatt tgtcccgacc agcactgacc actacaacga 2520
cccttatggg agaacgagaa cccgacaacc ctggttctga tgccggtgct tcccctgata 2580
ctgttcgaga attttccttg acggggctca cattccgtca tgttgagcac tgtggtacgg 2640
agtcgggtga cagcgattcg cctttggatt tgtctgacac gcagacccag gaccaacctt 2700
tagatctatc cctggcctct tggccagtga agctaccgc atctgacccc ggctgggttc 2760
acggtaggcg tgagcctgtc tttgtgaagc ctcgaaatgc tttctctgat ggcgattcag 2820
tccttcagtt tggagggctt tctgaacccg gctctgtcat cgagcctgac cagataaaag 2880 gtgcccggt gactgacacc cctaccgacc taacgacttc tgacgagtcc tttcccgcag 2940
gtgatcctct tgaactcgct gagcttaagc gcccacagtt ctccgtacag gccttaattg 3000
atcgaggggg cccacttgct gcattttatg caaaaataaa gaatcgggta tatgaacagt 3060
gcctccaagc ctgtgagccc ggtagtcgtg caaccccggc cactaaggag tggctcaaca 3120
aaatgtgggg tagggtagac atgaagactt ggcgttgtac ttcgcagttc gaagctggtc 3180
gctctcttgc gtcccttgaa ttcctccctg atatgatcaa cgacactcca cccctgttcc 3240
ccaggaataa ccgggtcagt gacgacgccg gcttgaagca actggtagca caatgggata 3300
agaaattgag cgcaccccc cccccaaaac tggttgggcc agtgatcgac cagagcgccc 3360
tcccaccagc aggtgtccaa caggaaaata tcaccccttc cgatgggccg cctcaagcgc 3420 cggatttttcc tggtcgagcg ggtacaggca gaggttggaa aggctttgtg ctttccggca 3480
ctcgtcttgc agagtctgtt agtcagcgcc ttatgacgtg gttttttgaa gtctactccc 3540
atctcccagc ttttatgctc gcacttttct cgccacgggg ctctatggtt ccaggtgatt 3600
ggttgtttgc agtgtgttgt ttacttgctc tcttgctctg tcgttcttac ccagtactcg 3660
ggtgtctacc cttactgggt gtatttctg gttctctacg gtgtgttcgt ctgggtgttt 3720
ttggttcttg gatggctttt gctgtatttt tattctcaac tccagccgat ccagtcggtt 3780
cttcttgtga ccacgattcg ccgaagtgtc atgctgagct tttggctctt gagcagcgcc 3840
aactttggga acctgtgcgc ggccttgttg tgggcccctc gggtctctta tgcgtcattc 3900
```

-continued

```
ttggcaagtt actcggtggg tcacgttatc tctggcatgt tttcttacgt ttatgcatgc   3960
ttgcggattt ggccctttct cttgtttatg tggtgtccca ggggcgttgt cgcaggtgtt   4020
ggggaaagtg tataaggaca gctcctatgg aggtggccct caacgtattc cctttttcgc   4080
gtgccacccg ctcctctctc gtgtccttgt gtgatcgttt tcaaacgcca aaaggggttg   4140
atcctgtgca cctggcaacg ggttggcgcg ggtgctggtg cggtgagagt cccatccatc   4200
aatcacatca aaagcccata gcttatgcca atttggatga aaagaaaata tctgcccaaa   4260
cagtagtcac tgtcccatat gatcccagtc aggctgtcaa gtgcctaaaa gttttgcagg   4320 caggggggggc catcgtagac cagcccacac ctgaggtcgt tcgtgtgtcc gagatcccct   4380
tctcagcccc atttttccca aaagttcccg tcaacccaaa ttgccgggtt gtagtggatt   4440
cagacacttt cgtggccgca gtccgatgcg gttactcaac agcacaactg gttctaggcc   4500
gtggtaactt tgctaagtta aatcaggccc ctcccaaaaa ctctgccctc accaaagcaa   4560
ctggtggggc ttcttacacc cttgctgtgg ctcaagtgtc tgtgtggact cttgttcatt   4620
tcatccttgg catttggctc acaacacctc aagtgtgtgg acgagggacc gtcgacccat   4680
ggtgtacaaa ccccttttcg taccccactt acggccccgg agttgtgtgc tctgctcgac   4740
tttgtgtgtc cgccgacggg gttaccctgc cgttgttctc tgccgtggca cagctctccg   4800
gtagggaggg agggatcttc attttggtac tcgcctcttt gggtgctctt gtccaccgcc   4860
tggctcttaa ggcagacatg ttaatggtct ttttggcttt ttgtgcttac gcctggccta   4920
tgagctcctg gttgatttgc ttcttcccca tactcttgaa gtgggtcaca cttcaccccc   4980
tcaccatgtt ttgggtacac tcattttttag tgttttgtct gccagcagcc ggtatcctct   5040
cactgggagt gactggtctt ctctgggcaa ttggccgctt tacccaggtt gccggaatta   5100 ttacaccta tgacatccat cagtacacct ctgggccacg tggtgcggcg gctatagcca   5160
cagcccctga aggcacttac atggccgccg tccggagagc cgctttaact gggcgaactt   5220
tgatcttcac cccgtcagca gtaggatccc ttcttgaggg agcctttagg acccgtaaac   5280
cctgcctcaa caccgtgaat gtcgtgggct cttcccttgg ttcaggaggg gttttcaccg   5340
ttggtggaaa gaaaataatc gtcaccgcag cccacgtgct gaatggtgac acggctagag   5400
tcaccggtga ctcctacaac cgcttgcaca ccttcaatac taatggtgat tacgcctggt   5460
ctcatgctga agactggcag ggcgttgccc ctgcagtcaa cattgcgaag gggtaccgcg   5520
gccgcgccta ttggcaaacg tcaaccggtg tcgagcccgg agttgttggg ggagggtttg   5580
ccttctgttt tactaactgc ggagactcgg ggtcacctgt tatctcagaa tctggtgatc   5640
ttattgggat tcacaccggc tcaaacaaac tcggctctgg tcttgtaaca acccctgaag   5700
gggaaacctg cactattaaa gaaaccaagc tctctgacct ttctaaacac tttgcaggcc   5760
caagcgttcc cctcggggac atcaaattga gtccggccat tatccctgac gtgacatcca   5820
ttccgagtga cttggcgtcg ctcttgactt ctgtccctgt aatggaaggc ggcctctcga   5880
ccgtccaact tttgtgtgtc ttttccttc tctggcgcat gatgggccat gcctggacac   5940
ccgttgttgc cgtgggcttc ttcctgctga atgaaatcct cccagcagtc ttggtccgga   6000
ctgtgttttc ttttgcactc tttgtgctgg catgggcaac cccttggtct gcacaggttt   6060
taatgatcag gcttctcacg gcatctctca atcgtaacag gtcttcttta gtgttctacg   6120
catttggagg catcgtcggc ttggccgttg aaatcgggac cttctctggc agattgcctg   6180
cattgtctca gcccctttcg acatattgct ttttacccag agcccttgtc atgaccagct   6240
gtgtccccac cattatcatt gggggattcc atatcctcgg tgtaatcttg tggttgttca   6300
```

-continued

```
aataccggta cctccacaac atgctggtcg gtgatgggag tttttcaagc gccttttcc   6360 tacggtattt tgctgaaggc aatctcagga agggtgtctc aaagtcttgt ggcatgagta   6420
acgagtccct aacggctgca ctggcctgca aattatcaca ggctgacctt gattttctat   6480
ccagcttgac gaacttcaag tgctttgtat ccgcttcaaa catgaaaaat gctgccggcc   6540
agtacattga agcagcgtat gccaaggccc tgcgccaaga gttggcctcc ctagttcaag   6600
tcgacaaaat gaaaggagtc ttgtccaagc tcgaagcttt tgctgagaca gccactccgt   6660
cccttgacgc gggtgacgtg atcgttcttc taggacaaca tcctcacggg tctgttctcg   6720
acatcaatgt gggggctgaa aggaaaactg tatctgtaca agagaccgg agtctaggcg   6780 gctccaaatt cagcgtctgc actgtcgtgt ccaacacacc catcgatgcc ttaactagta   6840
ttccactcca gacaccaacc ccactcttcg agaatggtcc gcgtcatcgt ggcgaggagg   6900
acgatctcaa agttgagagg atgaagaaac actgtgtgtc cctcggcttt cacaacatca   6960
atggcaaagt ttactgtaaa atttgggaca agtctaccgg cgacaccttc tacacagatg   7020
attcccggta tacccaggac tatgcttttc aagacagatc agtcgattac agggacaggg   7080
actatgaggg cgtacaaacc gtctcccatc agggattcga tccaaagtcc gaaaccctg    7140 tcggcactgt tgtgatcggc ggcattacgt ataacaggta tctgacaaag ggtaaagaaa   7200
ttctggttcc caggcctgac aactgccttg aagctgctaa attgtcctta gagcaagctc   7260
tcgccgggat gggtcagact tgcgaactta cgaccgccga gatggaaaag ttgaagcgca   7320
tcattagtca actccaaggt ttgaccactg aacaagcttt aaactgctag ccgccagcgg   7380
cttgacccgc tgtggccgcg gcggcttagt tgtgactgaa acggcggtaa aaattgtgaa   7440
ataccatagt agaactttta ccttaggctc cttagacctg aaggtcgctt ccgaggtaga   7500
ggttaaaaag tcagctgagc aaggccacgc tgttgtggca aacttatgct ccggtgtcat   7560
tttgatgaga ccccacccac cgtcccttgt tgatgttctt ctgaaacccg gacttgacac   7620
aaaacccggc attcaaccag gcatgggggc cgggaacatg ggcgtggatg gttctacttg   7680 ggatttgag accgcgccca caaaggcaga gcttgagtta tcgaagcaga taatccaagc    7740
atgtgaagtt aggcgcggag acgctcccaa cctccaactc ccttacaaac tttaccctgt   7800 caggggggaac cctgagcggc atgacggccg tctcactaac accaggtttg gagatttgcc   7860
ttacaagacc cctcaggaca ctaaatccgc aatccgcgcg gcttgttgcc tgcatcccaa   7920
tggggtcccc gtatctgatg gcaaatctac actaggtacc actcttcaac atggtttcga   7980
gctttatgtc cctaccgtgc cctatagtgt catggagtac cttgattcgc gttctgacac   8040
ccctctcatg tgtactagac atggcacttc caaagctgcc gcagaggacc tccaaaagta   8100
tgatttatcc acccaggggt ttgtcctgcc tggggtccta cgccttgtgc gcaagtttgt   8160
ttttggccat gttggtaagg caccgccatt gttccttcca tcaacctacc ccgcaaaaaa   8220
ctccatggca ggggtcaatg gccaaaggtt tcctacaaaa gatgttcaga gcatacctga   8280
agttgatgaa atgtgtgctc gcgccgtcaa ggagaattgg caaactgtga cgccttgtac   8340
tcttaagaaa cagtactgct ccaagctcaa aaccagaacc atcctgggca ccaacaattt   8400
tattgcccta gcccacagat cggcgctgag tggcgtcacc caggctttta tgaagaaggc   8460
ctggaattcc ccaattgcct tggggaaaaa taaattcaaa gagctgcact gtgttgtcgc   8520
cggcaggtgc cttgaggctg atctggcctc ctgtgaccgc agcacccctg ccgttgtaag   8580
atggtttgtt gccaacctcc tgtacgaact cgcggggtgt gaagagtatt gcctagcta   8640 tgtgctcaat tgctgccatg atctcgtagc aacacaggat ggtgccttta cgaaacgcgg   8700
tggcctgtcg tctggggacc ccgtcactag cgtgtccaac actgtgtatt cactgataat   8760
```

-continued

```
ttatgcccag catatggtgt tatcagcttt gaaaatgggt cacgaaattg gtctcaagtt    8820
ccttgaggaa cagcttaaat tcgaagacct tcttgaaatt cagcccatat tggtgtattc    8880
tgatgacctc gtattgtatg ccgaaagacc aacttttccc aactaccact ggtgggttga    8940
gcatcttgac ctaatgctgg gcttcaaaac ggacccggca aaaaccgtca taaccgacaa    9000
gcccagcttc ctcggctgta gaattgaggc agggcggcag ctagttccca atcgcgaccg    9060
catcctggct gctctcgcat accacatgaa ggcgcagaac gcctcagagt attatgcgtc    9120
tgctgctgca atcctaatgg attcatgtgc ttgcattgac cacgaccctg agtggtatga    9180
ggacctcatt tgcggtattg cccggtgcgc ccgccaggat ggttacagct cccaggtcc     9240
accattttc atgtctatgt gggagaaatt gagaagtcat aatgagggga agaaattccg     9300
ccattgcggc atctgcgacg ccaaagccga ccatgcgtcc gcttgcgggc ttgatttgtg    9360
tttgttccat tcgcactttc atcaacactg cccagtcact cttaactgcg gtcatcatgc    9420
cggttcaaag gaatgttcgc ggtgccagtc acctgttggg gctggaaaat cacctcttga    9480
tgccgtgcta gaacaaattc catacaaacc tcctcgcact gtcatcatga atgtgaacag    9540
tggaacgacg gcccttgatc cagggaggta ccagtcccgt cgtggcctcg ttgcagttaa    9600
gaggggtatc gcaggtaatg aagttgatct ccctgatgga gactatcaag tggtgcctct    9660
tttaccgact tgcaaagaca taaacatggt gaaggtggct tgcaatgtgc tgctcagtaa    9720
gttcatagtg gggccgccag gttccgggaa aaccacctgg ctattgagtc aagttcagga    9780
cgatgacgtc atttacacac ctacccacca gaccatgtat gacatagtta gcgccctcaa    9840
ggtttgtagg tattctatcc caggagcctc gggacttcct tttccgccac ctgccagatc    9900
cgggccgtgg gttaggcttg ttgctagcgg ctacgtccct ggccgagtgt catacctcga    9960
tgaggctgga tattgcaatc acctggacat tcttagactg ctttctaaaa cacccccttgt  10020
ttgtttgggt gacctccagc aacttcaccc tgtcggcttt gattcctact gttatgtgtt   10080
tgatcagatg cctcagaagc agttgactac catttataga ttcggtccta acatctgtgc   10140
agccatacag ccttgttaca gggagaaact cgaatccaag gctaggaata ccagggtggt   10200
cttcaccacc cgacctgtgg cctttggcca ggtgctgaca ccataccata aagatcgcgt   10260
cgactccgcg ataaccatag attcgtcaca gggggccacc ttcgacattg taacgttgca   10320
tttgccatca ccaaaatcct aaacaaatc ccgagcactt gtagccatca ctcgggctag   10380
gcacgggttg ttcatttacg atccccataa ccagctcagg gagttttca acctgacccc    10440
tgagcgtact gaatgcaacc tcgtgttcag ccgtggggat gagctggtgg ttctgaacgc   10500
ggacaatgca gtcacgactg tagtaaaagc cctagaggtg ggttcatccc agtttcgagt   10560
gtcagacccg aggtgtaaat ctctcttagc tgcttgttca gccagtctgg aggggagctg   10620
tatgccgtta ccccaagttg ctcataacct agggtttat ttttcccctg acagtccggc    10680
atttgcaccc ctgccaaaag agttggcacc acattggcca gtagttactc accagaataa   10740
tcgggcatgg ccagaccggc tcgtcgctag catgcgccca attgatgctc gctacagtaa   10800
accaatgatt ggtgctggtt atgtagtcgg accatccacc tttctcggca ctcctggcgt   10860
agtgtcatac tatctcaccc tatacattag gggtgagccc caggccttgc cagaaacact   10920
cgtgtcaaca ggacgcatag ccacagattg tcgggagtat cttgatacag ccgaggaaaa   10980
tgcggcaaaa gaactccctc acgcatttat tggtgatgtg aaaggcacta cggtcggtgg   11040
gtgccatcat attacatcaa aatacctgcc taggaccttg cctaaggact ctgttgccgt   11100
ggtcggagtg agttcgcccg gcaaggctgc taaagccatg tgtaccctca ccgatgtgta   11160
```

-continued

```
ccttcctgaa ctccgaccat atctgcaacc aaagacggca tcaaaatgct ggaaactcaa   11220
gttagacttc agggacgtcc gactgatggt ctggaagggg gctaccgcct acttccagct   11280
tgaagggctc acatggtctg cgctgcctga ttacgccagg ttcatccagc tacccacgaa   11340
tgccgtcgtg tacatcgacc cgtgcatagg accggcagca gccaaccgta aagttgtgcg   11400
aaccacggat tggagagcgg acctggcggt aacaccatat gactacggtg ctcaaaccat   11460
tctgacgaca gcctggttcg aggacctcgg gccacagtgg aaaattttag gactacagcc   11520
cttcaggcga gcattaggct ttgacaacac tgaggactgg gcaattcttg cacgccgtat   11580
ggatgacggt aaggattaca ttgactacaa ctggagttgt gttcgaaacc gcccatgcgc   11640
tatccatgga cgtgcgcgtg accacaccta tcattttgct catggtacgg aattaggggt   11700
ggagctgggt aaacctcggt taccgcctga ataagacccc cttgaaccca aagcaatgcg   11760
atgggttcat tatggagcaa aatcagtcaa ttgttcgtgg acgcttttac cgaattcctt   11820
gttagcgtgg ttgatattgt catctttctt gccatattgt tcgggttcac agtcgctgga   11880
tggctcctgg tctttttctct cagagtggtt tgctccgcga ttctccgttc gcgctctgcc   11940
attcactctc ccgagttatc gaaggtccta tgagggcctg ctgcccaatt gcaaaccaga   12000
tgtcccacaa ttcgcaatca agcacccact aggtttgctc tggcacatgc gagtctctca   12060
gttaatcgac gagatggtct ctcgtcgcat ttaccagacc atggaacact caggtcaggc   12120
agcctggaag caggtagtca gtgaggccac ccttacaaag ttgtcaaggc tcgatgtagt   12180
tgcccatttc caacatttgg ctgcagtgga ggcggattcc tgcaacttcc tcagctcacg   12240
acttgtgatg ctgaaaaatt tagctgtcgg taacgtgagt gtattttaca acgccacgtt   12300
ggaccgcgtt gaactcgtct tccccacgcc aggcacgagg cccaaattga ccgactttag   12360
gcaatggctt atcagcgtgc atgcttccat tttctcctct gtggcttcat cggttacctt   12420
gttcatggtg ctttggcttc gggttccaac tctacgctat gttttggtt tccattggcc   12480 cacggcaaca cgtcattcga gctgaccatc aactacacca tatgtatgcc ctgtcccacc   12540
agccaagcgg ctcaacaaag gctcgaaccc ggtcgtaata tgtggtgcaa gattggatac   12600
tctacgtgcg aggagcatga tcacgatgaa ctgtcgatgg ctataccacc tgggtatgac   12660
aatctcaaac ttgaaggcta ttatgcatgg ttggcttcct tgtccttttc ttacgcggct   12720
caattccatc cggagttatt cggaatgggg aatgtgtcgc gcgttttcgt ggacaagcag   12780
catcagttca tttgcgccga gcatgatgga cccaattcaa ccgtaaccac tggacataac   12840
atttccgcat tgtatgcggt gtactaccat caccaagttg acggggcaa ctggtttcat   12900 ttagaatggc tgcggccgtt cttctcctcc tggctggtgc tcaatatctc atggtttctg   12960
aggcgttcgc ctgcaagccc tgtttctcga cgcatctatc agatattaag accaacacga   13020
ccgcggctgc cggtttcatg gtccttcaga acatcgactg cctctcagca gcgcagagga   13080
gtgctcccgt cataaagtca tctcaatgcc gtgaagccat tggtacccca cagtacatta   13140
cgataacagc aaatgtgacc gatgaagcgt atttgtacaa tgcagactta ctgatgcttt   13200
ctgcatgcct tttctatgcc tcagaactga gcgagaaagg ctttaaagtt atctttggga   13260
atatctccgg tgtcgtctct gcatgcgtca atttcacgga ttatgtgact catgtgactc   13320
aacacacaca acagcatcat ttggtgatcg atcacgttcg gttgctgcat ttcctgacac   13380
cgtcagtgat gaggtgggct acaaccatcg cttgcttact tgccatcctt ctggcgatat   13440
gagatgttct cacaaattgg ggtgttttc gactctgtat tcctgctcct ggtggctttc   13500
tttgctgtgt accggcttgt cctggtcctt tgtcgatggc aacggcgaca gctcgacata   13560
ccaatatata taatttga cgatatgcga gctgaatgga accaaatggt tgtccaacca   13620
```

```
ttttgattgg gcagtcgaga ctttcgtgct ttacccggtc accactcaca tcatctcatt   13680
gggtttcctc acaacaagcc attttttttga cgcgctcggt cttagcgctg tatccattgt   13740
aggatttgct gatgagcggt acgtacttag tggtgtgtac ggtgcttgtg cttttgccgc   13800
gctcgtgtgt tttgtcatcc gtgctgctaa gaactgtatg gcttgtcgct atgcccgtac   13860
ccggttcacc aatttcattg tggacgaccg gggggaaatc caccgctgga agtcaccgat   13920
agtggtggaa aagttgggca aagctgaagt cggtgatgct cttgtcacca tcaagcatgt   13980
cgtcattgaa ggggttaaag ctcaacccctt gacgagaact tcggccgagc aatggcaaac   14040
ctagatgact tctgcaatga tcccactgcc gcgcaaaagc ttgtgctagc cttcagtatt   14100
acatacacac ctataatgat atatgccctc aaagtgtcac gcggccggct cctggggctg   14160
ttgcacatcc tgatatttct gaactgttct ttcacgtttg ggtacatgac gtatgtgcat   14220
tttcaatcca ccaatcgtgt cgcgcttact atggggctg ttgttgccct tttgtggggc   14280
atctatagtt ttacagaatc atggaggttt gtcacctcca ggtgcagact gtgttgccta   14340
ggccggcgat acattctggc ccctgcccat cacgtggaaa gtgccgcagg tctccattca   14400
atcccagcgt ctggcaaccg agcatacgct gtgagaaagc ccggactaac atcagtgaac   14460
ggcactctag taccaggact tcggagcctc gtgctgggcg gcaaacgagc tgttaaacgg   14520
ggagtggtta acctcgtcaa gtatggccgg taagaaccag agccagaaga aaaagcaaaa   14580
tacagctcct atggggaatg gccagtcagt caatcaactg tgccagctgc tgggtgtaat   14640
gatgaaatcc cagcgccaac ggcctagggg aggacaggca aaaagaaaa agcctgaaga   14700 gccacatttc cccctggctg ctgaggatga cattcggcac cacctcaccc aaactgaacg   14760
ttctctctgc ttgcaatcga tccaaacggc tttcaaccaa ggcgcaggaa ttgcgtcgct   14820
ttcacccagc gggaaggtca gttttcaggt tgagtttatg ttgccggttg ctcatacagt   14880
gcgcttgatt cgcgtgactt ctacacccgt cagtcagggt gctagttaat ttgacagtca   14940
ggtgaatggc cgcgattgac gtgtggcctc taagtcacct attcaattag ggcgatcaca   15000
tgggggttac acttaattag gcgagaacca tgtgaccgaa att                    15043
```

A person skilled in the art would recognize the polyadenosine tails, if any, of each of the genomic consensus sequences could vary in length from the above reported sequences.

---

What is claimed is:

1. A modified, live Porcine Reproductive and Respiratory Syndrome (PRRS) virus strain, wherein the consensus complementary DNA sequence of said PRRS strain is at least 95% identical to a sequence selected from the group consisting of SEQ ID NO: 1, SEQ ID NO: 2, SEQ ID NO: 3, and SEQ ID NO: 4.

2. The modified, live PRRS virus strain of claim 1, wherein the consensus complementary DNA sequence of said PRRS strain is at least 98% identical to a sequence selected from the group consisting of SEQ ID NO: 1, SEQ ID NO: 2, SEQ ID NO: 3, and SEQ ID NO: 4.

3. The modified, live PRRS virus strain of claim 1, wherein said PRRS strain is a DE 14-3073 strain designated PTA-125490; an ES 13-49 strain designated PTA-125489; an IT 14-32 strain designated PTA-125488, or a PL 14-02 strain designated PTA-125487.

4. The PRRS strain of claim 1, wherein said PRRS virus strain is passaged at least 85 times in tissue culture cells.

5. A product comprising a modified, live Porcine Reproductive and Respiratory Syndrome (PRRS) virus strain of claim 1 in the manufacture of a medicament for treating PRRS.

6. An immunogenic composition comprising a modified, live PRRS virus strain having a consensus complementary DNA sequence at least 90% identical to a sequence selected from the group consisting of SEQ ID NO: 1, SEQ ID NO: 2, SEQ ID NO: 3, and SEQ ID NO: 4, and a pharmaceutically-acceptable excipient, stabilizer, solubilizer, or diluent.

7. An immunogenic composition comprising a modified, live PRRS virus strain having a consensus complementary DNA sequence of claim 6 that is at least 95% identical to a sequence selected from the group consisting of SEQ ID NO: 1, SEQ ID NO: 2, SEQ ID NO: 3, and SEQ ID NO: 4, and a pharmaceutically-acceptable excipient, stabilizer, solubilizer, or diluent.

8. An immunogenic composition comprising a modified, live PRRS virus strain having a consensus complementary DNA sequence of claim 6 that is at least 98% identical to a sequence selected from the group consisting of SEQ ID NO:

1, SEQ ID NO: 2, SEQ ID NO: 3, and SEQ ID NO: 4, and a pharmaceutically-acceptable excipient, stabilizer, solubilizer, or diluent.

9. The immunogenic composition of claim 6, wherein the modified, live PRRS virus strain is a DE 14-3073 strain designated PTA-125490; an ES 13-49 strain designated PTA-125489; an IT 14-32 strain designated PTA-125488, or a PL 14-02 strain designated PTA-125487.

10. The immunogenic composition of claim 6, further comprising an adjuvant.

11. A vaccine comprising a modified, live PRRS virus strain, wherein said PRRS virus strain is a DE 14-3073 strain designated PTA-125490; an ES 13-49strain designated PTA-125489; an IT 14-32 strain designated PTA-125488, or a PL 14-02 strain designated PTA-125487.

12. A vaccine comprising a modified, live PRRS virus strain of claim 6 for the use in treatment or prevention of a symptom of Porcine Reproductive and Respiratory Syndrome in a porcine animal.

13. A method of treating and/or preventing a symptom of Porcine Reproductive and Respiratory Syndrome (PRRS) in a porcine animal, comprising administering to said porcine animal an immunogenic composition of claim 6 comprising a modified, live PRRS virus strain having a consensus complementary DNA sequence at least 98% identical to a sequence selected from the group consisting of SEQ ID NO: 1, SEQ ID NO: 2, SEQ ID NO: 3, and SEQ ID NO: 4.

14. The method of claim 13, wherein the symptom of PRRS is caused by a PRRS virus infection in a porcine animal.

15. A method of treating and/or preventing a symptom of Porcine Reproductive and Respiratory Syndrome (PRRS) in a porcine animal, comprising administering to said porcine animal a vaccine of claim 11 comprising a modified, live PRRS virus strain, wherein said PRRS virus strain is a DE 14-3073 strain designated PTA-125490; an ES 13-49 strain designated PTA-125489; an IT 14-32 strain designated PTA-125488, or a PL 14-02 strain designated PTA-125487.

16. The method of claim 15, wherein the symptom of PRRS is caused by a PRRS virus infection in a porcine animal.

17. A product comprising an immunogenic composition of claim 6 comprising a modified, live PRRS virus strain having a consensus complementary DNA sequence at least 98% identical to a sequence selected from the group consisting of SEQ ID NO: 1, SEQ ID NO: 2, SEQ ID NO: 3, and SEQ ID NO: 4 in the manufacture of a medicament for treating or preventing a symptom of Porcine Reproductive and Respiratory Syndrome (PRRS) in a porcine animal.

18. The product of claim 17, wherein the symptom of PRRS is caused by a PRRS virus infection in a porcine animal.

19. A product comprising a vaccine of claim 11 comprising a modified, live PRRS virus strain, wherein said PRRS virus strain is a DE 14-3073 strain designated PTA-125490; an ES 13-49 strain designated PTA-125489; an IT 14-32 strain designated PTA-125488, or a PL 14-02 strain designated PTA-125487 for treating and/or preventing a symptom of Porcine Reproductive and Respiratory Syndrome (PRRS) in a porcine animal.

20. The product of claim 19, wherein the symptom of PRRS is caused by a PRRS virus infection in a porcine animal.

\* \* \* \* \*